(12) United States Patent
Matulis et al.

(10) Patent No.: US 9,725,467 B2
(45) Date of Patent: Aug. 8, 2017

(54) FLUORINATED BENZENESULFONAMIDES AS INHIBITORS OF CARBONIC ANHYDRASE

(71) Applicant: VILNIUS UNIVERSITY, Vilnius (LT)

(72) Inventors: Daumantas Matulis, Vilnius (LT); Virginija Dudutiene, Vilnius (LT); Asta Zubriene, Vinius (LT)

(73) Assignee: VILNIUS UNIVERSITY, Vilnius (LT)

( * ) Notice: Subject to any disclaimer, the term of this patent is extended or adjusted under 35 U.S.C. 154(b) by 0 days.

(21) Appl. No.: 14/435,649

(22) PCT Filed: Oct. 30, 2012

(86) PCT No.: PCT/LT2012/000007
§ 371 (c)(1),
(2) Date: Apr. 14, 2015

(87) PCT Pub. No.: WO2014/062044
PCT Pub. Date: Apr. 24, 2014

(65) Prior Publication Data
US 2015/0266900 A1    Sep. 24, 2015

(30) Foreign Application Priority Data
Oct. 15, 2012 (LT) ...................... 2012 092

(51) Int. Cl.
| | | |
|---|---|---|
| C07D 513/04 | (2006.01) |
| C07D 233/84 | (2006.01) |
| C07C 311/29 | (2006.01) |
| C07C 311/39 | (2006.01) |
| C07C 317/14 | (2006.01) |
| C07C 317/18 | (2006.01) |

(Continued)

(52) U.S. Cl.
CPC .......... *C07D 513/04* (2013.01); *C07C 311/29* (2013.01); *C07C 311/37* (2013.01);
(Continued)

(58) Field of Classification Search
None
See application file for complete search history.

(56) References Cited

U.S. PATENT DOCUMENTS

2003/0092748 A1* 5/2003 Barrett .................. C07C 311/39
514/357
2009/0163586 A1    6/2009 Bylund et al.

FOREIGN PATENT DOCUMENTS

EP    2 147 915 A1    1/2010
GB    1 025 314 A    4/1966
(Continued)

OTHER PUBLICATIONS

Database CAPLUS Chemical Abstracts Service, Columbus, Ohio, US; Database Accession No. 1966:3907, Abstract of NL 6500208, Farbenfabriken Bayer A.-G. Jul. 12, 1965.*

(Continued)

*Primary Examiner* — Karl J Puttlitz
(74) *Attorney, Agent, or Firm* — Young & Thompson

(57) ABSTRACT

Novel fluorinated benzenesulfonamides compounds of general formula (I)

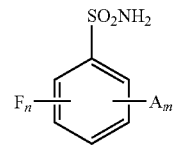

(I)

Figure 1:
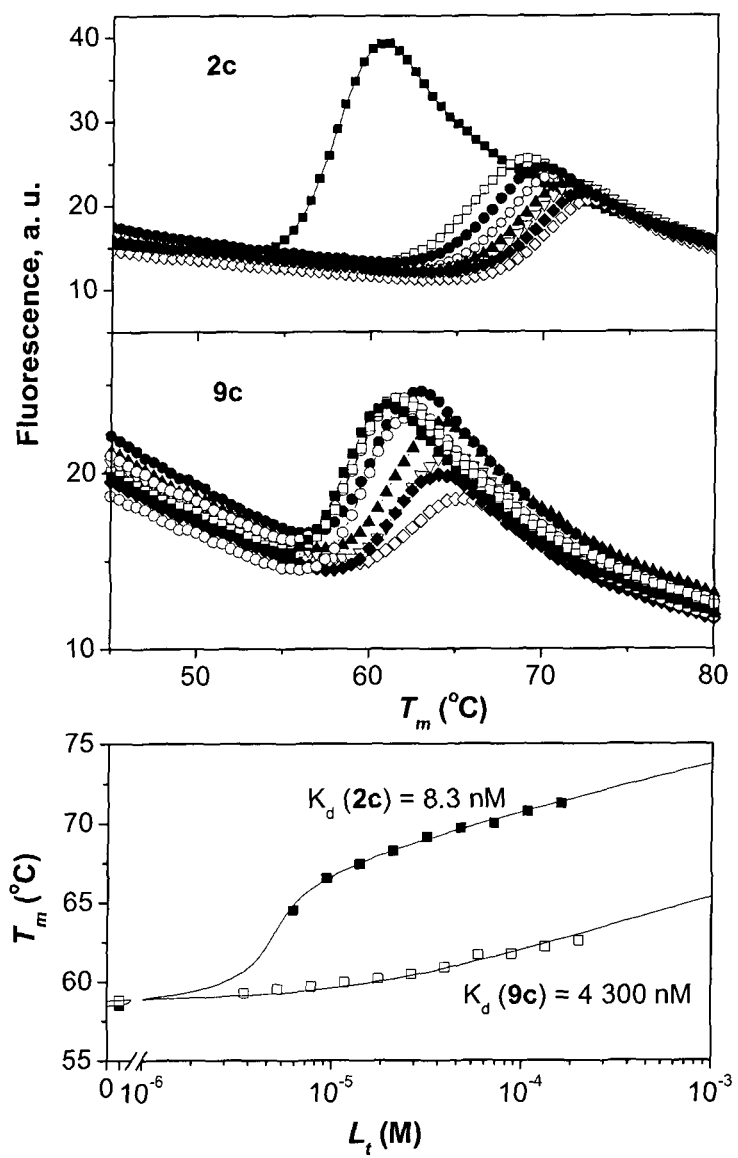

can be used in biomedicine as active ingredients in pharmaceutical formulations, because they inhibit enzymes which participate in disease progression.

5 Claims, 4 Drawing Sheets

(51) Int. Cl.
*C07C 317/36* (2006.01)
*C07D 239/38* (2006.01)
*C07C 323/67* (2006.01)
*C07D 277/74* (2006.01)
*C07D 295/096* (2006.01)
*C07C 311/37* (2006.01)
*C07C 317/22* (2006.01)
*C07D 237/18* (2006.01)

(52) U.S. Cl.
CPC .......... *C07C 311/39* (2013.01); *C07C 317/14* (2013.01); *C07C 317/18* (2013.01); *C07C 317/22* (2013.01); *C07C 317/36* (2013.01); *C07C 323/67* (2013.01); *C07D 233/84* (2013.01); *C07D 237/18* (2013.01); *C07D 239/38* (2013.01); *C07D 277/74* (2013.01); *C07D 295/096* (2013.01); *C07C 2101/14* (2013.01); *C07C 2101/18* (2013.01); *C07C 2101/20* (2013.01); *C07C 2102/08* (2013.01); *C07C 2102/10* (2013.01); *C07C 2103/74* (2013.01)

(56) References Cited

FOREIGN PATENT DOCUMENTS

| | | | |
|---|---|---|---|
| GB | 1 031 082 A | | 5/1966 |
| NL | 6500208 | * | 7/1965 |
| WO | 2008/017932 A2 | | 2/2008 |
| WO | 2009/118292 A1 | | 10/2009 |
| WO | 2010/004139 A1 | | 1/2010 |
| WO | 2010004139 | * | 1/2010 |
| WO | 2011/029842 A1 | | 3/2011 |
| WO | 2011/071565 A1 | | 6/2011 |

OTHER PUBLICATIONS

Database CAPLUS Chemical Abstracts Service, Columbus, Ohio, US; Database Accession No. 1967:94741, Abstract of Yakobson et al., Zhurnal Obshchei Khimii (1967), 37(1), 163-70.*
Database CAPLUS Chemical Abstracts Service, Columbus, Ohio, US; Database Accession No. 2000:493507, Abstract of US Publication No. 20030092748, Barrett et al., May 15, 2003.*
Virginija Dudutiene et al.: "4-Substituted-2.3.5.6-tetrafluorobenzenes ulfonamides as inhibitors of carbonic anhydrases I. II. VII. XII. and XIII", Bioorganic & Medicinal Chemistry, Jan. 1, 2013 (Jan. 1, 2013), XP055055325, ISSN: 0968-0896. DOI: 10.1016/j.bmc.2013.01.008 the whole document.
Xavier De Leval et al.: "Carbonic Anhydrase Inhibitors: Synthesis and Topical Intraocular Pressure Lowering Effects of Fluorine-Containing Inhibitors Devoid of Enhanced Reactivity", Journal of Medicinal Chemistry, vol. 47. No. 11. May 1, 2004 (May 1, 2004), pp. 2796-2804. XP055055369, ISSN: 0022-2623. DOI: 10.1021/m0311169, the whole document.
International Search Report, dated Mar. 13, 2013, from corresponding PCT application.

* cited by examiner

FLUORINATED BENZENESULFONAMIDES AS INHIBITORS OF CARBONIC ANHYDRASE

FIELD OF THE INVENTION

The present invention describes novel aromatic sulfonamide derivatives, potentially useful in biomedicine as active ingredients of pharmaceutical preparations because of their ability to inhibit enzymes participating in disease progression.

The enzymes in this description of the invention include different metal (mostly zinc) ion-possessing proteins, such as carbonic anhydrases and metalloproteinases.

BACKGROUND OF THE INVENTION

Carbonic anhydrases are zinc-containing enzymes which catalyze reversible reaction of carbon dioxide hydration. These enzymes participate in essential physiological processes related to respiration, $CO_2$/bicarbonate transport between lungs and metabolizing tissues, pH and $CO_2$ homeostasis, electrolyte secretion in many tissues/organs, etc. To date there are 15 carbonic anhydrase (CA) isozymes identified in humans—12 catalytically active and 3 inactive, so called carbonic anhydrase related proteins. The 12 active isoforms have different subcellular localization—5 of them are cytosolic, 4—membrane bound, 2 mitochondrial and 1—secreted. The major class of carbonic anhydrase inhibitors is aromatic and heterocyclic inhibitors possessing sulfonamide group. Sulfonamide-class carbonic anhydrase inhibitors are widely used as therapeutic agents for treatment of various diseases, since the 15 carbonic anhydrase isozymes are widely distributed in most of the cells, tissues and organs where they are responsible for essential physiological functions. Another similar protein class is metalloproteinases, proteolytic enzymes, which are characterized by increased expression during various steps of cancer progression. Sulfonamide inhibitors have a great potential for the inhibition of metalloproteinases.

Carbonic anhydrases participate in many essential physiological processes, therefore the increased activity or expression of different CA isoforms results in significant pathological outcomes. Therefore the regulation of CA catalytic activity by means of inhibition or activation proposes a therapeutic perspective.

There are several diseases with the characteristic disbalance of the interconversion between carbon dioxide and bicarbonate resulting in pH alteration, disturbance of ion transport, fluid secretion, etc. CA activators may have pharmacological applications in pathologies in which learning and memory are impaired, such as Alzheimer's disease or aging (Temperini, C. et al. (2009), *Drug Design of Zinc-Enzyme Inhibitors: Functional, Structural, and Disease Applications*; Eds.: Supuran, C. T. and Winum, J.-Y., Wiley: Hoboken, N.J., p 473). While most often carbonic anhydrase inhibitors are used as antiglaucoma agents, they are also employed for treatment of another diseases: retinal and cerebral edema (inhibitors of CA I) (Gao, B. B. et al. (2007), *Nat. Med.* 13, 181), altitude sickness (inhibitors of CA II) (Basnyat, B. et al. (2003), *High Alt. Med. Biol.* 4, 45), epilepsy (inhibitors of CA II, CA VII, CA XIV) (Hen, N. et al. (2011), *J. Med. Chem.* 54, 3977). Few novel synthesized inhibitors of CA VA, CA VB, CA XII and CA IX are undergoing clinical investigation as antiobesity and antitumor drugs or diagnostic tools (De Simone, G. et al. (2008), *Curr. Pharm. Des.* 14, 655; Guler, O. O. et al. (2010), *Curr. Med. Chem.* 17, 1516). It was identified that CA inhibitors suppress the growth of leukemia, melanoma, lung, ovarian, colon, kidney, prostate, breast, and CNS cancer cells (Supuran, C. T. et al. (2000), *Eur. J. Med. Chem.* 35, 867; Guler, O. O. et al. (2010), *Curr. Med. Chem.* 17, 1516; De Simone, G. et al. (2010), *Biochim. Biophys. Acta,* 1804, 404; Battke, C. et al. (2011), *Cancer Immunol. Immunother.* 60, 649). Namely, the carbonic anhydrases IX and XII are directly related to cancer development. The use of CA IX-specific inhibitor set for detection and treatment of pre-cancer and neoplastic state is described (WO 2004/048544). There are a few reports about CA XIII involvement in the sperm mobility processes (probably together with CA XIV). Inhibition of these two CAs may be used in obtaining contraceptive agents (Lehtonen, I. et al. (2004), *J. Biol. Chem.* 279, 2791). It was established that CA inhibitors are useful diuretics for the treatment of patients which suffer from edema and heart deficiency. It is supposed that inhibition of the CA II activity could be useful for the diminishment of the bone resorption. It was shown in prokaryotes that the carbonic anhydrases are essential for respiration, carbon dioxide transport and photosynthesis. Therefore it was hypothesized that carbonic anhydrase inhibitors could be used as antibiotics. Ethoxzolamide was even used for the treatment of meningitis. It was noticed that carbonic anhydrase inhibitors possess an antimallarial activity. (Merlin, C. et al. (2003), *J. Bacteriol.* 185, 6415; Pastorekova, S. et al. (2004), *J. Enzyme Inhib. Med. Chem.* 19, 199; WO 2005/107470).

Introduction of fluorine atom as substituent in various positions of the benzene ring of benzenesulfonamides was investigated from point of view as CA inhibition. Pentafluorobenzenesulfonamide was described as bCAII inhibitor (Olander, J. et al. (1973), *JACS,* 95, 1616; Krishnamurthy, V. M. et al. (2007), *Chem. Asian J.* 2, 94). As far as known to the authors of this invention, there are no mention in the literature about 4-substituted-2,3,5,6-tetrafluorobenzenesulfonamides activity towards CA inhibition. Such compounds bearing cycloalkylamino or alkylamino groups in 4-position were described as anticonvulsants (GB 1031082, BE 659230 (original)). The compound 4-methoxy-2,3,5,6-tetrafluorobenzenesulfonamide was described as anticonvulsant too (GB 1025314, BE 664831). The compounds 4-piperonyl-2,3,5,6-tetrafluorobenzenesulfonamide and 4-(cyclohexylamino)-2,3,5,6-tetrafluorobenzenesulfonamide was mentioned in article about detection of sulfonamido groups (Bradshaw, L. R. A. (1969), *Journal of Chromatography,* 44, 422). The synthesis of 4-methoxy- and 4-amino-2,3,5,6-tetrafluorbenzensulfonamides was described (Robson, P. et al. (1963), *J. Chem. Soc.* 3692). The synthesis of non substituted 2,3,5,6-tetrafluorbenzensulfonamide was described in the same article. As far as known to the authors of this invention, there are no mention in the literature about 2,4-disubstituted-3,5,6-trifluorobenzenesulfonamides and 3,4-disubstituted-2,5,6-trifluorobenzenesulfonamides. The compounds 2-substituted-3,5,6-trifluorobenzenesulfonamides have not been investigated as CA inhibitors according to authors of this invention. It is known only that compound 2-cyclopropylamino-3,5,6-trifluorobenzenesulfonamide was used for preparation of benzothiadiazine derivatives, which were used as AMPA receptor modulators (WO 2010004139). The synthesis of non substituted 2,3,5-trifluorobenzenesulfonamide, 2,3,4-trifluorobenzenesulfonamide, 2,3,6-trifluorobenzenesulfonamide and 2,4,6-trifluorobenzenesulfonamide and their use for preparation of benzothiadiazine derivatives was described in the same patent. Preparation of pyrazolylbenzothiazoles bearing fragment of 2,3, 4-trifluorobenzenesulfonamide and their use as inhibitors of integrin-linked kinase was described (WO 2004011460). The synthesis of 2,3,4-trifluorobenzenesulfonamide and use as intermediate compound for preparation of 2,3-difluorobenzensulfonamide derivatives was described in another patent (WO 2008017932). These derivatives were investigated as CA inhibitors. As far as known to the authors of this invention, there are no mention in the literature about 3,4,5-trisubstituted-2,6-difluorobenzenesulfonamides. Other substituted difluorobenzenesulfonamides are investigated vaguely as CA inhibitors. Derivatives of 2,3-difluorobenzensulfonamide were described in patent (WO 2008017932). Such fluorinated benzenesulfonamides as non substituted 2,6-difluorobenzenesulfonamide and 3,5-difluorobenzenesulfonamide were investigated for the same reason (Krishnamurthy, V. M. et al. (2007), Chem. Asian J. 2, 94). The compound 5-(aminosulfonyl)-2,3-difluorobenzoic acid was described as intermediate compound for preparation of mono fluorinated substituted benzenesulfonamides as CA inhibitors (Vernier, W. et. al. (2010), Biorg. Med. Chem. 18, 3307). But there are a lot of data about substituted difluorobenzenesulfonamides bearing fluorine atoms in different positions and their use for different purposes than CA inhibition. 4-Substituted-2,3-difluorobenzenesulfonamides were intermediates for preparation of benzothiadiazine derivatives, which were used as AMPA receptor modulators (WO 2010004139). Substituted 2,3-difluorobenzenesulfonamides were investigated as prostaglandin E synthase-1 inhibitors (US 20090163586), matrix metalloprotease inhibitors (WO 2009118292). Substituted 2,4-difluorobenzenesulfonamides were intermediates for preparation of benzothiadiazine derivatives, which were used as AMPA receptor modulators (WO 2010004139). Substituted 2,4-difluorobenzenesulfonamides were investigated as mGluR2 antagonists (WO 2007110337, WO 2006099972), TRPV1 inhibitors (US 20080146637), CCR5 antagonists (WO 2004054974), prostaglandin E synthase-1 inhibitors (US 20090163586). Substituted 2,5-difluorobenzenesulfonamides were intermediates for preparation of benzothiadiazine derivatives, which were used as AMPA receptor modulators (WO 2010004139). Substituted 2,5-difluorobenzenesulfonamides were investigated as dipeptidyl peptidase IV inhibitors (CN 101418001). Substituted 2,6-difluorobenzenesulfonamides were intermediates for preparation of benzothiadiazine derivatives, which were used as AMPA receptor modulators (WO 2010004139). Substituted 3,4-difluorobenzenesulfonamides were intermediates for preparation of benzothiadiazine derivatives, which were used as ATP-Sensitive Potassium Channel Openers (de Tullio, P. et. al. (2005), J. Med. Chem. 48, 4990). Substituted 3,4-difluorobenzenesulfonamides were intermediates for preparation of N-(phenylsulfonyl)benzamides and N-(3-pyridylsulfonyl)benzamides as apoptosis-inducing agents for the treatment of cancer and immune diseases and autoimmune diseases (US 20110124628). Substituted 3,4-difluorobenzenesulfonamides were investigated as prostaglandin E synthase-1 inhibitors (US 20090163586), CCR5 antagonists (WO 2004054974). Substituted 3,5-difluorobenzenesulfonamides were intermediates for preparation of N-(phenylsulfonyl)benzamides and N-(3-pyridylsulfonyl) benzamides as apoptosis-inducing agents for the treatment of cancer and immune diseases and autoimmune diseases (US 20110124628). Substituted 3,5-difluorobenzenesulfonamides were investigated as prostaglandin E synthase-1 inhibitors (US 20090163586), TGR5 agonists (WO 2010093845, WO 2011071565), for treatment of cancer (WO 2011029842). Substituted 3,6-difluorobenzenesulfonamides were investigated for preparation of substituted imidazolidine-2,4-diones (WO 2008017381).

Despite the fact that a large number of different sulfonamides have been synthesized to date, the available pharmaceutical agents created on the basis of these sulfonamides have a number of shortcomings. One of the main shortcomings is the non-selective inhibition of all carbonic anhydrases throughout the whole human body. This results in various unexpected side effects, mostly because of non-specific inhibition of all CA isoforms and their toxicity.

Presently clinically used CA inhibitors, when acting non-specifically, cause a number of side-effects. Especially toxic are systemic inhibitors. They cause electrolyte disbalance, drowsiness, head-ache, depression, apathy, malaise, irritability, nervousness, fatigue, gut irritability, anorexia, nausea, thirst, obstruction, muscle weakness, tremor, hyper- and hypoglycemia, kidney pain, disuria, bone marrow depression, metabolic acidosis and other.

Therefore, the creation of isoform-specific or organ-selective sulfonamide inhibitors is still an important task.

Invented compounds show great possibility to synthesize fluorinated benzenesulfonamides bearing different substitutes in o, m, p positions according to sulfonamide group. Presence of fluorine atoms in such compounds exerts an acidifying effect on the sulfonamide protons, which correlates with an increase in the CA inhibitory properties. These features enable good possibilities to create isoform-specific sulfonamide inhibitors.

SUMMARY OF THE INVENTION

This invention describes new sulfonamides with general structural formula (I)

where
n>1, n<5 (2-4 fluorine atoms in any position),
m≥1, (1-3 A groups are identical or different from each other, at least one A≠H)
A is H, $R^1$, OH, $OR^1$, SH, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, Cl, Br, I, CN, $NO_2$, $N_3$, $C(O)H$, CHNOH, $CH(NOCH_3)$, $CF_3$, $CF_2CF_3$, $OCF_3$, $OCF_2CF_3$, $C(O)OH$, $C(O)NH_2$,
$R^1$ is $R^2$, $R^3$, $R^4$, $R^5$, $R^6$, $R^7$,
$R^2$ is phenyl, which is unfused or fused with benzene, heteroarene, cycloalkane or heterocycloalkane,
$R^3$ is heteroaryl, which is unfused or fused with benzene, heteroarene, cycloalkane or heterocycloalkane,
$R^4$ is cycloalkyl, cycloalkenyl, cycloalkynyl, heterocycloalkyl, heterocycloakenyl or heterocycloalkynyl, each of which is unfused or fused with benzene, heteroarene, $R^5$ is alkyl, alkenyl or alkynyl each of which is unsubstituted or substituted by one or more identical or different groups selected from $R^5$ is $R^8$, OH, $OR^8$, SH, $SR^8$, $S(O)R^8$, $SO_2R^8$, $C(O)R^8$, $C(O)OR^8$, $OC(O)R^8$, $NHR^8$, $N(R^8)_2$, $C(O)NHR^8$, $C(O)N(R^8)_2$, $NHC(O)R^8$, $NR^8C(O)R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $SO_2NHR^8$, $SO_2N(R^8)_2$, $NHSO_2R^8$, $NR^8SO_2R^8$, $NHSO_2NHR^8$, $NHSO_2N(R^8)_2$, $NR^8SO_2NHR^8$, $NR^8SO_2N(R^8)_2$, C(O)NHNOH, $C(O)NHNOR^8$, $C(O)NHSO_2R^8$, $C(NH)NH_2$, $C(NH)NHR^8$, $C(NH)N(R^8)_2$, $NHSO_2NHR^8$, $NHSO_2N(CH_3)R^8$, $N(CH_3)SO_2N(CH_3)R^8$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$, $R^8$ is $R^9$, $R^{10}$, $R^{11}$, $R^{12}$, $R^{13}$, $R^{14}$, $R^9$ is phenyl, which is unfused or fused with benzene, heteroarene, cycloalkane or heterocycloalkane, $R^{10}$ is heteroaryl, which is unfused or fused with benzene, heteroarene, cycloalkane or heterocycloalkane, $R^{11}$ is cycloalkyl, cycloalkenyl, cycloalkynyl, heterocycloalkyl, heterocycloakenyl or heterocycloakynyl, each of which is unfused or fused with benzene, heteroarene, $R^{12}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{13}$ is phenyl which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{14}$ is heteroaryl, which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^6$ is phenyl which is unsubstituted or substituted by one or more identical or different groups selected from $R^6$ is $R^{15}$, OH, $OR^{15}$, SH, $SR^{15}$, $S(O)R^{15}$, $SO_2R^{15}$, $C(O)R^{15}$, $C(O)OR^{15}$, $OC(O)R^{15}$, $NHR^{15}$, $N(R^{15})_2$, $C(O)NHR^{15}$, $C(O)N(R^{15})_2$, $NHC(O)R^{15}$, $NR^{15}C(O)R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $SO_2NHR^{15}$, $SO_2N(R^{15})_2$, $NHSO_2R^{15}$, $NR^{15}SO_2R^{15}$, $NHSO_2NHR^{15}$, $NHSO_2N(R^{15})_2$, $NR^{15}SO_2NHR^{15}$, $NR^{15}SO_2N(R^{15})_2$, C(O)NHNOH, $C(O)NHNOR^{15}$, $C(O)NHSO_2R^{15}$, $C(NH)NH_2$, $C(NH)NHR^{15}$, $C(NH)N(R^{15})_2$, $NHSO_2NHR^{15}$, $NHSO_2N(CH_3)R^{15}$, $N(CH_3)SO_2N(CH_3)R^{15}$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$, $R^{15}$ is $R^{16}$, $R^{17}$, $R^{18}$, $R^{19}$, $R^{20}$, $R^{21}$, $R^{16}$ is phenyl, which is unfused or fused with benzene, heteroarene, cycloalkane or heterocycloalkane, $R^{17}$ is heteroaryl, which is unfused or fused with benzene, heteroarene, cycloalkane or heterocycloalkane, $R^{18}$ is cycloalkyl, cycloalkenyl, cycloalkynyl, heterocycloalkyl, heterocycloakenyl or heterocycloakynyl, each of which is unfused or fused with benzene, heteroarene, $R^{19}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{20}$ is phenyl which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{21}$ is heteroaryl, which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^7$ is heteroaryl, which is unsubstituted or substituted by one or more identical or different groups selected from $R^7$ is $R^{22}$, OH, $OR^{22}$, SH, $SR^{22}$, $S(O)R^{22}$, $SO_2R^{22}$, $C(O)R^{22}$, $C(O)OR^{22}$, $OC(O)R^{22}$, $NHR^{22}$, $N(R^{22})_2$, $C(O)NHR^{22}$, $C(O)N(R^{22})_2$, $NHC(O)R^{22}$, $NR^{22}C(O)R^{22}$, $NHC(O)OR^{22}$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $SO_2NHR^{22}$, $SO_2N(R^{22})_2$, $NHSO_2R^{22}$, $NR^{22}SO_2R^{22}$, $NHSO_2NHR^{22}$, $NHSO_2N(R^{22})_2$, $NR^{22}SO_2NHR^{22}$, $NR^{22}SO_2N(R^{22})_2$, C(O)NHNOH, $C(O)NHNOR^{22}$, $C(O)NHSO_2R^{22}$, $C(NH)NH_2$, $C(NH)NHR^{22}$, $C(NH)N(R^{22})_2$, $NHSO_2NHR^{22}$, $NHSO_2N(CH_3)R^{22}$, $N(CH_3)SO_2N(CH_3)R^{22}$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$, $R^{22}$ is $R^{23}$, $R^{24}$, $R^{25}$, $R^{26}$, $R^{27}$, $R^{28}$, $R^{23}$ is phenyl, which is unfused or fused with benzene, heteroarene, cycloalkane or heterocycloalkane, $R^{24}$ is heteroaryl, which is unfused or fused with benzene, heteroarene, cycloalkane or heterocycloalkane, $R^{25}$ is cycloalkyl, cycloalkenyl, cycloalkynyl, heterocycloalkyl, heterocycloakenyl or heterocycloakynyl, each of which is unfused or fused with benzene, heteroarene, $R^{26}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{27}$ is phenyl which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{28}$ is heteroaryl, which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I.

The objects of the invention are also the non-toxic, pharmaceutically acceptable salts of the sulfonamides of general formula (I). They include all salts which retain activity comparable to original compounds and do not attain any harmful and undesirable effects. Such salts are obtained from compounds with general structural formula (I), by mixing their solution with pharmacologically acceptable acids or bases.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid and other.

Among the pharmaceutically acceptable bases there may be mentioned, without implying any limitation, sodium hydroxide, potassium hydroxide, triethylamine and tert-butylamine.

The examples of the implementation of the invention are compounds: 4-substituted-2,3,5,6-tetrafluorobenzenesulfonamides, 2,4-disubstituted-3,5,6-trifluorobenzenesulfonamides, 2-substituted-3,5,6-trifluorobenzensulfonamides, 3,4-disubstituted-2,5,6-trifluorobenzenesulfonamides, 3,4,5-trisubstituted-2,6-difluorobenzenesulfonamides.

Examples of the invented compounds are selected compounds from the group comprising:

2,3,5,6-tetrafluoro-4-hydrazinobenzenesulfonamide;
4-(2-benzylidenehydrazino)-2,3,5,6-tetrafluorobenzenesulfonamide;
2,3,5,6-tetrafluoro-4[(2-hydroxyethyl)thio]benzenesulfonamide;
2,3,5,6-tetrafluoro-4[(2-hydroxyethyl)sulfonyl]benzenesulfonamide;
2-{[4-(aminosulfonyl)-2,3,5,6-tetrafluorophenyl]sulfonyl}ethyl acetate;
2,3,5,6-tetrafluoro-4-(propylthio)benzenesulfonamide;
{[4-(aminosulfonyl)-2,3,5,6-tetrafluorophenyl]thio}acetic acid;
3-{[4-(aminosulfonyl)-2,3,5,6-tetrafluorophenyl]thio}propanoic acid;
6-{[4-(aminosulfonyl)-2,3,5,6-tetrafluorophenyl]amino}hexanoic acid;
2,3,5,6-tetrafluoro-4-(phenylthio)benzenesulfonamide;
2,3,5,6-tetrafluoro-4-(phenylsulfonyl)benzenesulfonamide;
2,3,5,6-tetrafluoro-4-phenoxybenzenesulfonamide;
4-(benzylthio)-2,3,5,6-tetrafluorobenzenesulfonamide;
4-(benzylamino)-2,3,5,6-tetrafluorobenzenesulfonamide;
2,3,5,6-tetrafluoro-4-{[2-(4-hydroxyphenyl)ethyl]amino}benzenesulfonamide;
2,3,5,6-tetrafluoro-4-[(2-phenylethyl)thio]benzenesulfonamide;
2,3,5,6-tetrafluoro-4-[(2-phenylethyl)sulfonyl]benzenesulfonamide;
2,3,5,6-tetrafluoro-4-morpholin-4-ylbenzenesulfonamide;
2,3,5,6-tetrafluoro-4-[(mesitylmethyl)thio]benzenesulfonamide;
4-[(4,6-dimethylpyrimidin-2-yl)thio]-2,3,5,6-tetrafluorobenzenesulfonamide;
4-(1,3-benzothiazol-2-ylthio)-2,3,5,6-tetrafluorobenzenesulfonamide;
4-(1-adamantylamino)-2,3,5,6-tetrafluorobenzenesulfonamide;
3-{[4-(aminosulfonyl)-2,3,5,6-tetrafluorophenyl]thio}-[1,2,3]thiadiazolo[3,4-a]benzimidazole;
4-[(4,5-diphenyl-1H-imidazol-2-yl)thio]-2,3,5,6-tetrafluorobenzenesulfonamide;
2-(isopropylamino)-3,5,6-trifluoro-4-[(2-phenylethyl)thio]benzenesulfonamide;
2-(benzylamino)-3,5,6-trifluoro-4-[(2-phenylethyl)thio]benzenesulfonamide;
2-[(2-phenylethyl)amino]-3,5,6-trifluoro-4-[(2-phenylethyl)thio]benzenesulfonamide;
2-[(1-phenylethyl)amino]-3,5,6-trifluoro-4-[(2-phenylethyl)thio]benzenesulfonamide;
2-morpholin-4-yl-3,5,6-trifluoro-4-[(2-phenylethyl)thio]benzenesulfonamide;
2-(cyclohexylamino)-3,5,6-trifluoro-4-[(2-phenylethyl)thio]benzenesulfonamide;
2-(cycloheptylamino)-3,5,6-trifluoro-4-[(2-phenylethyl)thio]benzenesulfonamide;
2-(cyclooctylamino)-3,5,6-trifluoro-4-[(2-phenylethyl)thio]benzenesulfonamide;
2-(cyclododecylamino)-3,5,6-trifluoro-4-[(2-phenylethyl)thio]benzenesulfonamide;
2-[(2,6-dimethoxybenzyl)amino]-3,5,6-trifluoro-4-[(2-phenylethyl)thio]benzenesulfonamide;
2-[(3,4-dimethoxybenzyl)amino]-3,5,6-trifluoro-4-[(2-phenylethyl)thio]benzenesulfonamide;
2-(2,3-dihydro-1H-inden-2-ylamino)-3,5,6-trifluoro-4-[(2-phenylethyl)thio]benzenesulfonamide;
2-[(1S)-2,3-dihydro-1H-inden-1-ylamino]-3,5,6-trifluoro-4-[(2-phenylethyl)thio]benzenesulfonamide;
2-[(1S)-1,2,3,4-tetrahydronapthalen-1-ylamino]-3,5,6-trifluoro-4-[(2-phenylethyl)thio]benzenesulfonamide;
2-{[(1S,2R)-2-hydroxy-1,2-diphenylethyl]amino}-3,5,6-trifluoro-4-[(2-phenylethyl)thio]benzenesulfonamide;
2-(cyclooctylamino)-3,5,6-trifluoro-4-[(2-hydroxyethyl)thio]benzenesulfonamide;
2-(cyclododecylamino)-3,5,6-trifluoro-4-[(2-hydroxyethyl)thio]benzenesulfonamide;
2-[(2,6-dimethoxybenzyl)amino]-3,5,6-trifluoro-4-[(2-hydroxyethyl)thio]benzenesulfonamide;
2-[(3,4-dimethoxybenzyl)amino]-3,5,6-trifluoro-4-[(2-hydroxyethyl)thio]benzenesulfonamide;
2-[(1S)-2,3-dihydro-1H-inden-1-ylamino]-3,5,6-trifluoro-4-[(2-hydroxyethyl)thio]benzenesulfonamide;
2-[(1S)-1,2,3,4-tetrahydronapthalen-1-ylamino]-3,5,6-trifluoro-4-[(2-hydroxyethyl)thio]benzenesulfonamide;
2-{[(1S,2R)-2-hydroxy-1,2-diphenylethyl]amino}-3,5,6-trifluoro-4-[(2-hydroxyethyl)thio]benzenesulfonamide;
2-(cyclooctylamino)-3,5,6-trifluoro-4-(propylthio)benzenesulfonamide;
2-(cyclooctylamino)-3,5,6-trifluoro-4-{[2-(4-hydroxyphenyl)ethyl]amino}benzenesulfonamide;
2-(cyclooctylamino)-3,5,6-trifluorobenzenesulfonamide;
2-(cyclododecylamino)-3,5,6-trifluorobenzenesulfonamide;
2-[(2,6-dimethoxybenzyl)amino]-3,5,6-trifluorobenzenesulfonamide;
2-[(3,4-dimethoxybenzyl)amino]-3,5,6-trifluorobenzenesulfonamide;
2-[(1S)-2,3-dihydro-1H-inden-1-ylamino]-3,5,6-trifluorobenzenesulfonamide;
2-[(1S)-1,2,3,4-tetrahydronapthalen-1-ylamino]-3,5,6-trifluorobenzenesulfonamide;
3-(methylamino)-2,5,6-trifluoro-4-[(2-phenylethyl)sulfonyl]benzenesulfonamide;
3-(tert-butyl amino)-2,5,6-trifluoro-4-[(2-phenyl ethyl)sulfonyl]benzenesulfonamide;
3-(benzylamino)-2,5,6-trifluoro-4-[(2-phenylethyl)sulfonyl]benzenesulfonamide;
3-[(2-phenylethyl)amino]-2,5,6-trifluoro-4-[(2-phenylethyl)sulfonyl]benzenesulfonamide;
3-morpholin-4-yl-2,5,6-trifluoro-4-[(2-phenylethyl)sulfonyl]benzenesulfonamide;
3-cyclooctylamino)-2,5,6-trifluoro-4-[(2-phenylethyl)sulfonyl]benzenesulfonamide;
3-(cyclododecylamino)-2,5,6-trifluoro-4-[(2-phenylethyl)sulfonyl]benzenesulfonamide;
3-[(2,6-dimethoxybenzyl)amino]-2,5,6-trifluoro-4-[(2-phenylethyl)sulfonyl]benzenesulfonamide;

3-[(3,4-dimethoxybenzyl)amino]-2,5,6-trifluoro-4-[(2-phenylethyl)sulfonyl]benzenesulfonamide;
3-(1-adamantylamino)-2,5,6-trifluoro-4-[(2-phenylethyl)sulfonyl]benzenesulfonamide;
3-(2,3-dihydro-1H-inden-2-ylamino)-2,5,6-trifluoro-4-[(2-phenylethyl)sulfonyl]benzenesulfonamide;
3-[(1S)-2,3-dihydro-1H-inden-1-ylamino]-2,5,6-trifluoro-4-[(2-phenylethyl)sulfonyl]benzenesulfonamide;
3-[(1S)-1,2,3,4-tetrahydronapthalen-1-ylamino)-2,5,6-trifluoro-4-[(2-phenylethyl)sulfonyl]benzenesulfonamide;
3-{[(1S,2R)-2-hydroxy-1,2-diphenylethyl]amino}-2,5,6-trifluoro-4-[(2-phenylethyl)sulfonyl]benzenesulfonamide;
3-{[(1R,2S)-2-hydroxy-1,2-diphenylethyl]amino}-2,5,6-trifluoro-4-[(2-phenylethyl)sulfonyl]benzenesulfonamide;
3-(benzylamino)-2,5,6-trifluoro-4-[(2-hydroxyethyl)sulfonyl]benzenesulfonamide;
3-(cyclooctylamino)-2,5,6-trifluoro-4-[(2-hydroxyethyl)sulfonyl]benzenesulfonamide;
3-(cyclododecylamino)-2,5,6-trifluoro-4-[(2-hydroxyethyl)sulfonyl]benzenesulfonamide;
3-[(2,6-dimethoxybenzyl)amino]-2,5,6-trifluoro-4-[(2-hydroxyethyl)sulfonyl]benzenesulfonamide;
3-[(3,4-dimethoxybenzyl)amino]-2,5,6-trifluoro-4-[(2-hydroxyethyl)sulfonyl]benzenesulfonamide;
3-[(1S)-2,3-dihydro-1H-inden-1-ylamino]-2,5,6-trifluoro-4-[(2-hydroxyethyl) sulfonyl]benzenesulfonamide;
3-[(1S)-1,2,3,4-tetrahydronapthalen-1-ylamino)-2,5,6-trifluoro-4-[(2-hydroxyethyl)sulfonyl]benzenesulfonamide;
3-{[(1S,2R)-2-hydroxy-1,2-diphenylethyl]amino}-2,5,6-trifluoro-4-[(2-hydroxyethyl)sulfonyl]benzenesulfonamide;
3,5-bis(cyclooctylamino)-2,6-difluoro-4-[(2-phenylethyl)sulfonyl]benzenesulfonamide;
3,5-bis[(3,4-dimethoxybenzyl)amino]-2,6-difluoro-4-[(2-hydroxyethyl)sulfonyl]benzenesulfonamide;

Demonstration, that all above listed compounds exhibit CA inhibitor properties.

The starting materials used are products that are known or that are prepared according to known operating procedures.

The structures of the compounds described in the Examples were determined according to the usual spectrophotometric techniques (infrared, NMR, mass spectrometry).

DETAILED DESCRIPTION OF THE INVENTION

Abbreviations Used in the Text

AZM—acetazolamide,
CA—carbonic anhydrase,
DMSO—dimethyl sulfoxide,
Et$_3$N—triethylamine,
EZA—ethoxzolamide,
HRMS—high-resolution mass spectrometry,
ITC—isothermal titration calorimetry,
K$_d$—dissociation constant,
NMR—nuclear magnetic resonance,
Ph—phenyl,
TSA—fluorescent thermal shift assay.

New compounds of the invention are obtained according to general synthesis schemes A-J.

Scheme A.

Synthesis of 4-substituted-2,3,5,6-tetrafluorobenzenesulfonamides (compounds 2a-x). Sulfonamides 2a, c, f-j, l-p, r-x were obtained from compound 1 by using appropriate nucleophile in ethanol, methanol or DMSO in the presence of Et$_3$N or K$_2$CO$_3$ (excess of nucleophile was used in several cases instead of mentioned bases). The compounds 2d, e were prepared by oxidation of 2c with CH$_3$COOH\H$_2$O$_2$. Oxidation of the compounds 2j, p with CrO$_3$ gave 2k, q. The reaction of 2a with benzaldehyde leaded to formation of 2b.

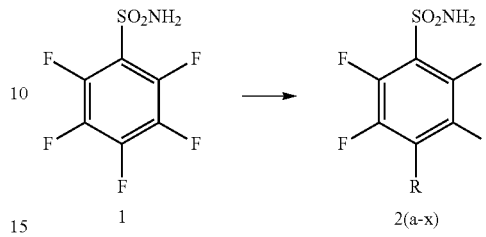

R = NHNH$_2$(a), NHN═CHPh(b), SCH$_2$CH$_2$OH (c), SO$_2$CH$_2$CH$_2$OH(d), SO$_2$CH$_2$CH$_2$OCOCH$_3$(e), SCH$_2$CH$_2$CH$_3$(f), SCH$_2$COOH(g), SCH$_2$CH$_2$COOH(h), NH(CH$_2$)$_5$COOH (i), SPh(j), SO$_2$Ph(k), OPh(l), SCH$_2$Ph(m), NHCH$_2$Ph(n), NHCH$_2$CH$_2$PhpOH(o), SCH$_2$CH$_2$Ph(p), SO$_2$CH$_2$CH$_2$Ph(q),

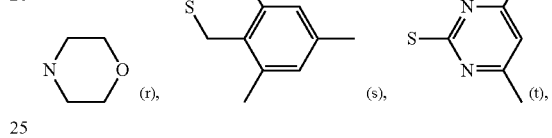

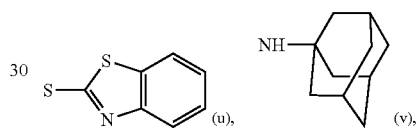

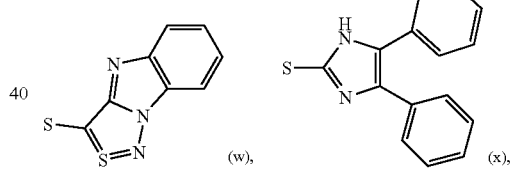

Scheme B.

Synthesis of 2-substituted-3,5,6-trifluoro-4-[(2-phenylethyl)thio]benzenesulfonamides (compounds 3a-o). Sulfonamides 3a-o were obtained from compound 2p by using appropriate nucleophile in DMSO in the presence of Et$_3$N.

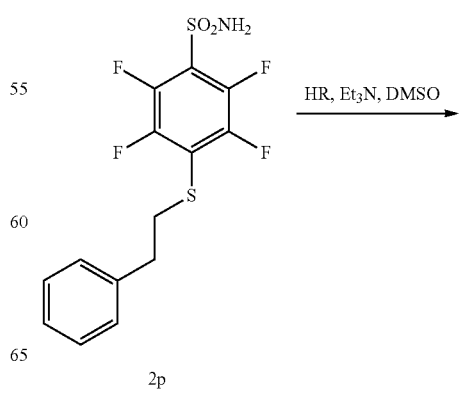

2p

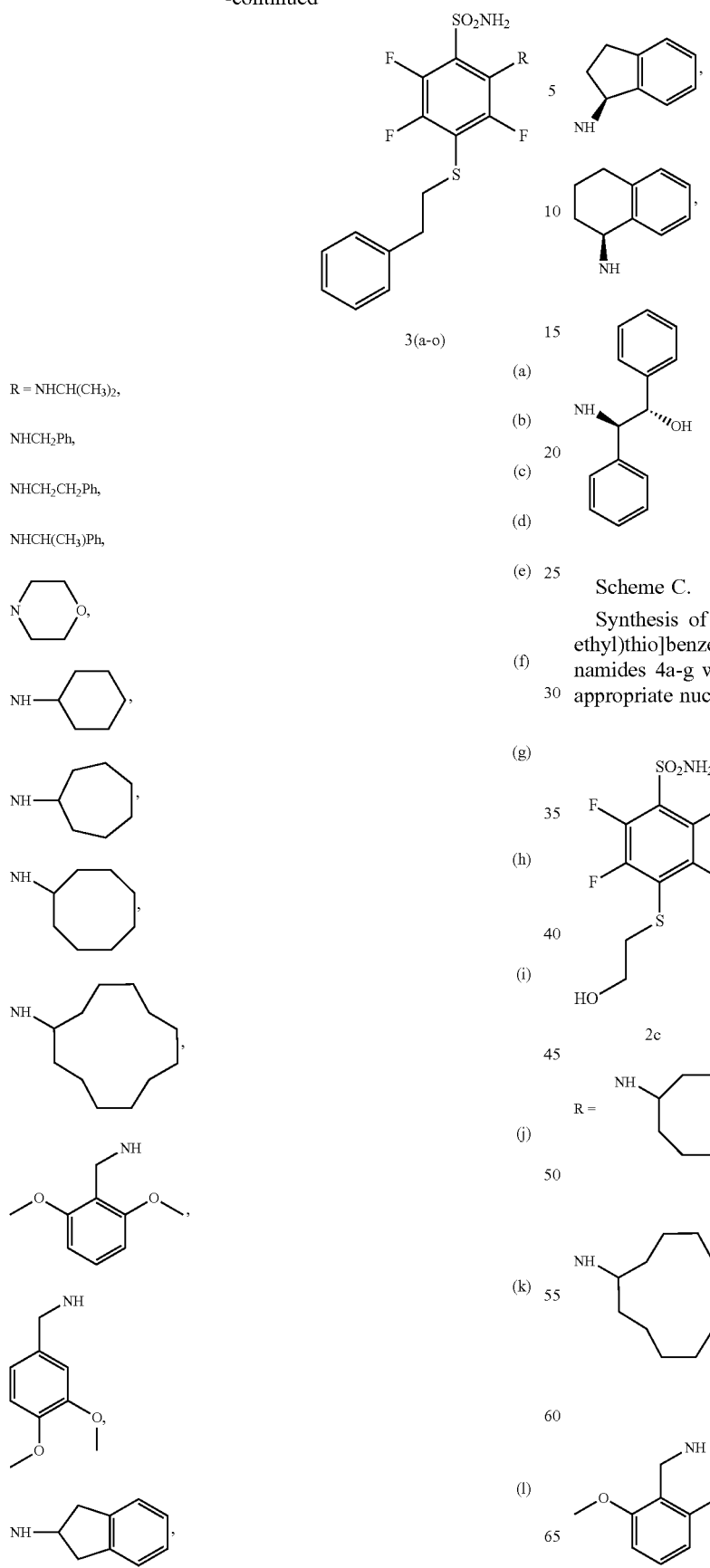
Scheme C.
Synthesis of 2-substituted-3,5,6-trifluoro-4-[(2-hydroxyethyl)thio]benzenesulfonamides (compounds 4a-g). Sulfonamides 4a-g were obtained from compound 2c by using appropriate nucleophile in DMSO in the presence of Et₃N.

-continued

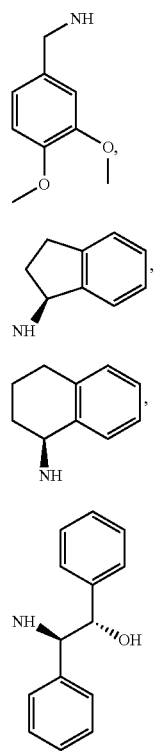

(d)

(e)

(f)

(g)

Scheme D.

Synthesis of 2-(cyclooctylamino)-3,5,6-trifluoro-4-(propylthio)benzenesulfonamide (compound 5). The compound 5 was obtained from compound 2f by using cyclooctylamine in DMSO in the presence of Et₃N.

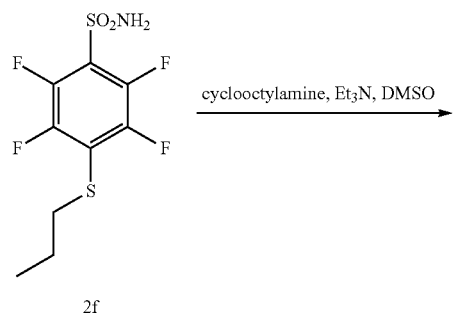

Scheme E.

Synthesis of 2-(cyclooctylamino)-3,5,6-trifluoro-4-{[2-(4-hydroxyphenyl)ethyl]amino}benzensulfonamide (compound 6). The compound 6 was obtained from compound 2o by using cyclooctylamine in DMSO in the presence of Et₃N.

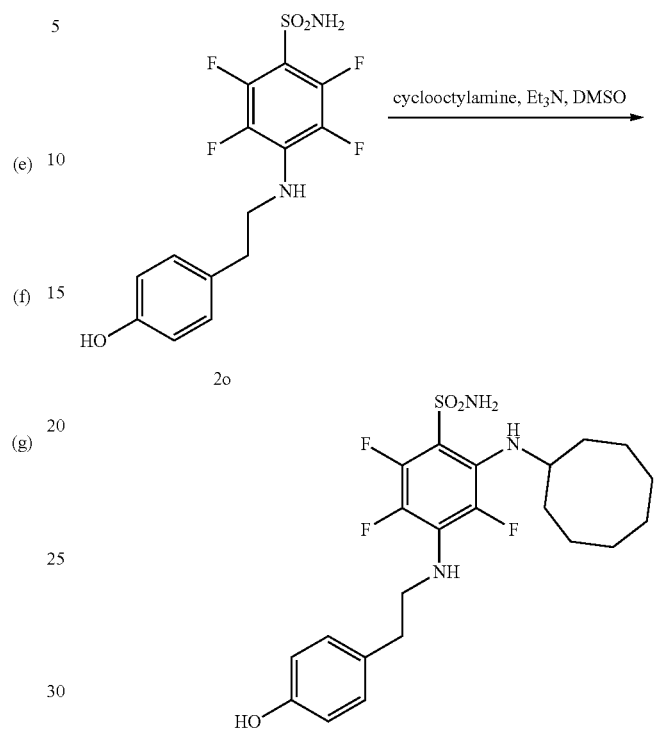

Scheme F.

Synthesis of 2-substituted-3,5,6-trifluorobenzensulfonamides (compounds 8a-f). Sulfonamides 8a-f were obtained from compound 7 by using appropriate nucleophile in DMSO in the presence of Et₃N.

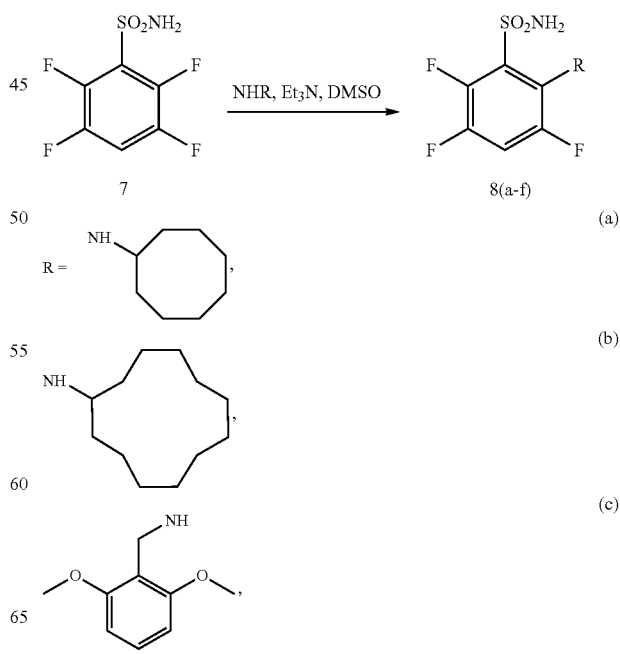

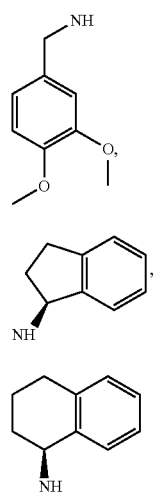

Scheme G.

Synthesis of 3-substituted-2,5,6-trifluoro-4-[(2-phenyl-ethyl)sulfonyl]benzenesulfonamides (compounds 9a-o). Sulfonamides 9d, f-o were obtained from compound 2q by using appropriate nucleophile in DMSO in presence of Et₃N. The compound 9a was synthesized using excess of methylamine in MeOH. The compound 9c was synthesized in MeOH in presence of Et₃N. Fluorinated derivatives 9b, 9e were obtained by using 2 eq of nucleophile in DMSO.

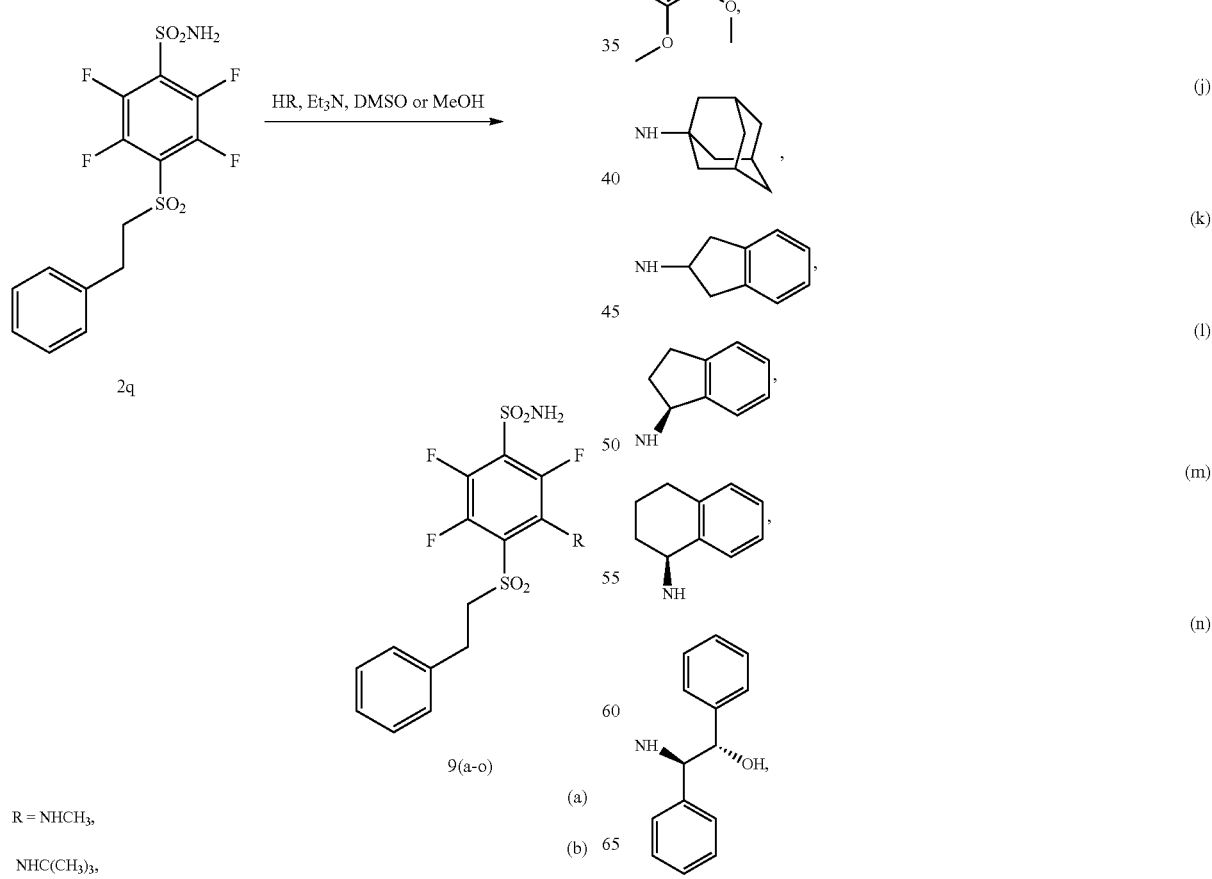

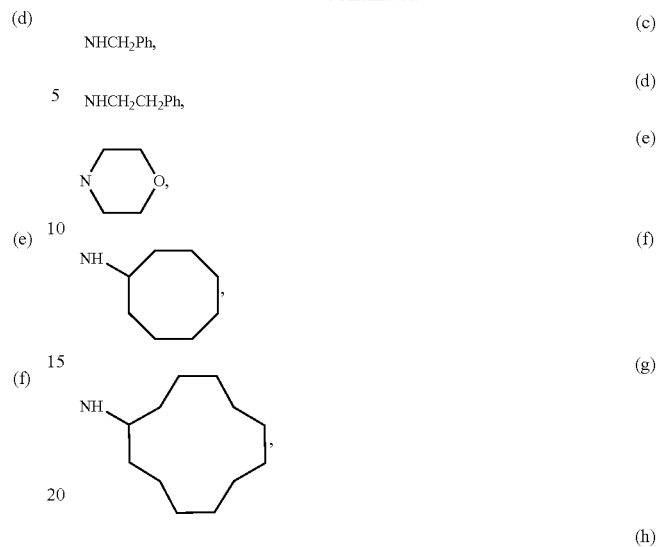

(o)
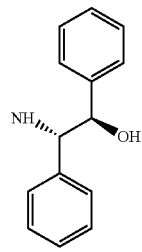

Scheme H.

Synthesis of 3-substituted-2,5,6-trifluoro-4-[(2-hydroxyethyl)sulfonyl]benzenesulfonamides (compounds 10a-h). Sulfonamides 10c-h were obtained from compound 2d by using 2 eq of appropriate nucleophile in DMSO. The compounds 10a, b were synthesized in MeOH.

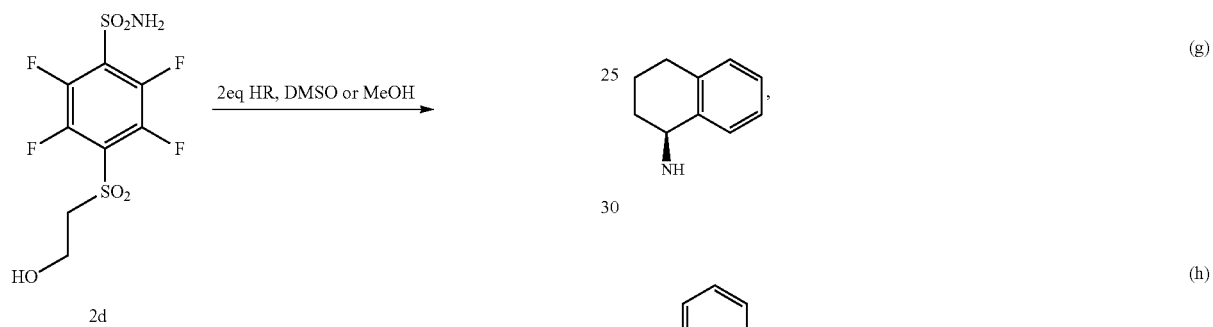

2d

(e)

(f)

(g)

(h)

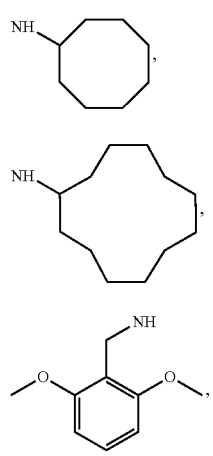

R = NHCH₂Ph,

10(a-h)

(a)

(b)

(c)

(d)

Scheme I.

Synthesis of 3,5-bis(cyclooctylamino)-2,6-difluoro-4-[(2-phenylethyl)sulfonyl]benzenesulfonamide (compound 11). The compound 11 was obtained from compound 2q by using 2 eq of cyclooctylamine in DMSO in the presence of Et₃N.

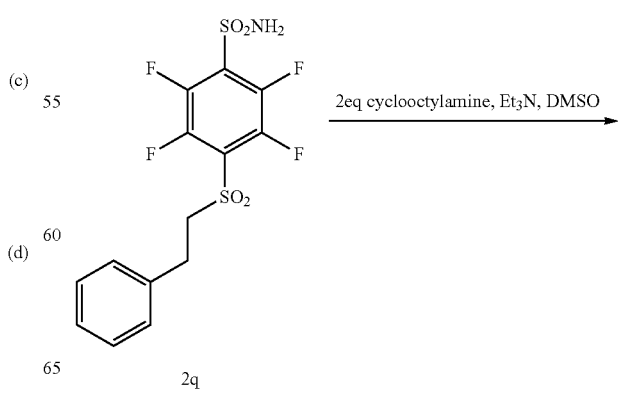

2q

-continued

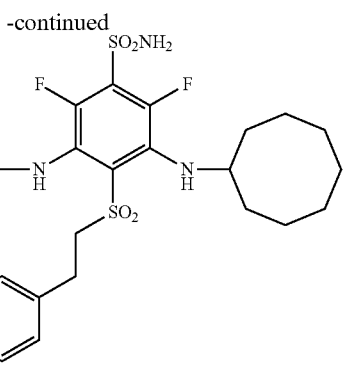

11

Scheme J.

Synthesis of 3,5-bis[(3,4-dimetoxybenzyl)amino-2,6-difluoro-4-[(2-hydroxyethyl)sulfonyl]benzenesulfonamide (compound 12). The compound 12 was obtained from compound 2d by using 4 eq of 3,4-dimethoxybenzylamine in DMSO.

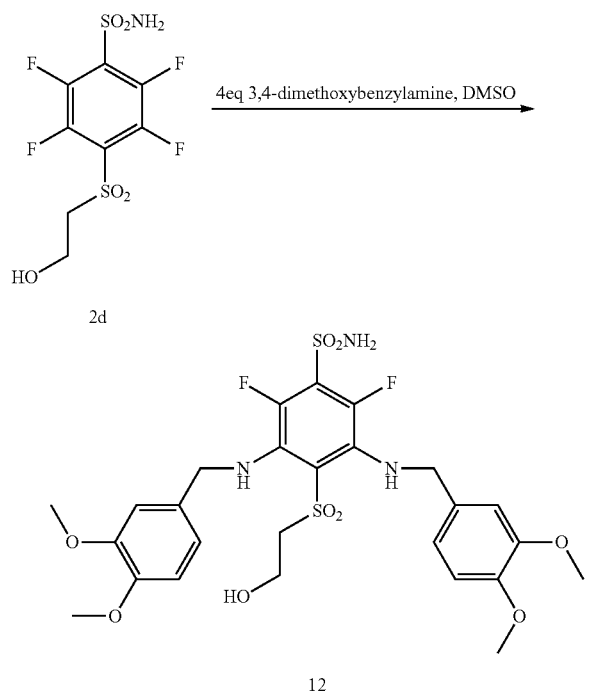

Embodiments of the Invention

Represented below are specific examples of invention compounds synthesis. These examples are presented only for illustrative purpose of the invention; they do not limit the scope of the invention.

Example 1. Preparation of 2,3,5,6-tetrafluoro-4-hydrazinobenzenesulfonamide (Compound 2a)

The mixture of pentafluorobenzenesulfonamide (compound 1) (0.32 g, 1.295 mmol), $NH_2NH_2 \times H_2O$ (0.126 mL, 2.59 mmol), and EtOH (10 mL) was stirred at ambient temperature for 24 h. EtOH was evaporated in vacuum and the resultant precipitate was filtered, washed with $H_2O$. Recrystallization was accomplished from $H_2O$. Yield: 0.2 g, 60%, decomp. at 160-161° C.

$^1$H NMR (300 MHz, DMSO-$D_6$): 4.68 (2H, s, $NH_2$), 7.75 (1H, s, NH), 7.98 (2H, s, $SO_2NH_2$).

$^{13}$C NMR (75 MHz, DMSO-$D_6$): 108.6 (C1, t, J($^{19}$F—$^{13}$C)=14 Hz), 135 (C4, t, J($^{19}$F—$^{13}$C)=16 Hz), 136 (C3, C5, d, J($^{19}$F—$^{13}$C)=240 Hz), 144.1 (C2, C6, d, J($^{19}$F—$^{13}$C)=240 Hz).

$^{19}$F NMR (282 MHz, DMSO-$D_6$): −143.05 (2F, d, J=15.8 Hz), −160.15 (2F, d, J=17.2 Hz).

HRMS calcd. for $C_6H_5F_4N_3O_2S$ [(M+H)$^+$]: 335.9782. found: 335.9780.

Example 2. Preparation of 4-(2-benzylidenehydrazino)-2,3,5,6-tetrafluorobenzenesulfonamide (Compound 2b)

The mixture of 2,3,5,6-tetrafluoro-4-hydrazinobenzenesulfonamide (compound 2a) (0.13 g, 0.5 mmol), benzaldehyde (0.051 mL, 0.5 mmol), and MeOH (10 mL) was stirred at ambient temperature for 4 h. MeOH was evaporated in vacuum. Recrystallization was accomplished from iPrOH. Yield: 0.14 g, 82%, decomp. at 272-273° C.

$^1$H NMR (300 MHz, DMSO-$D_6$): 7.35-7.55 (3H, m, Ph), 7.6-7.75 (2H, m, Ph), 8.12 (1H, s, NH), 8.25 (2H, s, $SO_2NH_2$), 10.96 (1H, s, CH).

$^{13}$C NMR (75 MHz, DMSO-$D_6$): 111.7 (C1, t, J($^{19}$F—$^{13}$C)=14 Hz), 127.1 (Ph), 128.5 (C4, t, J($^{19}$F—$^{13}$C)=13 Hz), 129.5 (Ph), 130.1 (Ph), 135.1 (Ph), 136.3 (C3, C5, d, J($^{19}$F—$^{13}$C)=244 Hz), 144.7 (CH), 144.5 (C2, C6, d, J($^{19}$F—$^{13}$C)=251 Hz).

$^{19}$F NMR (282 MHz, DMSO-$D_6$): −141.6 (2F, d, J=16.4 Hz), −156.6 (2F, d, J=18 Hz).

HRMS calcd. for $C_{13}H_9F_4N_3O_2S$ [(M+H)$^+$]: 348.0424. found: 348.0433.

Example 3. Preparation of 2,3,5,6-tetrafluoro-4[(2-hydroxyethyl)sulfonyl]benzenesulfonamide (Compound 2d)

The mixture of 2,3,5,6-tetrafluoro-4[(2-hydroxyethyl)thio]benzenesulfonamide (compound 2c) (0.1 g, 0.33 mmol), $CH_3COOH$ (2 mL), $H_2O$ (1 mL) was heated at 70° C. for 22 h. $H_2O_2$ was added by portions (0.2 mL) every 4 h (overall amount 1 mL). The progress of reaction was monitored by TLC. The solvent was then removed in vacuum and crude product was purified by crystallization from $H_2O$. Yield: 0.067 g, 61%, mp 139-140° C.

$^1$H NMR (300 MHz, DMSO-$D_6$): 3.75 (2H, t, J=5.4 Hz, $SO_2CH_2CH_2$), 3.86 (2H, t, J=5.4 Hz, $SO_2CH_2CH_2$), 5.01 (1H, br s, OH), 8.65 (2H, s, $SO_2NH_2$).

$^{13}$C NMR (75 MHz, DMSO-$D_6$): 55.9 ($SO_2CH_2CH_2$), 60.2 ($SO_2CH_2CH_2$), 123.4 (C1 or C4, t, J($^{19}$F—$^{13}$C)=15 Hz), 128 (C1 or C4, t, J($^{19}$F—$^{13}$C)=16 Hz), 143.5 (C3, C5 or C2, C6, dd, $^1$J($^{19}$F—$^{13}$C)=254 Hz, $^2$J($^{19}$F—$^{13}$C)=18 Hz), 145 (C3, C5 or C2, C6, dd, $^1$J($^{19}$F—$^{13}$C)=248 Hz, $^2$J($^{19}$F—$^{13}$C) 15 Hz).

$^{19}$F NMR (282 MHz, DMSO-$D_6$): −136.7 (2F, dd, $^1$J=26 Hz, $^2$J=12 Hz), −137.6 (2F, dd, $^1$J=26 Hz, $^2$J=12 Hz).

HRMS calcd. for $C_8H_7F_4NO_5S_2$ [(M−H)$^-$]: 335.9629. found: 335.9635.

Example 4. Preparation of 2-{[4-(aminosulfonyl)-2,3,5,6-tetrafluorophenyl]sulfonyl}ethyl acetate (Compound 2e)

The mixture of 2,3,5,6-tetrafluoro-4[(2-hydroxyethyl)thio]benzenesulfonamide (compound 2c) (0.1 g, 0.33 mmol), CH$_3$COOH (2 mL) was heated at 70° C. for 24 h. H$_2$O$_2$ was added by portions (0.1 mL) every 8 h (overall amount 0.3 mL). The progress of reaction was monitored by TLC. The solvent was then removed in vacuum and crude product was purified by two times crystallization from H$_2$O. Yield: 0.04 g, 36%, mp 154° C.

$^1$H NMR (300 MHz, DMSO-D$_6$): 1.85 (3H, s, CH$_3$), 4.04 (2H, t, J=5.4 Hz, SO$_2$CH$_2$CH$_2$), 4.43 (2H, t, J=5.4 Hz, SO$_2$CH$_2$CH$_2$), 8.7 (2H, s, SO$_2$NH$_2$).

$^{13}$C NMR (75 MHz, DMSO-D$_6$): 20.8 (CH$_3$), 56.6 (SO$_2$CH$_2$CH$_2$), 58 (SO$_2$CH$_2$CH$_2$), 122 (C1 or C4, t, J($^{19}$F—$^{13}$C)=14 Hz), 128.6 (C1 or C4, t, J($^{19}$F—$^{13}$C)=16 Hz), 143.7 (C3, C5 or C2, C6, d, J($^{19}$F—$^{13}$C)=255 Hz), 145 (C3, C5 or C2, C6, d, J($^{19}$F—$^{13}$C)=248 Hz), 170.2 (C=O).

$^{19}$F NMR (282 MHz, DMSO-D$_6$): −136.2 (2F, dd, $^1$J=26 Hz, $^2$J=12 Hz), −137.1 (2F, dd, $^1$J=26 Hz, $^2$J=12 Hz).

HRMS calcd. for C$_{10}$H$_9$F$_4$NO$_6$S$_2$ [(M−H)$^-$]: 377.9735. found: 377.9737.

Example 5. Preparation of 2,3,5,6-tetrafluoro-4-[(2-hydroxyethyl)thio]benzenesulfonamide (Compound 2c), 2,3,5,6-tetrafluoro-4-(propylthio)benzenesulfonamide (Compound 2f), {[4-(aminosulfonyl)-2,3,5,6-tetrafluorophenyl]thio}acetic acid (Compound 2 g), 3-{[4-(aminosulfonyl)-2,3,5,6-tetrafluorophenyl]thio}propanoic acid (Compound 2 h), 6-{[4-(aminosulfonyl)-2,3,5,6-tetrafluorophenyl]amino}hexanoic acid (Compound 2i), 4-(benzylthio)-2,3,5,6-tetrafluorobenzenesulfonamide (Compound 2m), 4-(benzylamino)-2,3,5,6-tetrafluorobenzenesulfonamide (Compound 2n), 2,3,5,6-tetrafluoro-4-{[2-(4-hydroxyphenyl)ethyl]amino}benzenesulfonamide (Compound 2o), 2,3,5,6-tetrafluoro-4-[(2-phenylethyl)thio]benzenesulfonamide (Compound 2p), 2,3,5,6-tetrafluoro-4-[(mesitylmethyl)thio]benzenesulfonamide (Compound 2s), 3-{[4-(aminosulfonyl)-2,3,5,6-tetrafluorophenyl]thio}-[1,2,3]thiadiazolo[3,4-a]benzimidazole (Compound 2w)

The mixture of pentafluorobenzenesulfonamide (compound 1) (0.25 g, 1 mmol), MeOH (10 mL), Et$_3$N (0.141 mL, 1.01 mmol) and appropriate nucleophile (1.1 mmol) was refluxed. The compounds 2c, h, i, n, p, s were obtained after 8 h, the compound 2f was obtained after 10 h, the compounds 2g and 2o were obtained after 15 h, the compound 2m was obtained after 4 h, the compound 2w was obtained after 1 h. MeOH was evaporated in vacuum and the resultant precipitate was filtered, washed with H$_2$O (except 2 g, h, i).

The compound 2c. Recrystallization was accomplished from H$_2$O. Yield: 0.22 g, 71%, mp 111-112° C.

$^1$H NMR (300 MHz, DMSO-D$_6$): 3.16 (2H, t, J=6 Hz, SCH$_2$CH$_2$), 3.6 (2H, k, J=6 Hz, SCH$_2$CH$_2$), 4.97 (1H, t, J=3.6 Hz, OH), 8.43 (2H, s, SO$_2$NH$_2$).

$^{13}$C NMR (75 MHz, DMSO-D$_6$): 37.3 (SCH$_2$CH$_2$), 61.4 (SCH$_2$CH$_2$), 119.95 (C1, t, J($^{19}$F-$^{13}$C)=14 Hz), 122.85 (C4, t, J($^{19}$F—$^{13}$C)=14.9 Hz), 143.2 (C2, C6, ddd, $^1$J($^{19}$F—$^{13}$C)=254 Hz, $^2$J($^{19}$F—$^{13}$C)=17 Hz, $^3$J($^{19}$F—$^{13}$C)=4 Hz), 147 (C3, C5, ddd, $^1$J($^{19}$F—$^{13}$C)=228 Hz, $^2$J($^{19}$F—$^{13}$C)=14 Hz, $^3$J($^{19}$F—$^{13}$C)=4 Hz).

$^{19}$F NMR (282 MHz, DMSO-D$_6$): −133.54 (2F, dd, $^1$J=26.8 Hz, $^2$J=13.8 Hz), −139.97 (2F, dd, $^1$J=26.2 Hz, $^2$J=12.7 Hz).

HRMS calcd. for C$_8$H$_7$F$_4$NO$_3$S$_2$ [(M−H)$^-$]: 303.9731. found: 303.9729.

The compound 2f. Recrystallization was accomplished from EtOH:H$_2$O (2:1). Yield: 0.25 g, 81%, mp 120° C.

$^1$H NMR (300 MHz, DMSO-D$_6$): 0.96 (3H, t, J=7.2 Hz, CH$_3$), 1.55 (2H, sex, J=7.2 Hz, CH$_2$), 3.04 (2H, t, J=7.2 Hz, CH$_2$), 8.41 (2H, s, SO$_2$NH$_2$).

$^{13}$C NMR (75 MHz, DMSO-D$_6$): 13.3 (CH$_3$), 23.5 (CH$_2$), 36.4 (CH$_2$), 119.2 (C1, t, J($^{19}$F-$^{13}$C)=20 Hz), 123.1 (C4, t, J($^{19}$F—$^{13}$C)=16 Hz), 143.2 (C2, C6, dd, $^1$J($^{19}$F—$^{13}$C)=254 Hz, $^2$J($^{19}$F-$^{13}$C)=17 Hz), 147.2 (C3, C5, dd, $^1$J($^{19}$F—$^{13}$C)=244 Hz, $^2$J($^{19}$F—$^{13}$C)=17 Hz).

$^{19}$F NMR (282 MHz, DMSO-D$_6$): −133.9 (2F, dd, $^1$J=25 Hz, $^2$J=11 Hz), −139.6 (2F, dd, $^1$J=25 Hz, $^2$J=14 Hz).

HRMS calcd. for C$_9$H$_9$F$_4$NO$_2$S$_2$ [(M−H)$^-$]: 301.9938. found: 301.9940.

The compound 2 g. The product was purified by chromatography on a column of silica gel (0.04-0.063 mm) with ethyl acetate. Yield: 0.12 g, 38%, mp 158-159° C.

$^1$H NMR (300 MHz, DMSO-D$_6$): 3.9 (2H, s, CH$_2$), 8.44 (2H, s, SO$_2$NH$_2$), 12.8 (1H, br s, COOH).

$^{13}$C NMR (75 MHz, DMSO-D$_6$): 36 (CH$_2$), 118.8 (C1, t, J($^{19}$F—$^{13}$C)=20 Hz), 123.3 (C4, t, J($^{19}$F—$^{13}$C)=16 Hz), 143.1 (C2, C6, dd, $^1$J($^{19}$F—$^{13}$C)=254 Hz, $^2$J($^{19}$F—$^{13}$C)=16 Hz), 147 (C3, C5, d, J($^{19}$F—$^{13}$C)=249 Hz), 170.3 (COOH).

$^{19}$F NMR (282 MHz, DMSO-D$_6$): −133.6 (2F, dd, $^1$J=25 Hz, $^2$J=10 Hz), −139.8 (2F, dd, $^1$J=25 Hz, $^2$J=12 Hz).

HRMS calcd. for C$_8$H$_5$F$_4$NO$_4$S$_2$ [(M−H)$^-$]: 317.9523. found: 317.9525.

The compound 2 h. The product was purified by chromatography on a column of silica gel (0.04-0.063 mm) with ethyl acetate. Yield: 0.2 g, 59%, mp 168-169° C.

$^1$H NMR (300 MHz, DMSO-D$_6$): 2.59 (2H, t, J=6.9 Hz, CH$_2$), 3.21 (2H, t, J=6.6 Hz, CH$_2$), 8.42 (2H, s, SO$_2$NH$_2$), 12.4 (1H, br s, COOH).

$^{13}$C NMR (75 MHz, DMSO-D$_6$): 30.1 (CH$_2$), 35.4 (CH$_2$), 118.8 (C1, t, J($^{19}$F—$^{13}$C)=20 Hz), 123.4 (C4, t, J($^{19}$F—$^{13}$C)=16 Hz), 143.2 (C2, C6, dd, $^1$J($^{19}$F—$^{13}$C)=254 Hz, $^2$J($^{19}$F—$^{13}$C)=17 Hz), 147.3 (C3, C5, dd, $^1$J($^{19}$F—$^{13}$C)=241 Hz, $^2$J($^{19}$F—$^{13}$C)=19 Hz), 173.1 (COOH).

$^{19}$F NMR (282 MHz, DMSO-D$_6$): −133.3 (2F, dd, $^1$J=25 Hz, $^2$J=10 Hz), −139.6 (2F, dd, $^1$J=25 Hz, $^2$J=10 Hz).

HRMS calcd. for C$_9$H$_7$F$_4$NO$_4$S$_2$ [(M−H)$^-$]: 331.968. found: 331.9683.

The compound 2i. The product was purified by chromatography on a column of silica gel (0.04-0.063 mm) with ethyl acetate. Yield: 0.15 g, 42%, mp 142-144° C.

$^1$H NMR (300 MHz, DMSO-D$_6$): 1.2-1.6 (8H, m, (CH$_2$)$_4$), 2.22 (2H, t, J=7.2 Hz, CH$_2$), 6.7 (1H, s, NH), 7.93 (2H, s, SO$_2$NH$_2$), 12.01 (1H, s, COOH).

$^{13}$C NMR (75 MHz, DMSO-D$_6$): 24.9 (CH$_2$), 26.3 (CH$_2$), 30.7 (CH$_2$), 34.3 (CH$_2$), 44.7 (CH$_2$), 108.2 (C1, t, J($^{19}$F—$^{13}$C)=15 Hz), 132 (C4, t, J($^{19}$F—$^{13}$C)=16 Hz), 136.4 (C2, C6, d, J($^{19}$F—$^{13}$C)=238 Hz), 144.7 (C3, C5, d, J($^{19}$F—$^{13}$C)=247 Hz), 175.1 (COOH).

$^{19}$F NMR (282 MHz, DMSO-D$_6$): −142.7 (2F, d, J=16.6 Hz), −161.69 (2F, d, J=18.3 Hz).

HRMS calcd. for C$_{12}$H$_{14}$F$_4$N$_2$O$_4$S [(M−H)$^-$]: 357.0538. found: 357.0542.

The compound 2m. Recrystallization was accomplished from iPrOH. Yield: 0.23 g, 64%, mp 184° C.

$^1$H NMR (300 MHz, DMSO-D$_6$): 4.3 (2H, s, CH$_2$), 7.1-7.5 (5H, m, ArH), 8.44 (2H, s, SO$_2$NH$_2$).

$^{13}$C NMR (75 MHz, DMSO-D$_6$): 38.6 (CH$_2$), 118.5 (C1, t, J($^{19}$F—$^{13}$C)=21 Hz), 123.6 (C4, t, J($^{19}$F—$^{13}$C)=16 Hz), 128.4 (Ar), 129.3 (Ar), 129.5 (Ar), 137.4 (Ar), 143.1 (C2, C6, dd, $^1$J($^{19}$F-$^{13}$C)=254 Hz, $^2$J($^{19}$F—$^{13}$C)=17 Hz), 147.3 (C3, C5, dd, $^1$J($^{19}$F—$^{13}$C)=248 Hz, $^2$J($^{19}$F—$^{13}$C)=17 Hz).

$^{19}$F NMR (282 MHz, DMSO-D$_6$): −132.8 (2F, dd, $^1$J=27 Hz, $^2$J=11 Hz), −139.8 (2F, dd, $^1$J=26 Hz, $^2$J=10 Hz).

HRMS calcd. for C$_{13}$H$_9$F$_4$NO$_2$S$_2$ [(M−H)$^-$]: 349.9938. found: 349.9940.

The compound 2n. Recrystallization was accomplished from H$_2$O:EtOH (1:1). Yield: 0.21 g, 62%, mp 132-133° C.

$^1$H NMR (300 MHz, DMSO-D$_6$): 4.56 (2H, d, J=6.3 Hz, CH$_2$), 7.2-7.6 (6H, m, NH, ArH), 7.98 (2H, s, SO$_2$NH$_2$).

$^{13}$C NMR (75 MHz, DMSO-D$_6$): 47.9 (CH$_2$), 109 (C1, t, J($^{19}$F—$^{13}$C)=17 Hz), 127.2 (Ar), 127.7 (Ar), 129 (Ar), 131.8 (C4, t, J($^{19}$F—$^{13}$C)=16 Hz), 136.7 (C2, C6, d, J($^{19}$F—$^{13}$C)=240 Hz), 140.5 (Ar), 144.3 (C3, C5, d, J($^{19}$F—$^{13}$C)=241 Hz).

$^{19}$F NMR (282 MHz, DMSO-D$_6$): −142.51 (2F, d, J=18.3 Hz), −160.38 (2F, d, J=18.3 Hz).

HRMS calcd. for C$_{13}$H$_{10}$F$_4$N$_2$O$_2$S [(M+H)$^+$]: 335.0472. found: 335.0472.

The compound 2o. Recrystallization was accomplished from EtOH:H$_2$O (1:2). Yield: 0.25 g, 68%, decomp. at 100° C.

$^1$H NMR (300 MHz, DMSO-D$_6$): 2.74 (2H, t, J=7.8 Hz, CH$_2$), 3.45-3.6 (2H, m, CH$_2$), 6.7 (2H, d, J=8.4 Hz, ArH), 7.01 (2H, d, J=8.4 Hz, ArH), 7.96 (2H, s, SO$_2$NH$_2$), 9.23 (1H, s, NH).

$^{13}$C NMR (75 MHz, DMSO-D$_6$): 36.5 (CH$_2$), 46.8 (CH$_2$), 108.4 (C1, t, J($^{19}$F—$^{13}$C)=16 Hz), 115.9 (Ar), 129.4 (Ar), 130.3 (Ar), 131.9 (C4, t, J($^{19}$F—$^{13}$C)=16 Hz), 136.5 (C2, C6, d, J($^{19}$F—$^{13}$C)=240 Hz), 144.4 (C3, C5, d, J($^{19}$F—$^{13}$C)=240 Hz), 156.5 (Ar).

$^{19}$F NMR (282 MHz, DMSO-D$_6$): −142.6 (2F, d, J=19 Hz), −161.4 (2F, d, J=18 Hz).

HRMS calcd. for C$_{14}$H$_{12}$F$_4$N$_2$O$_3$S [(M−H)$^-$]: 363.0432. found: 363.0435.

The compound 2p. Recrystallization was accomplished from EtOH:H$_2$O (2:1). Yield: 0.24 g, 71%, mp 121° C.

$^1$H NMR (300 MHz, DMSO-D$_6$): 2.91 (2H, t, J=7.2 Hz, SCH$_2$CH$_2$), 3.37 (2H, t, J=7.2 Hz, SCH$_2$CH$_2$), 7.1-7.4 (5H, m, ArH), 8.41 (2H, s, SO$_2$NH$_2$).

$^{13}$C NMR (75 MHz, DMSO-D$_6$): 35.4 (SCH$_2$CH$_2$), 36.6 (SCH$_2$CH$_2$), 119 (C1, t, J($^{19}$F-$^{13}$C)=20 Hz), 122.9 (C4, t, J($^{19}$F—$^{13}$C)=16 Hz), 127.2 (Ar), 128.9 (Ar), 129.3 (Ar), 139.7 (Ar), 143.2 (C2, C6, dd, $^1$J($^{19}$F—$^{13}$C)=257 Hz, $^2$J($^{19}$F—$^{13}$C)=17 Hz), 147 (C3, C5, dd, $^1$J($^{19}$F—$^{13}$C)=249 Hz, $^2$J($^{19}$F—$^{13}$C)=17 Hz).

$^{19}$F NMR (282 MHz, DMSO-D$_6$): −133.45 (2F, dd, $^1$J=26.5 Hz, $^2$J=13.5 Hz), −139.8 (2F, dd, $^1$J=25.6 Hz, $^2$J=10.7 Hz).

HRMS calcd. for C$_{14}$H$_{11}$F$_4$NO$_2$S$_2$ [(M−H)$^-$]: 364.0095. found: 364.0100.

The compound 2s. Recrystallization was accomplished from EtOH. Yield: 0.29 g, 73%, mp 213-214° C.

$^1$H NMR (300 MHz, DMSO-D$_6$): 2.23 (3H, s, CH$_3$), 2.3 (6H, s, CH$_3$), 4.31 (2H, s, CH$_2$), 6.89 (2H, s, ArH), 8.47 (2H, s, SO$_2$NH$_2$).

$^{13}$C NMR (75 MHz, DMSO-D$_6$): 19.6 (CH$_3$), 21.3 (CH$_3$), 34.3 (CH$_2$), 119.2 (C1, t, J($^{19}$F-$^{13}$C)=21 Hz), 123.6 (C4, t, J($^{19}$F—$^{13}$C)=18 Hz), 129.4 (Ar), 129.7 (Ar), 137.8 (Ar), 137.9 (Ar), 143.3 (C2, C6, d, J($^{19}$F—$^{13}$C)=253 Hz), 147.4 (C3, C5, d, J($^{19}$F—$^{13}$C)=243 Hz).

$^{19}$F NMR (282 MHz, DMSO-D$_6$): −133.1 (2F, dd, $^1$J=25 Hz, $^2$J=10 Hz), −139.5 (2F, dd, $^1$J=25 Hz, $^2$J=11 Hz).

HRMS calcd. for C$_{16}$H$_{15}$F$_4$NO$_2$S$_2$ [(M−H)$^-$]: 392.0408. found: 392.0412.

The compound 2w. The obtained compound was washed with MeOH. Yield: 0.13 g, 30%, decomp. at 233-234° C.

$^1$H NMR (300 MHz, DMSO-D$_6$): 7.33 (1H, t, J=7.8 Hz, ArH), 7.57 (1H, t, J=8.4 Hz, ArH), 7.81 (1H, d, J=8.7 Hz, ArH), 8.2 (1H, d, J=8.1 Hz, ArH), 8.55 (2H, s, SO$_2$NH$_2$).

$^{13}$C NMR (75 MHz, DMSO-D$_6$): 118.4 (Ar), 120.2 (C1, t, J($^{19}$F—$^{13}$C)=15 Hz), 125.9 (Ar), 126 (Ar), 127.7 (C4, t, J($^{19}$F—$^{13}$C)=16 Hz), 130 (Ar), 133.2 (Ar), 133.4 (Ar), 148 (C2, C6, d, J($^{19}$F-$^{13}$C)=254 Hz), 152 (C3, C5, d, J($^{19}$F—$^{13}$C)=236 Hz), 158.7 (Ar), 158.8 (Ar).

$^{19}$F NMR (282 MHz, DMSO-D$_6$): −127.24 (2F, dd, $^1$J=25.9 Hz, $^2$J=11.3 Hz), −134 (2F, dd, $^1$J=25.9 Hz, $^2$J=10.7 Hz).

HRMS calcd. for C$_{14}$H$_6$F$_4$N$_4$O$_2$S$_3$ [(M+H)$^+$]: 434.9662. found: 434.9667.

Example 6. Preparation of 2,3,5,6-tetrafluoro-4-(phenylthio)benzenesulfonamide (Compound 2j)

The mixture of pentafluorobenzenesulfonamide (compound 1) (0.28 g, 1.13 mmol), MeOH (10 mL), Et$_3$N (0.158 mL, 1.13 mmol) and HSPh (0.116 mL, 1.13 mmol) was stirred at ambient temperature for 2 h. MeOH was evaporated in vacuum and the resultant precipitate was filtered, washed with H$_2$O. Recrystallization was accomplished from EtOH:H$_2$O (2:1). Yield: 0.28 g, 74%, mp 139° C.

$^1$H NMR (300 MHz, DMSO-D$_6$): 7.2-7.8 (5H, m, ArH), 8.47 (2H, s, SO$_2$NH$_2$).

$^{13}$C NMR (75 MHz, DMSO-D$_6$): 117.7 (C1, t, J($^{19}$F—$^{13}$C)=19.6 Hz), 124.5 (C4, t, J($^{19}$F-$^{13}$C)=16.3 Hz), 128.7 (Ar), 130.3 (Ar), 130.4 (Ar), 132.4 (Ar), 143.5 (C2, C6, ddd, $^1$J($^{19}$F—$^{13}$C)=255 Hz, $^2$J($^{19}$F—$^{13}$C)=17 Hz, $^3$J($^{19}$F—$^{13}$C)=5 Hz), 147.2 (C3, C5, ddd, $^1$J($^{19}$F—$^{13}$C)=240 Hz, $^2$J($^{19}$F—$^{13}$C)=17 Hz, $^3$J($^{19}$F—$^{13}$C)=5 Hz).

$^{19}$F NMR (282 MHz, DMSO-D$_6$): −132.59 (2F, dd, $^1$J=24.5 Hz, $^2$J=11.6 Hz), −138.75 (2F, dd, $^1$J=24.5 Hz, $^2$J=10.4 Hz).

HRMS calcd. for C$_{12}$H$_7$F$_4$NO$_2$S$_2$ [(M−H)$^-$]: 335.9782. found: 335.9780.

Example 7. Preparation of 2,3,5,6-tetrafluoro-4-(phenylsulfonyl)benzenesulfonamide (Compound 2k)

The mixture of 2,3,5,6-tetrafluoro-4-(phenylthio)benzenesulfonamide (compound 2j) (0.2 g, 0.59 mmol), CrO$_3$ (0.18 g, 1.8 mmol), CH$_3$COOH (10 mL), H$_2$O (0.5 mL) was heated at 70° C. for 2 h. The solvent was then removed in vacuum and the resultant precipitate was filtered, washed with H$_2$O. Recrystallization was accomplished from EtOH. Yield: 0.17 g, 77%, mp 266-267° C.

$^1$H NMR (300 MHz, DMSO-D$_6$): 7.77 (2H, t, J=7.8 Hz, ArH), 7.87 (1H, t, J=7.5 Hz, ArH), 8.09 (2H, d, J=7.8 Hz, ArH), 8.59 (2H, s, SO$_2$NH$_2$).

$^{13}$C NMR (75 MHz, DMSO-D$_6$): 123 (C1, C4, t, J($^{19}$F—$^{13}$C)=13 Hz), 128.4 (Ar), 130.7 (Ar), 136.2 (Ar), 140.4 (Ar), 143.8 (C2, C6 or C3, C5, dd, $^1$J($^{19}$F—$^{13}$C)=258 Hz, $^2$J($^{19}$F-$^{13}$C)=18 Hz), 144.4 (C2, C6 or C3, C5, dd, $^1$J($^{19}$F—$^{13}$C)=258 Hz, $^2$J($^{19}$F—$^{13}$C)=18 Hz).

$^{19}$F NMR (282 MHz, DMSO-D$_6$): −136.6 (4F, s).

HRMS calcd. for C$_{12}$H$_7$F$_4$NO$_4$S$_2$ [(M−H)$^-$]: 367.968. found: 367.9684.

Example 8. Preparation of 2,3,5,6-tetrafluoro-4-phenoxybenzenesulfonamide (Compound 2l)

The mixture of pentafluorobenzenesulfonamide (compound 1) (0.2 g, 0.81 mmol), sodium phenoxide trihydrate (0.145 g, 0.85 mmol) and DMSO (1 mL) was stirred at ambient temperature for 4 h. The mixture was then diluted with H$_2$O (20 mL) and the resultant precipitate was filtered, washed with H$_2$O. Recrystallization was accomplished from EtOH:H$_2$O (1:2). Yield: 0.07 g, 27%, mp 164-165° C.

$^1$H NMR (300 MHz, DMSO-D$_6$): 7.0-7.6 (5H, m, ArH), 8.44 (2H, s, SO$_2$NH$_2$).

$^{13}$C NMR (75 MHz, DMSO-D$_6$): 116.4 (Ar), 120.4 (C1, t, J($^{19}$F—$^{13}$C)=14 Hz), 125 (Ar), 130.9 (Ar), 136.3 (C4, t, J($^{19}$F—$^{13}$C)=14 Hz), 141.9 (C3, C5, d, J($^{19}$F—$^{13}$C)=250 Hz), 144.4 (C2, C6, d, J($^{19}$F—$^{13}$C)=256 Hz), 157 (Ar).

$^{19}$F NMR (282 MHz, DMSO-D$_6$): −139.6 (2F, d, J=16 Hz), −154 (2F, d, J=16 Hz).

HRMS calcd. for C$_{12}$H$_7$F$_4$NO$_3$S [(M−H)$^-$]: 320.001. found: 320.0008.

Example 9. Preparation of 2,3,5,6-tetrafluoro-4-[(2-phenylethyl)sulfonyl]benzenesulfonamide (Compound 2q)

The mixture of 2,3,5,6-tetrafluoro-4-[(2-phenylethyl)thio]benzenesulfonamide (2p) (0.1 g, 0.27 mmol), CrO$_3$ (0.082 g, 0.82 mmol), CH$_3$COOH (10 mL), H$_2$O (0.2 mL) was heated at 60° C. for 4 h. The resultant precipitate was filtered, washed with H$_2$O. Yield: 0.07 g, 64%, mp 248-249° C.

$^1$H NMR (300 MHz, DMSO-D$_6$): 3.12 (2H, t, J=7.2 Hz, SO$_2$CH$_2$CH$_2$), 3.97 (2H, t, J=7.8 Hz, SO$_2$CH$_2$CH$_2$), 7.1-7.4 (5H, m, ArH), 8.66 (2H, s, SO$_2$NH$_2$).

$^{13}$C NMR (75 MHz, DMSO-D$_6$): 28.6 (SO$_2$CH$_2$CH$_2$), 58 (SO$_2$CH$_2$CH$_2$), 121.5 (C1 or C4, t, J($^{19}$F—$^{13}$C)=15 Hz), 127.5 (Ar), 128.2 (C1 or C4, t, J($^{19}$F—$^{13}$C)=16 Hz), 128.9 (Ar), 129.2 (Ar), 137.4 (Ar), 143.5 (C2, C6 or C3, C5, dd, $^1$J($^{19}$F—$^{13}$C)=258 Hz, $^2$J($^{19}$F—$^{13}$C)=17 Hz), 144.8 (C2, C6 or C3, C5, dd, $^1$J($^{19}$F—$^{13}$C)=255 Hz, $^2$J($^{19}$F—$^{13}$C)=17 Hz).

$^{19}$F NMR (282 MHz, DMSO-D$_6$): −136 (2F, dd, $^1$J=25 Hz, $^2$J=12 Hz), −137.1 (2F, dd, $^1$J=25 Hz, $^2$J=12 Hz).

HRMS calcd. for C$_{14}$H$_{11}$F$_4$NO$_4$S$_2$ [(M−H)$^-$]: 395.9993. found: 395.9996.

Example 10. Preparation of 2,3,5,6-tetrafluoro-4-morpholin-4-ylbenzenesulfonamide (Compound 2r)

The mixture of pentafluorobenzenesulfonamide (compound 1) (0.2 g, 0.809 mmol), MeOH (10 mL), morpholine (0.141 mL, 1.62 mmol) was refluxed for 8 h. MeOH was evaporated in vacuum and the resultant precipitate was filtered, washed with H$_2$O. Recrystallization was accomplished from EtOH:H$_2$O (1:1). Yield: 0.13 g, 52%, mp 233-234° C.

$^1$H NMR (300 MHz, DMSO-D$_6$): 3.32 (4H, br s, 2CH$_2$), 3.7 (4H, br s, 2CH$_2$), 8.2 (2H, s, SO$_2$NH$_2$).

$^{13}$C NMR (75 MHz, DMSO-D$_6$): 51.2 (N(CH$_2$)$_2$, t, J($^{19}$F—$^{13}$C)=3.6 Hz), 67.2 (O(CH$_2$)$_2$), 115.4 (C1, t, J($^{19}$F—$^{13}$C)=19 Hz), 133.3 (C4, t, J($^{19}$F—$^{13}$C)=16 Hz), 144.7 (C3, C5, d, J($^{19}$F—$^{13}$C)=256 Hz), 146.3 (C2, C6, d, J($^{19}$F—$^{13}$C)=244 Hz).

$^{19}$F NMR (282 MHz, DMSO-D$_6$): −141.6 (2F, d, J=15.8 Hz), −151.2 (2F, d, J=16.6 Hz).

HRMS calcd. for C$_{10}$H$_{10}$F$_4$N$_2$O$_3$S [(M+H)$^+$]: 315.0421. found: 315.0426.

Example 11. Preparation of 4-[(4,6-dimethylpyrimidin-2-yl)thio]-2,3,5,6-tetrafluorobenzenesulfonamide (2t), 4-(1,3-benzothiazol-2-ylthio)-2,3,5,6-tetrafluorobenzenesulfonamide (2u), 4-[(4,5-diphenyl-1H-imidazol-2-yl)thio]-2,3,5,6-tetrafluorobenzenesulfonamide (2x)

The mixture of pentafluorobenzenesulfonamide (compound 1) (0.1 g, 0.404 mmol), K$_2$CO$_3$ (0.056 g, 0.406 mmol), DMSO (2 mL) and appropriate nucleophile (0.404 mmol) was stirred at ambient temperature for 5 h. The mixture was then diluted with H$_2$O (20 mL) and extracted with EtAc (2×10 mL). The combined organic phase was dried over Na$_2$SO$_4$ and evaporated in vacuum.

The compound 2t. Recrystallization was accomplished from EtOH:H$_2$O (2:1). Yield: 0.12 g, 80%, mp 131-132° C.

$^1$H NMR (300 MHz, DMSO-D$_6$): 2.34 (6H, s, 2CH$_3$), 7.15 (1H, s, ArH), 8.58 (2H, s, SO$_2$NH$_2$).

$^{13}$C NMR (75 MHz, DMSO-D$_6$): 24 (CH$_3$), 114.1 (C1, t, J($^{19}$F—$^{13}$C)=20 Hz), 118.5 (Ar), 125.5 (C4, t, J($^{19}$F—$^{13}$C)=14 Hz), 143.3 (C2, C6, d, J($^{19}$F—$^{13}$C)=255 Hz), 147.7 (C3, C5, d, J($^{19}$F-$^{13}$C)=248 Hz), 166.3 (Ar), 169 (Ar).

$^{19}$F NMR (282 MHz, DMSO-D$_6$): −130.65 (2F, dd, $^1$J=25.4 Hz, $^2$J=10.7 Hz), −139.25 (2F, dd, $^1$J=26.2 Hz, $^2$J=11 Hz).

HRMS calcd. for C$_{12}$H$_9$F$_4$N$_3$O$_2$S$_2$ [(M+H)$^+$]: 368.0145. found: 368.0142.

The compound 2u. Recrystallization was accomplished from EtOH:H$_2$O (2:1). Yield: 0.11 g, 69%, mp 171° C.

$^1$H NMR (300 MHz, DMSO-D$_6$): 7.44 (1H, t, J=8.1 Hz, ArH), 7.51 (1H, t, J=8.1 Hz, ArH), 7.9 (1H, d, J=7.5 Hz, ArH), 8.06 (1H, d, J=8.4 Hz, ArH), 8.65 (2H, s, SO$_2$NH$_2$).

$^{13}$C NMR (75 MHz, DMSO-D$_6$): 113.8 (C1, t, J($^{19}$F—$^{13}$C)=20 Hz), 122.7 (Ar), 122.9 (Ar), 126.2 (Ar), 126.5 (C4, t, J($^{19}$F—$^{13}$C)=16 Hz), 127.5 (Ar), 136 (Ar), 143.5 (C2, C6, dd, $^1$J($^{19}$F—$^{13}$C)=254 Hz, $^2$J($^{19}$F—$^{13}$C)=12 Hz), 147.6 (C3, C5, dd, $^1$J($^{19}$F—$^{13}$C)=250 Hz, $^2$J($^{19}$F—$^{13}$C)=16 Hz), 153.1 (Ar), 162.4 (Ar).

$^{19}$F NMR (282 MHz, DMSO-D$_6$): −130.52 (2F, dd, $^1$J=24.8 Hz, $^2$J=11.6 Hz), −137.87 (2F, dd, $^1$J=24.8 Hz, $^2$J=11.6 Hz).

HRMS calcd. for C$_{13}$H$_6$F$_4$N$_2$O$_2$S$_3$ [(M−H)$^-$]: 392.9455. found: 392.9457.

The compound 2x. Recrystallization was accomplished from EtOH:H$_2$O (2:1). Yield: 0.12 g, 63%, mp 221-122° C.

$^1$H NMR (300 MHz, DMSO-D$_6$): 7.2-7.5 (10H, m, ArH), 8.51 (2H, s, SO$_2$NH$_2$), 13.2 (1H, br s, NH).

$^{13}$C NMR (75 MHz, DMSO-D$_6$): 116 (C1, t, J($^{19}$F—$^{13}$C)=15 Hz), 124.1 (C4, t, J($^{19}$F—$^{13}$C)=16 Hz), 128.3 (br s, Ar), 129.3 (br s, Ar), 133.9 (Ar), 143.3 (C2, C6, d, J($^{19}$F—$^{13}$C)=253 Hz), 146.7 (C3, C5, d, J($^{19}$F—$^{13}$C)=250 Hz).

$^{13}$C NMR (75 MHz, DMSO-D$_6$, CF$_3$COOH): 115.1 (C1, t, J($^{19}$F—$^{13}$C)=15 Hz), 125 (C4, t, J($^{19}$F—$^{13}$C)=16 Hz), 128.6 (Ar), 129.3 (Ar), 129.5 (Ar), 130.2 (Ar), 133.4 (Ar), 134.2 (Ar), 143.5 (C2, C6, d, J($^{19}$F—$^{13}$C)=255 Hz), 146.9 (C3, C5, d, J($^{19}$F—$^{13}$C)=255 Hz).

$^{19}$F NMR (282 MHz, DMSO-D$_6$): −133.53 (2F, dd, J=24.8 Hz, J=10.2 Hz), −139.13 (2F, dd, J=24.8 Hz, J=10.2 Hz).

HRMS calcd. for C$_{21}$H$_{13}$F$_4$N$_3$O$_2$S$_2$ [(M+H)$^+$]: 480.0458. found: 480.0449.

Example 12. Preparation of 4-(1-adamantylamino)-2,3,5,6-tetrafluorobenzenesulfonamide (Compound 2v)

The mixture of pentafluorobenzenesulfonamide (compound 1) (0.2 g, 0.81 mmol), Et$_3$N (0.226 mL, 1.62 mmol), adamantanamine hydrochloride (0.15 g, 0.81 mmol) and DMSO (2 mL) was stirred at ambient temperature for 48 h. The mixture was then diluted with H$_2$O (20 mL) and extracted with EtAc (2×10 mL). The combined organic phase was dried over Na$_2$SO$_4$ and evaporated in vacuum. The product was purified by chromatography on a column of silica gel (0.04-0.063 mm) with EtAc:CHCl$_3$ (1:4), R$_f$=0.63. Yield: 0.04 g, 12%, mp 122-123° C.

$^1$H NMR (300 MHz, CDCl$_3$): 1.6-1.8 (6H, m, adamantane), 1.8-2 (6H, m, adamantane), 2.1-2.25 (3H, m, adamantane), 4.05 (1H, s, NH), 5.59 (2H, s, SO$_2$NH$_2$).

$^{13}$C NMR (75 MHz, CDCl$_3$): 30.1 (adamantane), 36.1 (adamantane), 43.6 (adamantane), 54.8 (adamantane), 110.2 (C1), 130.4 (C4, t, J($^{19}$F—$^{13}$C)=14 Hz), 138 (C2, C6, d, J($^{19}$F—$^{13}$C)=248 Hz), 144.5 (C3, C5, d, J($^{19}$F—$^{13}$C)=251 Hz).

$^{19}$F NMR (282 MHz, CDCl$_3$): −141.53 (2F, d, J=16 Hz), −152.4 (2F, d, J=17.5 Hz).

HRMS calcd. for C$_{16}$H$_{18}$F$_4$N$_2$O$_2$S [(M−H)$^-$]: 377.0952. found: 377.0952.

Example 13. Preparation of 2-(isopropylamino)-3,5,6-trifluoro-4-[(2-phenylethyl)thio]benzenesulfonamide (Compound 3a), 2-(benzylamino)-3,5,6-trifluoro-4-[(2-phenylethyl)thio]benzenesulfonamide (Compound 3b), 2-[(2-phenylethyl)amino]-3,5,6-trifluoro-4-[(2-phenylethyl)thio]benzenesulfonamide (Compound 3c), 2-[(1-phenylethyl)amino]-3,5,6-trifluoro-4-[(2-phenylethyl)thio]benzenesulfonamide (compound 3d), 2-morpholin-4-yl-3,5,6-trifluoro-4-[(2-phenylethyl)thio]benzenesulfonamide (compound 3e), 2-(cyclohexylamino)-3,5,6-trifluoro-4-[(2-phenylethyl)thio]benzenesulfonamide (Compound 3f), 2-(cycloheptylamino)-3,5,6-trifluoro-4-[(2-phenylethyl)thio]benzenesulfonamide (Compound 3 g), 2-(cyclooctylamino)-3,5,6-trifluoro-4-[(2-phenylethyl)thio]benzenesulfonamide (Compound 3 h), 2-(cyclododecylamino)-3,5,6-trifluoro-4-[(2-phenylethyl)thio]benzenesulfonamide (Compound 3i) 2-[(2,6-dimethoxybenzyl)amino]-3,5,6-trifluoro-4-[(2-phenylethyl)thio]benzenesulfonamide (Compound 3j), 2-[(3,4-dimethoxybenzyl)amino]-3,5,6-trifluoro-4-[(2-phenylethyl)thio] benzenesulfonamide (Compound 3k), 2-(2,3-dihydro-1H-inden-2-ylamino)-3,5,6-trifluoro-4-[(2-phenylethyl)thio]benzenesulfonamide (Compound 3l), 2-[(1S)-2,3-dihydro-1H-inden-1-ylamino]-3,5,6-trifluoro-4-[(2-phenylethyl)thio]benzenesulfonamide (Compound 3m), 2-[(1S)-1,2,3,4-tetrahydronapthalen-1-ylamino)-3,5,6-trifluoro-4-[(2-phenylethyl)thio]benzenesulfonamide (Compound 3n), 2-{[(1S,2R)-2-hydroxy-1,2-diphenylethyl]amino}-3,5,6-trifluoro-4-[(2-phenylethyl)thio]benzenesulfonamide (compound 3o)

The mixture of 2,3,5,6-tetrafluoro-4-[(2-phenylethyl)thio]benzenesulfonamide (compound 2p) (0.2 g, 0.55 mmol), Et$_3$N (0.08 mL, 0.57 mmol), DMSO (1 mL) and appropriate nucleophile (0.57 mmol) was stirred at 60° C. for 16 h, compounds 3n, o were obtained after 40 h, compound 3e was obtained after stirring at 70° C. for 26 h. The mixture was then diluted with H$_2$O (20 mL) and extracted with EtAc (3×10 mL). The combined organic phase was dried over MgSO$_4$ and evaporated in vacuum.

The compound 3a. The product was purified by chromatography on a column of silica gel (0.04-0.063 mm) with EtAc (5%):CHCl$_3$, Rf=0.51. Yield: 0.12 g, 55%, mp 47-48° C.

$^1$H NMR (300 MHz, CDCl$_3$): 1.23 (6H, dd, $^1$J=6.3 Hz, $^2$J=1.2 Hz, 2CH$_3$), 2.94 (2H, t, J=8 Hz, SCH$_2$CH$_2$), 3.28 (2H, t, J=8 Hz, SCH$_2$CH$_2$), 3.84-3.95 (1H, m, CH), 5.52 (2H, br s, SO$_2$NH$_2$), 7.2-7.4 (5H, m, ArH).

$^{13}$C NMR (75 MHz, CDCl$_3$): 24 (2CH$_3$), 35.4 (SCH$_2$CH$_2$, t, J($^{19}$F—$^{13}$C)=3.7 Hz), 36.8 (SCH$_2$CH$_2$), 48.4 (CH, d, J($^{19}$F—$^{13}$C)=11 Hz), 117.4 (C1, dd, $^1$J($^{19}$F—$^{13}$C)=12 Hz, $^2$J($^{19}$F—$^{13}$C)=5 Hz), 119.9 (C4, t, J($^{19}$F—$^{13}$C)=21 Hz), 127 (Ar), 128.8 (Ar), 132.6 (C2, d, J($^{19}$F—$^{13}$C)=16 Hz), 139.4 (Ar), 142.2 (C5 or C6, ddd, $^1$J($^{19}$F—$^{13}$C)=240 Hz, $^2$J($^{19}$F—$^{13}$C)=16 Hz, $^3$J($^{19}$F—$^{13}$C)=5 Hz), 145 (C5 or C6, ddd, $^1$J($^{19}$F—$^{13}$C)=247 Hz, $^2$J($^{19}$F—$^{13}$C)=16 Hz, $^3$J($^{19}$F—$^{13}$C)=5 Hz), 148.6 (C3, d, J($^{19}$F—$^{13}$C)=243 Hz).

$^{19}$F NMR (282 MHz, CDCl$_3$): −125.1 (C3-F, d, J=11 Hz), −143.4 (C5-F, dd, $^1$J=27 Hz, $^2$J=12 Hz), −148.5 (C6-F, d, J=26 Hz).

HRMS calcd. for C$_{17}$H$_{19}$F$_3$N$_2$O$_2$S$_2$ [(M+H)$^+$]: 405.0913. found: 405.0918.

The compound 3b. The product was purified by chromatography on a column of silica gel (0.04-0.063 mm) with EtAc:CHCl$_3$ (1:14), Rf=0.45. Yield: 0.15 g, 60%, mp 94-95° C.

$^1$H NMR (300 MHz, DMSO-D$_6$): 2.74 (2H, t, J=7.4 Hz, SCH$_2$CH$_2$), 3.19 (2H, t, J=7.5 Hz, SCH$_2$CH$_2$), 4.51 (2H, dd, $^1$J=6.3 Hz, $^2$J=4.2 Hz, NHCH$_2$), 6.81 (1H, td, $^1$J=6.4 Hz, $^2$J=1.8 Hz, NH), 7.1-7.4 (10H, m, ArH), 8.2 (2H, s, SO$_2$NH$_2$).

$^{13}$C NMR (75 MHz, DMSO-D$_6$): 35.3 (SCH$_2$CH$_2$, t, J($^{19}$F—$^{13}$C)=3.2 Hz), 36.3 (SCH$_2$CH$_2$), 50.5 (NHCH$_2$, d, J($^{19}$F—$^{13}$C)=12 Hz), 118 (C4, t, J($^{19}$F—$^{13}$C)=19 Hz), 119.2 (C1, dd, J($^{19}$F—$^{13}$C)=12 Hz, $^2$J($^{19}$F—$^{13}$C)=4.5 Hz), 127.1 (Ar), 127.9 (Ar), 128.1 (Ar), 129 (Ar), 129.2 (Ar), 129.22 (Ar), 132.9 (C2, d, J($^{19}$F—$^{13}$C)=14 Hz), 139.8 (Ar), 140.1 (Ar), 141.8 (C5 or C6, d, J($^{19}$F—$^{13}$C)=234 Hz), 144.8 (C5 or C6, d, J($^{19}$F—$^{13}$C)=261 Hz), 148.1 (C3, d, J($^{19}$F—$^{13}$C)=242 Hz).

$^{19}$F NMR (282 MHz, DMSO-D$_6$): −121.2 (C3-F, d, J=9 Hz), −138.1 (C5-F, dd, $^1$J=27 Hz, $^2$J=12 Hz), −145.4 (C6-F, d, J=27 Hz).

HRMS calcd. for C$_{21}$H$_{19}$F$_3$N$_2$O$_2$S$_2$ [(M+H)$^+$]: 453.0913. found: 453.0917.

The compound 3c. The product was purified by chromatography on a column of silica gel (0.04-0.063 mm) with EtAc (10%):CHCl$_3$, Rf=0.53. Yield: 0.24 g, 92%, 90-91° C.

$^1$H NMR (300 MHz, CDCl$_3$): 2.9-3.0 (4H, m, SCH$_2$CH$_2$, NHCH$_2$CH$_2$), 3.29 (2H, t, J=8 Hz, SCH$_2$CH$_2$), 3.6-3.75 (2H, m, NHCH$_2$), 5.21 (2H, s, SO$_2$NH$_2$), 7.2-7.4 (10H, m, ArH).

$^{13}$C NMR (75 MHz, CDCl$_3$): 35.4 (SCH$_2$CH$_2$, t, J($^{19}$F—$^{13}$C)=4 Hz), 36.8 (SCH$_2$CH$_2$), 37.1 (NHCH$_2$CH$_2$), 48.2 (NHCH$_2$, d, J($^{19}$F—$^{13}$C)=11.5 Hz), 116.3 (C1, dd, $^1$J($^{19}$F—$^{13}$C)=12 Hz, $^2$J($^{19}$F—$^{13}$C)=5 Hz), 120 (C4, t, J($^{19}$F—$^{13}$C)=22 Hz), 126.9 (Ar), 127 (Ar), 128.8 (Ar), 128.9 (Ar), 129.2 (Ar), 133 (C2, d, J($^{19}$F—$^{13}$C)=14 Hz), 139 (Ar), 139.4 (Ar), 141.9 (C5 or C6, ddd, $^1$J($^{19}$F-$^{13}$C)=242 Hz, $^2$J($^{19}$F—$^{13}$C)=16 Hz, $^3$J($^{19}$F—$^{13}$C)=5 Hz), 145 (C5 or C6, ddd, $^1$J($^{19}$F—$^{13}$C)=253 Hz, $^2$J($^{19}$F—$^{13}$C)=11 Hz, $^3$J($^{19}$F—$^{13}$C)=4 Hz), 148.2 (C3, d, J($^{19}$F—$^{13}$C)=242 Hz).

$^{19}$F NMR (282 MHz, CDCl$_3$): −126.6 (C3-F, d, J=11 Hz), −143.6 (C5-F, dd, $^1$J=27 Hz, $^2$J=12 Hz), −149.1 (C6-F, d, J=28 Hz).

HRMS calcd. for C$_{22}$H$_{21}$F$_3$N$_2$O$_2$S$_2$ [(M+H)$^+$]: 467.1069. found: 467.1077.

The compound 3d. The product was purified by chromatography on a column of silica gel (0.04-0.063 mm) with EtAc (5%):CHCl$_3$, Rf=0.75. Yield: 0.15 g, 58%.

$^1$H NMR (300 MHz, CDCl$_3$): 1.59 (3H, dd, $^1$J=7 Hz, $^2$J=1 Hz, CH$_3$), 2.78 (2H, td, $^1$J=7.5 Hz, $^2$J=3 Hz, SCH$_2$CH$_2$), 3.13 (2H, t, J=8 Hz, SCH$_2$CH$_2$), 4.85-4.95 (1H, m, CH), 5.33 (2H, s, SO$_2$NH$_2$), 7.1-7.4 (10H, m, ArH).

$^{13}$C NMR (75 MHz, CDCl$_3$): 24.6 (CH$_3$), 35.5 (SCH$_2$CH$_2$, t, J($^{19}$F—$^{13}$C)=3.5 Hz), 36.7 (SCH$_2$CH$_2$), 56.4 (NHCH, d, J($^{19}$F—$^{13}$C)=12 Hz), 117.5 (C1, dd, $^1$J($^{19}$F—$^{13}$C)=12 Hz, $^2$J($^{19}$F-$^{13}$C)=5 Hz), 119.8 (C4, t, J($^{19}$F—$^{13}$C)=19.5 Hz), 126.3 (Ar), 126.9 (Ar), 127.7 (Ar), 128.8 (Ar), 128.8 (Ar), 128.9 (Ar), 132.3 (C2, d, J($^{19}$F—$^{13}$C)=13 Hz), 139.4 (Ar), 142.4 (C5 or C6, ddd, $^1$J($^{19}$F-$^{13}$C)=240 Hz, $^2$J($^{19}$F—$^{13}$C)=15 Hz, $^3$J($^{19}$F—$^{13}$C)=5 Hz), 144.9 (C5 or C6, ddd, $^1$J($^{19}$F—$^{13}$C)=248 Hz, $^2$J($^{19}$F—$^{13}$C)=16 Hz, $^3$J($^{19}$F—$^{13}$C)=4 Hz), 148.8 (C3, d, J($^{19}$F—$^{13}$C)=244 Hz).

$^{19}$F NMR (282 MHz, CDCl$_3$): −122.5 (C3-F, d, J=11 Hz), −143.2 (C5-F, dd, $^1$J=27 Hz, $^2$J=12 Hz), −147.4 (C6-F, d, J=26 Hz).

HRMS calcd. for C$_{22}$H$_{21}$F$_3$N$_2$O$_2$S$_2$ [(M+H)$^+$]: 467.1069. found: 467.1069.

The compound 3e. The product was purified by chromatography on a column of silica gel (0.04-0.063 mm) with EtAc:CHCl$_3$ (1:3), Rf=0.38. Yield: 0.1 g, 42%, mp 149-150° C.

$^1$H NMR (300 MHz, CDCl$_3$): 2.9-3.05 (4H, m, SCH$_2$CH$_2$, morpholine), 3.33 (2H, t, J=8 Hz, SCH$_2$CH$_2$), 3.48 (2H, t, J=11 Hz, morpholine), 3.73 (2H, t, J=11 Hz, morpholine), 4.0 (2H, d, J=11 Hz, morpholine), 6.12 (2H, s, SO$_2$NH$_2$), 7.15-7.35 (5H, m, ArH).

$^{13}$C NMR (75 MHz, CDCl$_3$): 35.3 (SCH$_2$CH$_2$, t, J($^{19}$F—$^{13}$C)=4 Hz), 36.9 (SCH$_2$CH$_2$), 51.3 (morpholine, d, J($^{19}$F—$^{13}$C)=6 Hz), 67.7 (morpholine), 120.3 (C4, t, J($^{19}$F—$^{13}$C)=21 Hz), 127.1 (Ar), 128.8 (Ar), 128.9 (Ar), 129.5 (C2, d, J($^{19}$F—$^{13}$C)=7 Hz), 131.7 (C1, dd, $^1$J($^{19}$F—$^{13}$C)=16 Hz, $^2$J($^{19}$F—$^{13}$C)=5 Hz), 139.1 (Ar), 143.9 (C5 or C6, ddd, $^1$J($^{19}$F—$^{13}$C)=260 Hz, $^2$J($^{19}$F—$^{13}$C)=16 Hz, $^3$J($^{19}$F—$^{13}$C)=5 Hz), 149.6 (C5 or C6, ddd, $^2$J($^{19}$F—$^{13}$C)=250 Hz, $^2$J($^{19}$F—$^{13}$C)=17 Hz, $^3$J($^{19}$F-$^{13}$C)=6 Hz), 157.8 (C3, d, J($^{19}$F—$^{13}$C)=251 Hz).

$^{19}$F NMR (282 MHz, CDCl$_3$): −118.8 (C3-F, d, J=13 Hz), −131.5 (C6-F, d, J=25 Hz), −143 (C5-F, d, $^1$J=24 Hz, $^2$J=13 Hz).

HRMS calcd. for C$_{18}$H$_{19}$F$_3$N$_2$O$_3$S$_2$ [(M+H)$^+$]: 433.0862. found: 433.0863.

The compound 3f. The product was purified by chromatography on a column of silica gel (0.04-0.063 mm) with EtAc:CHCl$_3$ (1:9), Rf=0.63. Yield: 0.12 g, 50%, mp 62-63° C.

$^1$H NMR (300 MHz, CDCl$_3$): 1.2-1.5 (5H, m, cyclohexane), 1.6-1.7 (1H, m, cyclohexane), 1.7-1.85 (2H, m, cyclohexane), 1.9-2.05 (2H, m, cyclohexane), 2.93 (2H, t, J=8 Hz, SCH$_2$CH$_2$), 3.27 (2H, t, J=8 Hz, SCH$_2$CH$_2$), 3.6-3.7 (1H, m, CH of cyclohexane), 5.57 (2H, s, SO$_2$NH$_2$), 6.16 (1H, br s, NH), 7.2-7.4 (5H, m, ArH).

$^{13}$C NMR (75 MHz, CDCl$_3$): 25 (cyclohexane), 25.8 (cyclohexane), 34.4 (cyclohexane), 35.4 (SCH$_2$CH$_2$, t, J($^{19}$F—$^{13}$C)=4 Hz), 36.8 (SCH$_2$CH$_2$), 55.3 (CH of cyclohexane, d, J($^{19}$F—$^{13}$C)=11 Hz), 117.2 (C1, dd, $^1$J($^{19}$F—$^{13}$C)=12 Hz, $^2$J($^{19}$F—$^{13}$C)=5 Hz), 119.6 (C4, t, J($^{19}$F—$^{13}$C)=22 Hz), 127 (Ar), 128.8 (Ar), 132.6 (C2, d, J($^{19}$F—$^{13}$C)=15 Hz), 139.4 (Ar), 142 (C5 or C6, ddd, $^1$J($^{19}$F-$^{13}$C)=240 Hz, $^2$J($^{19}$F—$^{13}$C)=16 Hz, $^3$J($^{19}$F—$^{13}$C)=5 Hz), 145 (C5 or C6, ddd, $^2$J($^{19}$F—$^{13}$C)=248 Hz, $^2$J($^{19}$F—$^{13}$C)=16 Hz, $^3$J($^{19}$F—$^{13}$C)=4 Hz), 148.5 (C3, d, J($^{19}$F—$^{13}$C)=243 Hz).

$^{19}$F NMR (282 MHz, CDCl$_3$): −125.1 (C3-F, d, J=10 Hz), −143.5 (C5-F, dd, $^1$J=27 Hz, $^2$J=12 Hz), −149 (C6-F, d, J=27 Hz).

HRMS calcd. for C$_{20}$H$_{23}$F$_3$N$_2$O$_2$S$_2$ [(M+H)$^+$]: 445.1226. found: 445.1235.

The compound 3 g. The product was purified by chromatography on a column of silica gel (0.04-0.063 mm) with EtAc (5%):CHCl$_3$, Rf=0.63. Yield: 0.12 g, 48%.

$^1$H NMR (300 MHz, CDCl$_3$): 1.4-1.8 (10H, m, cycloheptane), 1.9-2.1 (2H, m, cycloheptane), 2.94 (2H, t, J=8 Hz, SCH$_2$CH$_2$), 3.27 (2H, t, J=8 Hz, SCH$_2$CH$_2$), 3.7-3.8 (1H, m, CH of cycloheptane), 5.57 (2H, s, SO$_2$NH$_2$), 6 (1H, br s, NH), 7.1-7.4 (5H, m, ArH).

$^{13}$C NMR (75 MHz, CDCl$_3$): 24.1 (cycloheptane), 28.3 (cycloheptane), 35.4 (SCH$_2$CH$_2$, t, J($^{19}$F—$^{13}$C)=4 Hz), 36.1 (cycloheptane), 36.8 (SCH$_2$CH$_2$), 57.5 (CH of cycloheptane, d, J($^{19}$F—$^{13}$C)=10 Hz), 117.2 (C1, dd, $^1$J($^{19}$F—$^{13}$C)=12 Hz, $^2$J($^{19}$F—$^{13}$C)=5 Hz), 119.7 (C4, t, J($^{19}$F—$^{13}$C)=19 Hz), 127 (Ar), 128.8 (Ar), 132.5 (C2, d, J($^{19}$F—$^{13}$C)=15 Hz), 139.5 (Ar), 142 (C5 or C6, ddd, $^1$J($^{19}$F—$^{13}$C) 240 Hz, $^2$J($^{19}$F—$^{13}$C)=16 Hz, $^3$J($^{19}$F—$^{13}$C)=5 Hz), 145 (C5 or C6, ddd, $^1$J($^{19}$F—$^{13}$C)=250 Hz, $^2$J($^{19}$F—$^{13}$C)=16 Hz, $^3$J($^{19}$F—$^{13}$C)=4 Hz), 148.5 (C3, d, J($^{19}$F—$^{13}$C)=243 Hz).

$^{19}$F NMR (282 MHz, CDCl$_3$): −125.1 (C3-F, d, J=11 Hz), −143.4 (C5-F, dd, $^1$J=26 Hz, $^2$J=12 Hz), −148.9 (C6-F, d, J=25 Hz).

HRMS calcd. for C$_{21}$H$_{25}$F$_3$N$_2$O$_2$S$_2$ [(M+H)$^+$]: 459.1382. found: 459.1388.

The compound 3 h. The product was purified by chromatography on a column of silica gel (0.04-0.063 mm) with EtAc:CHCl$_3$ (1:6), Rf=0.8. Yield: 0.14 g, 54%.

$^1$H NMR (300 MHz, CDCl$_3$): 1.4-1.8 (12H, m, cyclooctane), 1.85-2 (2H, m, cyclooctane), 2.94 (2H, t, J=8 Hz, SCH$_2$CH$_2$), 3.27 (2H, t, J=8 Hz, SCH$_2$CH$_2$), 3.75-3.9 (1H, m, CH of cyclooctane), 5.45 (2H, s, SO$_2$NH$_2$), 7.1-7.4 (5H, m, ArH).

$^{13}$C NMR (75 MHz, CDCl$_3$): 23.7 (cyclooctane), 25.8 (cyclooctane), 27.5 (cyclooctane), 33.1 (cyclooctane), 35.4 (SCH$_2$CH$_2$, t, J($^{19}$F—$^{13}$C)=4 Hz), 36.8 (SCH$_2$CH$_2$), 56.3 (CH of cyclooctane, d, J($^{19}$F—$^{13}$C)=10 Hz), 117 (C1, dd, $^1$J($^{19}$F—$^{13}$C)=12 Hz, $^2$J($^{19}$F—$^{13}$C)=6 Hz), 119.8 (C4, t, J($^{19}$F—$^{13}$C)=18 Hz), 127 (Ar), 128.8 (Ar), 132.6 (C2, d, J($^{19}$F—$^{13}$C)=15 Hz), 139.5 (Ar), 141.8 (C5 or C6, ddd, $^1$J($^{19}$F—$^{13}$C)=240 Hz, $^2$J($^{19}$F—$^{13}$C)=16 Hz, $^3$J($^{19}$F—$^{13}$C)=5 Hz), 145.1 (C5 or C6, ddd, $^1$J($^{19}$F—$^{13}$C)=245 Hz, $^2$J($^{19}$F—$^{13}$C)=16 Hz, $^3$J($^{19}$F—$^{13}$C)=4 Hz), 148.5 (C3, d, J($^{19}$F-$^{13}$C)=243 Hz).

$^{19}$F NMR (282 MHz, CDCl$_3$): −124.9 (C3-F, d, J=11 Hz), −143.4 (C5-F, dd, $^1$J=27 Hz, $^2$J=12 Hz), −149.2 (C6-F, d, J=25 Hz).

HRMS calcd. for C$_{22}$H$_{27}$F$_3$N$_2$O$_2$S$_2$ [(M+H)$^+$]: 473.1539. found: 473.1548.

The compound 3i. The product was purified by chromatography on a column of silica gel (0.04-0.063 mm) with EtAc (5%):CHCl$_3$, Rf=0.65. Yield: 0.12 g, 41%, mp 98-99° C.

$^1$H NMR (300 MHz, CDCl$_3$): 1.3-1.8 (22H, m, cyclododecane), 2.94 (2H, t, J=8 Hz, SCH$_2$CH$_2$), 3.27 (2H, t, J=8 Hz, SCH$_2$CH$_2$), 3.84 (1H, br s, CH of cyclododecane), 5.4 (2H, s, SO$_2$NH$_2$), 7.1-7.4 (5H, m, ArH).

$^{13}$C NMR (75 MHz, CDCl$_3$): 21.3 (cyclododecane), 23.4 (cyclododecane), 23.5 (cyclododecane), 24.3 (cyclododecane), 24.6 (cyclododecane), 31 (cyclododecane), 35.4 (SCH$_2$CH$_2$, t, J($^{19}$F—$^{13}$C)=3.7 Hz), 36.8 (SCH$_2$CH$_2$), 53.6 (CH of cyclododecane, d, J($^{19}$F-$^{13}$C)=11 Hz), 116.7 (C1, dd, $^1$J($^{19}$F—$^{13}$C)=12 Hz, $^2$J($^{19}$F—$^{13}$C)=6 Hz), 119.8 (C4, t, J($^{19}$F—$^{13}$C)=18 Hz), 127 (Ar), 128.8 (Ar), 133.1 (C2, d, J($^{19}$F—$^{13}$C)=15 Hz), 139.4 (Ar), 141.7 (C5 or C6, ddd, $^1$J($^{19}$F—$^{13}$C)=237 Hz, $^2$J($^{19}$F—$^{13}$C)=16 Hz, $^3$J($^{19}$F—$^{13}$C)=5 Hz), 145.1 (C5 or C6, ddd, $^1$J($^{19}$F-$^{13}$C)=244.5 Hz, $^2$J($^{19}$F—$^{13}$C)=12 Hz, $^3$J($^{19}$F—$^{13}$C)=4 Hz), 148.4 (C3, d, J($^{19}$F—$^{13}$C)=242.6 Hz).

$^{19}$F NMR (282 MHz, CDCl$_3$): −120.1 (C3-F, d, J=11 Hz), −138.6 (C5-F, dd, $^1$J=23 Hz, $^2$J=12 Hz), −144.7 (C6-F, d, J=26 Hz).

HRMS calcd. for C$_{26}$H$_{35}$F$_3$N$_2$O$_2$S$_2$ [(M+H)$^+$]: 529.2165. found: 529.2164.

The compound 3j. The product was purified by chromatography on a column of silica gel (0.04-0.063 mm) with EtAc (5%):CHCl$_3$, Rf=0.53. Yield: 0.2 g, 71%, mp 118-119° C.

$^1$H NMR (300 MHz, CDCl$_3$): 2.96 (2H, t, J=8 Hz, SCH$_2$CH$_2$), 3.3 (2H, t, J=8 Hz, SCH$_2$CH$_2$), 3.79 (6H, s, 2CH$_3$), 4.53 (2H, d, J=1.5 Hz, NHCH$_2$), 5.25 (2H, s, SO$_2$NH$_2$), 6.55 (2H, d, J=8.4 Hz, ArH), 7.2-7.4 (6H, m, ArH).

$^{13}$C NMR (75 MHz, CDCl$_3$): 35.5 (SCH$_2$CH$_2$, t, J($^{19}$F—$^{13}$C)=4 Hz), 36.8 (SCH$_2$CH$_2$), 40.3 (NHCH$_2$, d, J($^{19}$F—$^{13}$C)=11 Hz), 56 (2CH$_3$), 104 (Ar), 115.3 (Ar), 119.1 (C4, t, J($^{19}$F—$^{13}$C)=19 Hz), 119.6 (C1, dd, $^1$J($^{19}$F—$^{13}$C)=11 Hz, $^2$J($^{19}$F—$^{13}$C)=4 Hz), 127 (Ar), 128.85 (Ar), 128.87 (Ar), 129.6 (Ar), 133.6 (C2, dd, $^1$J($^{19}$F—$^{13}$C)=15 Hz, $^2$J($^{19}$F—$^{13}$C)=3.3 Hz), 139.5 (Ar), 143.3 (C5 or C6, ddd, $^1$J($^{19}$F—$^{13}$C)=242 Hz, $^2$J($^{19}$F—$^{13}$C)=16 Hz, $^3$J($^{19}$F—$^{13}$C)=5 Hz), 144.4 (C5 or C6, ddd, $^1$J($^{19}$F-$^{13}$C)=251 Hz, $^2$J($^{19}$F—$^{13}$C)=16 Hz, $^3$J($^{19}$F—$^{13}$C)=4 Hz), 150.5 (C3, d, J($^{19}$F—$^{13}$C)=245 Hz), 158.8 (Ar).

$^{19}$F NMR (282 MHz, CDCl$_3$): −122.4 (C3-F, d, J=12 Hz), −144.2 (C5-F, dd, $^1$J=24 Hz, $^2$J=12 Hz), −146.3 (C6-F, d, J=25 Hz).

HRMS calcd. for C$_{23}$H$_{23}$F$_3$N$_2$O$_4$S$_2$ [(M+H)$^+$]: 513.1124. found: 513.1122.

The compound 3k. The product was purified by chromatography on a column of silica gel (0.04-0.063 mm) with EtAc (5%):CHCl$_3$, Rf=0.43. Yield: 0.13 g, 46%, mp 104-105° C.

$^1$H NMR (300 MHz, CDCl$_3$): 2.87 (2H, t, J=8 Hz, SCH$_2$CH$_2$), 3.22 (2H, t, J=8 Hz, SCH$_2$CH$_2$), 3.81 (3H, s, CH$_3$), 3.88 (3H, s, CH$_3$), 4.35 (2H, d, J=3.3 Hz, NHCH$_2$), 5.41 (2H, s, SO$_2$NH$_2$), 6.76 (1H, d, J=8.1 Hz, ArH), 6.83-6.92 (2H, m, ArH), 7.14-7.36 (5H, m, ArH).

$^{13}$C NMR (75 MHz, CDCl$_3$): 35.4 (SCH$_2$CH$_2$, t, J($^{19}$F—$^{13}$C)=3.5 Hz), 36.8 (SCH$_2$CH$_2$), 51 (NHCH$_2$, d, J($^{19}$F—$^{13}$C)=12 Hz), 56.06 (CH$_3$), 56.13 (CH$_3$), 111.2 (Ar), 117.6 (C1, dd, $^1$J($^{19}$F-$^{13}$C)=12 Hz, $^2$J($^{19}$F—$^{13}$C)=5 Hz), 119.8 (C4, t, J($^{19}$F—$^{13}$C)=21 Hz), 120.4 (Ar), 127 (Ar), 128.8 (Ar), 131.6 (Ar), 132.8 (C2, d, J($^{19}$F—$^{13}$C)=15 Hz), 139.4 (Ar), 142.4 (C5 or C6, ddd, $^1$J($^{19}$F—$^{13}$C)=240 Hz, $^2$J($^{19}$F—$^{13}$C)=16 Hz, $^3$J($^{19}$F—$^{13}$C)=5 Hz), 144.8 (C5 or C6, ddd, $^1$J($^{19}$F—$^{13}$C)=250 Hz, $^2$J($^{19}$F—$^{13}$C)=16 Hz, $^3$J($^{19}$F—$^{13}$C)=4 Hz), 148.6 (Ar), 148.9 (C3, d, J($^{19}$F—$^{13}$C)=243 Hz), 149.3 (Ar).

$^{19}$F NMR (282 MHz, CDCl$_3$): −123.9 (C3-F, d, J=13 Hz), −143.5 (C5-F, dd, $^1$J=27 Hz, $^2$J=12 Hz), −147.7 (C6-F, d, J=26 Hz).

HRMS calcd. for C$_{23}$H$_{23}$F$_3$N$_2$O$_4$S$_2$ [(M−H)$^-$]: 511.0979. found: 511.0982.

The compound 3l. The product was purified by chromatography on a column of silica gel (0.04-0.063 mm) with EtAc (10%):CHCl$_3$, Rf=0.55. Yield: 0.19 g, 73%, mp 73-74° C.

$^1$H NMR (300 MHz, CDCl$_3$): 2.85-3.05 (4H, m, SCH$_2$CH$_2$, CH$_2$ of indane), 3.25-3.4 (4H, m, SCH$_2$CH$_2$, CH$_2$ of indane), 4.58-4.7 (1H, m, NHCH), 5.12 (2H, s, SO$_2$NH$_2$), 7.2-7.4 (9H, m, ArH).

$^{13}$C NMR (75 MHz, CDCl$_3$): 35.4 (SCH$_2$CH$_2$, t, J($^{19}$F—$^{13}$C)=4 Hz), 36.9 (SCH$_2$CH$_2$), 41.2 (CH$_2$ of indane), 57.8 (NHCH, d, J($^{19}$F—$^{13}$C)=11 Hz), 117.2 (C1, dd, $^1$J($^{19}$F—$^{13}$C)=12 Hz, $^2$J($^{19}$F—$^{13}$C)=5.5 Hz), 120.1 (C4, t, J($^{19}$F—$^{13}$C)=22 Hz), 125.2 (Ar), 127 (Ar), 127.2 (Ar), 128.8 (Ar), 132.2 (C2, d, J($^{19}$F—$^{13}$C)=15 Hz), 139.4 (Ar), 141.1 (Ar), 142.2 (C5 or C6, ddd, $^1$J($^{19}$F—$^{13}$C)=239 Hz, $^2$J($^{19}$F—$^{13}$C)=16 Hz, $^3$J($^{19}$F—$^{13}$C)=5 Hz), 145 (C5 or C6, ddd, $^1$J($^{19}$F—$^{13}$C)=251 Hz, $^2$J($^{19}$F—$^{13}$C)=12 Hz, $^3$J($^{19}$F—$^{13}$C)=4 Hz), 148.2 (C3, d, J($^{19}$F—$^{13}$C)=242 Hz).

$^{19}$F NMR (282 MHz, CDCl$_3$): −126 (C3-F, d, J=12 Hz), −143.3 (C5-F, dd, $^1$J=27 Hz, $^2$J=12 Hz), −148.3 (C6-F, d, J=25 Hz).

HRMS calcd. for C$_{23}$H$_{21}$F$_3$N$_2$O$_2$S$_2$ [(M+H)$^+$]: 479.1069. found: 479.1077.

The compound 3m. The product was purified by chromatography on a column of silica gel (0.04-0.063 mm) with EtAc (5%):CHCl$_3$, Rf=0.53. Yield: 0.08 g, 31%, mp 101-102° C.

$^1$H NMR (300 MHz, CDCl$_3$): 2.05 (1H, sex, J=6 Hz, indane), 2.56 (1H, sex, J=7 Hz, indane), 2.85-2.97 (1H, m, indane, signal overlaps with signal of SCH$_2$CH$_2$), 2.99 (2H, t, J=8 Hz, SCH$_2$CH$_2$), 3.07-3.19 (1H, m, indane), 3.33 (2H, t, J=8 Hz, SCH$_2$CH$_2$), 5.18 (3H, br s, SO$_2$NH$_2$, NHCH), 6.34 (1H, br s, NH), 7.18-7.4 (9H, m, ArH).

$^{13}$C NMR (75 MHz, CDCl$_3$): 30.3 (indane), 35 (indane), 35.5 (SCH$_2$CH$_2$, t, J($^{19}$F—$^{13}$C)=3.8 Hz), 36.9 (SCH$_2$CH$_2$), 62.3 (NHCH, d, J($^{19}$F—$^{13}$C)=11 Hz), 117.6 (C1, dd, $^1$J($^{19}$F—$^{13}$C)=12 Hz, $^2$J($^{19}$F—$^{13}$C)=5 Hz), 120.1 (C4, t, J($^{19}$F—$^{13}$C)=22 Hz), 124.3 (Ar), 125.3 (Ar), 126.9 (Ar), 127 (Ar), 128.4 (Ar), 128.8 (Ar), 132.9 (C2, dd, $^1$J($^{19}$F—$^{13}$C)=15 Hz, $^2$J($^{19}$F—$^{13}$C)=3 Hz), 139.4 (Ar), 142.5 (C5 or C6, ddd, $^1$J($^{19}$F—$^{13}$C)=240 Hz, $^2$J($^{19}$F—$^{13}$C)=15 Hz, $^3$J($^{19}$F—$^{13}$C)=4 Hz), 143.7 (Ar), 144.3 (Ar), 145 (C5 or C6, ddd, $^1$J($^{19}$F—$^{13}$C)=248 Hz, $^2$J($^{19}$F—$^{13}$C)=16 Hz, $^3$J($^{19}$F—$^{13}$C)=5 Hz), 148.8 (C3, d, J($^{19}$F—$^{13}$C)=242 Hz).

$^{19}$F NMR (282 MHz, CDCl$_3$): −124.1 (C3-F, d, J=12 Hz), −143.1 (C5-F, dd, $^1$J=26 Hz, $^2$J=12 Hz), −147.9 (C6-F, d, J=25 Hz).

HRMS calcd. for C$_{23}$H$_{21}$F$_3$N$_2$O$_2$S$_2$ [(M+H)$^+$]: 479.1069. found: 479.1063.

The compound 3n. The product was purified by chromatography on a column of silica gel (0.04-0.063 mm) with EtAc (5%):CHCl$_3$, Rf=0.79. Yield: 0.14 g, 52%, mp 123-124° C.

$^1$H NMR (300 MHz, CDCl$_3$): 1.8-2.1 (4H, m, tetrahydronapthalene), 2.7-2.95 (2H, m, tetrahydronapthalene), 2.99 (2H, t, J=8 Hz, SCH$_2$CH$_2$), 3.33 (2H, t, J=8 Hz, SCH$_2$CH$_2$), 4.83 (1H, br s, NHCH), 5.1 (2H, s, SO$_2$NH$_2$), 6.26 (1H, br s, NH), 7.1-7.4 (9H, m, ArH).

$^{13}$C NMR (75 MHz, CDCl$_3$): 19 (tetrahydronapthalene), 29.3 (tetrahydronapthalene), 30.3 (tetrahydronapthalene), 35.5 (SCH$_2$CH$_2$, t, J($^{19}$F—$^{13}$C)=4 Hz), 36.9 (SCH$_2$CH$_2$), 54.7 (NHCH, d, J($^{19}$F—$^{13}$C)=11 Hz), 118.2 (C1, dd, $^1$J($^{19}$F—$^{13}$C)=12 Hz, $^2$J($^{19}$F—$^{13}$C)=5 Hz), 120 (C4, t, J($^{19}$F—$^{13}$C)=21 Hz), 126.2 (Ar), 127 (Ar), 127.7 (Ar), 128.9 (Ar), 129.1 (Ar), 129.7 (Ar), 132.6 (C2, d, J($^{19}$F—$^{13}$C)=15 Hz), 137.57 (Ar), 137.6 (Ar), 139.4 (Ar), 142.7 (C5 or C6, ddd, $^1$J($^{19}$F—$^{13}$C)=240 Hz, $^2$J($^{19}$F—$^{13}$C)=16 Hz, $^3$J($^{19}$F—$^{13}$C)=5 Hz), 145 (C5 or C6, ddd, $^1$J($^{19}$F—$^{13}$C)=249 Hz, $^2$J($^{19}$F—$^{13}$C)=12 Hz, $^3$J($^{19}$F—$^{13}$C)=4 Hz), 149.3 (C3, d, J($^{19}$F—$^{13}$C)=243 Hz).

$^{19}$F NMR (282 MHz, CDCl$_3$): −123.1 (C3-F, d, J=11 Hz), −142.9 (C5-F, dd, $^1$J=27 Hz, $^2$J=12 Hz), −147.4 (C6-F, d, J=26 Hz).

HRMS calcd. for C$_{24}$H$_{23}$F$_3$N$_2$O$_2$S$_2$ [(M+H)$^+$]: 493.1226. found: 493.1222.

The compound 3o. The product was purified by chromatography on a column of silica gel (0.04-0.063 mm) with EtAc (10%):CHCl$_3$, Rf=0.37. Yield: 0.11 g, 35%.

$^1$H NMR (300 MHz, CDCl$_3$): 2.73 (2H, t, J=7.2 Hz, SCH$_2$CH$_2$), 3.08 (2H, td, $^1$J=7.7 Hz, $^2$J=3.3 Hz, SCH$_2$CH$_2$), 5.01 (1H, dd, $^1$J=5.4 Hz, $^2$J=1.8 Hz, CH), 5.06 (1H, d, J=5.1 Hz, CH), 5.58 (2H, s, SO$_2$NH$_2$), 7.05-7.32 (15H, m, ArH).

$^{13}$C NMR (75 MHz, CDCl$_3$): 35.5 (SCH$_2$CH$_2$, t, J($^{19}$F—$^{13}$C)=3.4 Hz), 36.6 (SCH$_2$CH$_2$), 66.1 (NHCH, d, J($^{19}$F—$^{13}$C)=11 Hz), 77.3 (CHOH, signal overlaps with CDCl$_3$ signal), 117.7 (C1, dd, $^1J(^{19}F-^{13}C)$=12 Hz, $^2J(^{19}F-^{13}C)$=5 Hz), 119.8 (C4, t, $J(^{19}F-^{13}C)$=21 Hz), 126.8 (Ar), 126.9 (Ar), 128.2 (Ar), 128.3 (Ar), 128.5 (Ar), 128.7 (Ar), 128.8 (Ar), 131.6 (C2, d, $J(^{19}F-^{13}C)$=15 Hz), 138.1 (Ar), 139.3 (Ar), 140.4 (Ar), 142.5 (C5 or C6, ddd, $^1J(^{19}F-^{13}C)$=240 Hz, $^2J(^{19}F-^{13}C)$=16 Hz, $^3J(^{19}F-^{13}C)$=5 Hz), 144.8 (C5 or C6, ddd, $^1J(^{19}F-^{13}C)$=248 Hz, $^2J(^{19}F-^{13}C)$=12 Hz, $^3J(^{19}F-^{13}C)$=4 Hz), 148.6 (C3, d, $J(^{19}F-^{13}C)$=243 Hz).

$^{19}F$ NMR (282 MHz, CDCl$_3$): −122.6 (C3-F, d, J=12 Hz), −143.2 (C5-F, dd, $^1J$=25 Hz, $^2J$=12 Hz), −147.1 (C6-F, d, J=26 Hz).

HRMS calcd. for $C_{28}H_{25}F_3N_2O_3S_2$ [(M+H)$^+$]: 559.1331. found: 559.1331.

Example 14. Preparation of 2-(cyclooctylamino)-3,5,6-trifluoro-4-[(2-hydroxyethyl)thio]benzenesulfonamide (Compound 4a), 2-(cyclododecylamino)-3,5,6-trifluoro-4-[(2-hydroxyethyl)thio] benzenesulfonamide (Compound 4b), 2-[(2,6-dimethoxybenzyl)amino]-3,5,6-trifluoro-4-[(2-hydroxyethyl)thio]benzenesulfonamide (Compound 4c), 2-[(3,4-dimethoxybenzyl)amino]-3,5,6-trifluoro-4-[(2-hydroxyethyl)thio]benzenesulfonamide (Compound 4d), 2-[(1S)-2,3-dihydro-1H-inden-1-ylamino]-3,5,6-trifluoro-4-[(2-hydroxyethyl)thio] benzenesulfonamide (Compound 4e), 2-[(1S)-1,2,3,4-tetrahydronapthalen-1-yl amino)-3,5,6-trifluoro-4-[(2-hydroxyethyl)thio]benzenesulfonamide (Compound 4f), 2-{[(1S,2R)-2-hydroxy-1,2-diphenylethyl]amino}-3,5,6-trifluoro-4-[(2-hydroxyethyl)thio]benzenesulfonamide (Compound 4 g)

The mixture of 2,3,5,6-tetrafluoro-4[(2-hydroxyethyl)thio]benzenesulfonamide (compound 2c) (0.2 g, 0.66 mmol), Et$_3$N (0.095 mL, 0.68 mmol), DMSO (1 mL) and appropriate nucleophile (0.68 mmol) was stirred at 60° C. for 16 h. The mixture was then diluted with H$_2$O (20 mL) and extracted with EtAc (3×10 mL). The combined organic phase was dried over MgSO$_4$ and evaporated in vacuum.

The compound 4a. The product was purified by chromatography on a column of silica gel (0.04-0.063 mm) with EtAc:CHCl$_3$ (1:1), Rf=0.59. Yield: 0.15 g, 56%, mp 68-69° C.

$^1H$ NMR (300 MHz, CDCl$_3$): 1.4-1.75 (12H, m, cyclooctane), 1.8-1.95 (2H, m, cyclooctane), 2.54 (1H, br s, OH), 3.14 (2H, t, J=6 Hz, S$\underline{CH_2}$CH$_2$), 3.74 (2H, t, J=6 Hz, SCH$_2$$\underline{CH_2}$), 3.75-3.85 (1H, m, CH of cyclooctane, signal overlaps with signal of SCH$_2$$\underline{CH_2}$), 5.77 (2H, s, SO$_2$NH$_2$), 6.16 (1H, br s, NH).

$^{13}C$ NMR (75 MHz, CDCl$_3$): 23.7 (cyclooctane), 25.8 (cyclooctane), 27.5 (cyclooctane), 33 (cyclooctane), 37.5 (S$\underline{CH_2}$CH$_2$, br t), 56.4 (CH of cyclooctane, d, $J(^{19}F-^{13}C)$=11 Hz), 61.2 (SCH$_2$$\underline{CH_2}$), 117.9 (C1, dd, $^1J(^{19}F-^{13}C)$=12 Hz, $^2J(^{19}F-^{13}C)$=5 Hz), 118.3 (C4, t, $J(^{19}F-^{13}C)$=21 Hz), 132.7 (C2, d, $J(^{19}F-^{13}C)$=15 Hz), 142.1 (C5 or C6, ddd, $^1J(^{19}F-^{13}C)$=240 Hz, $^2J(^{19}F-^{13}C)$=16 Hz, $^3J(^{19}F-^{13}C)$=5 Hz), 145.1 (C5 or C6, ddd, $^1J(^{19}F-^{13}C)$=247 Hz, $^2J(^{19}F-^{13}C)$=16 Hz, $^3J(^{19}F-^{13}C)$=4 Hz), 149.1 (C3, d, $J(^{19}F-^{13}C)$=243 Hz).

$^{19}F$ NMR (282 MHz, CDCl$_3$): −124.5 (C3-F, d, J=11 Hz), −143 (C5-F, dd, $^1J$=27 Hz, $^2J$=12 Hz), −149 (C6-F, d, J=26 Hz).

HRMS calcd. for $C_{16}H_{23}F_3N_2O_3S_2$ [(M+H)$^+$]: 413.1175. found: 413.1175.

The compound 4b. The product was purified by chromatography on a column of silica gel (0.04-0.063 mm) with EtAc:CHCl$_3$ (1:1), Rf=0.65. Yield: 0.17 g, 55%, mp 113-114° C.

$^1H$ NMR (300 MHz, CDCl$_3$): 1.3-1.7 (22H, m, cyclododecane), 2.4 (1H, br s, OH), 3.16 (2H, t, J=6 Hz, S$\underline{CH_2}$CH$_2$), 3.75 (2H, t, J=6 Hz, SCH$_2$$\underline{CH_2}$), 3.78-3.86 (1H, m, CH cyclododecane, signal overlaps with signal of SCH$_2$$\underline{CH_2}$), 5.59 (2H, s, SO$_2$NH$_2$), 6.2 (1H, br s, NH).

$^{13}C$ NMR (75 MHz, CDCl$_3$): 21.3 (cyclododecane), 23.3 (cyclododecane), 23.4 (cyclododecane), 24.3 (cyclododecane), 24.6 (cyclododecane), 30.1 (cyclododecane), 37.6 (S$\underline{CH_2}$CH$_2$, t, $J(^{19}F-^{13}C)$=3 Hz), 53.6 (CH of cyclododecane, d, $J(^{19}F-^{13}C)$=11 Hz), 61.1 (SCH$_2$$\underline{CH_2}$), 117.5 (C1, dd, $^1J(^{19}F-^{13}C)$=12 Hz, $^2J(^{19}F-^{13}C)$=5 Hz), 118.4 (C4, t, $J(^{19}F-^{13}C)$=20 Hz), 133.3 (C2, d, $J(^{19}F-^{13}C)$=15 Hz), 141.9 (C5 or C6, ddd, $^1J(^{19}F-^{13}C)$=239 Hz, $^2J(^{19}F-^{13}C)$=16 Hz, $^3J(^{19}F-^{13}C)$=5 Hz), 145.1 (C5 or C6, ddd, $^1J(^{19}F-^{13}C)$=248 Hz, $^2J(^{19}F-^{13}C)$=16 Hz, $^3J(^{19}F-^{13}C)$=4 Hz), 148.9 (C3, d, $J(^{19}F-^{13}C)$=243 Hz).

$^{19}F$ NMR (282 MHz, CDCl$_3$): −124.5 (C3-F, d, J=11 Hz), −142.9 (C5-F, dd, $^1J$=27 Hz, $^2J$=12 Hz), −149.4 (C6-F, d, J=24 Hz).

HRMS calcd. for $C_{20}H_{31}F_3N_2O_3S_2$ [(M+H)$^+$]: 469.1801. found: 469.1804.

The compound 4c. The product was purified by chromatography on a column of silica gel (0.04-0.063 mm) with EtAc:CHCl$_3$ (1:1), Rf=0.54. Yield: 0.1 g, 34%.

$^1H$ NMR (300 MHz, CDCl$_3$): 3.15 (2H, t, J=6 Hz, S$\underline{CH_2}$CH$_2$), 3.72 (2H, t, J=6 Hz, SCH$_2$$\underline{CH_2}$), 3.79 (6H, s, 2CH$_3$), 4.51 (2H, s, CH$_2$), 5.4 (2H, br s, SO$_2$NH$_2$), 6.55 (2H, d, J=8.4 Hz, ArH), 7.22 (1H, t, J=8.4 Hz, ArH).

$^1H$ NMR (300 MHz, DMSO-D$_6$): 3.09 (2H, t, J=6 Hz, S$\underline{CH_2}$CH$_2$), 3.57 (2H, t, J=6.6 Hz, SCH$_2$$\underline{CH_2}$), 3.62 (1H, s, OH), 3.75 (6H, s, 2CH$_3$), 4.44 (2H, br s, CH$_2$), 6.5 (1H, br s, NH), 6.65 (2H, d, J=8.4 Hz, ArH), 7.24 (1H, t, J=8.4 Hz, ArH), 7.94 (2H, s, SO$_2$NH$_2$).

$^{13}C$ NMR (75 MHz, CDCl$_3$): 37.4 (S$\underline{CH_2}$CH$_2$, br t), 40.3 (NHCH$_2$, d, $J(^{19}F-^{13}C)$=11 Hz), 56 (CH$_3$), 61.2 (SCH$_2$$\underline{CH_2}$), 104 (Ar), 115 (Ar), 117.9 (C4, t, $J(^{19}F-^{13}C)$=19 Hz), 120.3 (C1, dd, $^1J(^{19}F-^{13}C)$=11 Hz, $^2J(^{19}F-^{13}C)$=4 Hz), 129.6 (Ar), 133.4 (C2, d, $J(^{19}F-^{13}C)$=16 Hz), 143.7 (C5 or C6, dd, $^1J(^{19}F-^{13}C)$=240 Hz, $^2J(^{19}F-^{13}C)$=15 Hz), 144.4 (C5 or C6, dd, $^1J(^{19}F-^{13}C)$=248 Hz, $^2J(^{19}F-^{13}C)$=16 Hz), 150.5 (C3, d, $J(^{19}F-^{13}C)$=244 Hz), 158.8 (Ar).

$^{19}F$ NMR (282 MHz, CDCl$_3$): −121.9 (C3-F, d, J=12 Hz), −143.7 (C5-F, dd, $^1J$=27 Hz, $^2J$=12 Hz), −145.9 (C6-F, d, J=25 Hz).

HRMS calcd. for $C_{17}H_{19}F_3N_2O_5S_2$ [(M+H)$^+$]: 453.076. found: 453.0752.

The compound 4d. The product was purified by chromatography on a column of silica gel (0.04-0.063 mm) with EtAc:CHCl$_3$ (1:1), Rf=0.45. Yield: 0.27 g, 91%, mp 73-74° C.

$^1H$ NMR (300 MHz, CDCl$_3$): 3.08 (2H, t, J=6 Hz, S$\underline{CH_2}$CH$_2$), 3.63 (2H, t, J=6 Hz, SCH$_2$$\underline{CH_2}$), 3.84 (3H, s, CH$_3$), 3.86 (3H, s, CH$_3$), 4.41 (2H, d, J=3.3 Hz, CH$_2$), 5.67 (2H, s, SO$_2$NH$_2$), 6.75-6.87 (3H, m, ArH).

$^{13}C$ NMR (75 MHz, CDCl$_3$): 37.4 (S$\underline{CH_2}$CH$_2$, t, $J(^{19}F-^{13}C)$=3 Hz), 51 (NHCH$_2$, d, $J(^{19}F-^{13}C)$=12 Hz), 56.11 (CH$_3$), 56.18 (CH$_3$), 61.1 (SCH$_2$$\underline{CH_2}$), 111.3 (Ar), 118.3 (C1, dd, $^1J(^{19}F-^{13}C)$=11 Hz, $^2J(^{19}F-^{13}C)$=5 Hz signal overlaps with signal of C4), 118.5 (C4, t, $J(^{19}F-^{13}C)$=21 Hz, signal overlaps with signal of C1), 120.4 (Ar), 131.5 (Ar), 132.9 (C2, d, $J(^{19}F-^{13}C)$=16 Hz), 142.6 (C5 or C6, ddd, $^1J(^{19}F-^{13}C)$=242 Hz, $^2J(^{19}F-^{13}C)$=15 Hz, $^3J(^{19}F-^{13}C)$=4 Hz), 144.8 (C5 or C6, ddd, $^1J(^{19}F-^{13}C)$=249 Hz, $^2J(^{19}F-^{13}C)=16$ Hz, $^3J(^{19}F-^{13}C)=5$ Hz), 148.6 (Ar), 149.2 (Ar), 149.3 (C3, d, $J(^{19}F-^{13}C)=243$ Hz).

$^{19}F$ NMR (282 MHz, CDCl$_3$): −123.6 (C3-F, d, J=12 Hz), −143.1 (C5-F, dd, $^1J=25$ Hz, $^2J=12$ Hz), −147.6 (C6-F, d, J=26 Hz).

HRMS calcd. for $C_{17}H_{19}F_3N_2O_5S_2[(M-H)^-]$: 451.0615. found: 451.0621.

The compound 4e. The product was purified by chromatography on a column of silica gel (0.04-0.063 mm) with EtAc:CHCl$_3$ (1:1), Rf=0.71. Yield: 0.13 g, 48%.

$^1H$ NMR (300 MHz, CDCl$_3$): 2.02 (1H, sex, J=7.2 Hz, indane), 2.54 (1H, sex, J=5.4 Hz, indane), 2.88 (1H, pet, J=8 Hz, indane), 3.04-3.16 (1H, m, indane), 3.19 (2H, t, J=6 Hz, S<u>CH$_2$</u>CH$_2$), 3.77 (2H, t, J=6 Hz, SCH$_2$<u>CH$_2$</u>), 5.12-5.2 (1H, m, NH<u>CH</u>), 5.35 (2H, s, SO$_2$NH$_2$), 7.15-7.35 (4H, m, ArH).

$^{13}C$ NMR (75 MHz, CDCl$_3$): 30.3 (indane), 35 (indane), 37.6 (S<u>CH$_2$</u>CH$_2$, t, $J(^{19}F-^{13}C)=2.5$ Hz), 61.3 (SCH$_2$<u>CH$_2$</u>), 62.2 (NHCH, d, $J(^{19}F-^{13}C)=10$ Hz), 118.3 (C1, dd, $^1J(^{19}F-^{13}C)=12$ Hz, $^2J(^{19}F-^{13}C)=5$ Hz), 118.8 (C4, t, $J(^{19}F-^{13}C)=21$ Hz), 124.2 (Ar), 125.3 (Ar), 126.9 (Ar), 128.4 (Ar), 133 (C2, d, $J(^{19}F-^{13}C)=15$ Hz), 142.7 (C5 or C6, ddd, $^1J(^{19}F-^{13}C)=242$ Hz, $^2J(^{19}F-^{13}C)=15$ Hz, $^3J(^{19}F-^{13}C)=4$ Hz), 143.7 (Ar), 144.2 (Ar), 145.1 (C5 or C6, ddd, $^1J(^{19}F-^{13}C)=251$ Hz, $^2J(^{19}F-^{13}C)=12$ Hz, $^3J(^{19}F-^{13}C)=4$ Hz), 149.2 (C3, d, $J(^{19}F-^{13}C)=242$ Hz).

$^{19}F$ NMR (282 MHz, CDCl$_3$): −123.8 (C3-F, d, J=12 Hz), −142.7 (C5-F, dd, $^1J=25$ Hz, $^2J=12$ Hz), −147.7 (C6-F, d, J=25 Hz).

HRMS calcd. for $C_{17}H_{17}F_3N_2O_3S_2$ [(M+H)$^+$]: 419.0705. found: 419.0714.

The compound 4f. The product was purified by chromatography on a column of silica gel (0.04-0.063 mm) with EtAc:CHCl$_3$ (1:1), Rf=0.66. Yield: 0.1 g, 36%, mp 94-95° C.

$^1H$ NMR (300 MHz, CDCl$_3$): 1.8-2.05 (4H, m, tetrahydronapthalene), 2.4 (1H, br s, OH), 2.7-3 (2H, m, tetrahydronapthalene), 3.19 (2H, t, J=6 Hz, S<u>CH$_2$</u>CH$_2$), 3.78 (2H, t, J=6 Hz, SCH$_2$<u>CH$_2$</u>), 4.76-4.86 (1H, m, NH<u>CH</u>), 5.3 (2H, br s, SO$_2$NH$_2$), 6.28 (1H, d, J=9 Hz, NH), 7.1-7.3 (4H, m, ArH).

$^{13}C$ NMR (75 MHz, CDCl$_3$): 18.9 (tetrahydronapthalene), 29.2 (tetrahydronapthalene), 30.3 (tetrahydronapthalene), 37.6 (S<u>CH$_2$</u>CH$_2$, br t, $J(^{19}F-^{13}C)=3$ Hz), 54.7 (NHCH, d, $J(^{19}F-^{13}C)=11$ Hz), 61.3 (SCH$_2$<u>CH$_2$</u>), 118.7 (C4, t, $J(^{19}F-^{13}C)=22$ Hz, signal overlaps with signal of C1), 118.9 (C1, dd, $^1J(^{19}F-^{13}C)=12$ Hz, $^2J(^{19}F-^{13}C)=4$ Hz, signal overlaps with signal of C4), 126.1 (Ar), 127.7 (Ar), 129.1 (Ar), 129.7 (Ar), 132.7 (C2, d, $J(^{19}F-^{13}C)=14$ Hz), 137.48 (Ar), 137.54 (Ar), 142.9 (C5 or C6, ddd, $^1J(^{19}F-^{13}C)=240$ Hz, $^2J(^{19}F-^{13}C)=15$ Hz, $^3J(^{19}F-^{13}C)=5$ Hz), 145.1 (C5 or C6, ddd, $^1J(^{19}F-^{13}C)=250$ Hz, $^2J(^{19}F-^{13}C)=12$ Hz, $^3J(^{19}F-^{13}C)=5$ Hz), 149.7 (C3, d, $J(^{19}F-^{13}C)=243$ Hz).

$^{19}F$ NMR (282 MHz, CDCl$_3$): −122.7 (C3-F, d, J=11 Hz), −142.5 (C5-F, dd, $^1J=27$ Hz, $^2J=12$ Hz), −147.3 (C6-F, d, J=26 Hz).

HRMS calcd. for $C_{18}H_{19}F_3N_2O_3S_2$ [(M-H)$^-$]: 431.0716. found: 431.0719.

The compound 4 g. The product was purified by chromatography on a column of silica gel (0.04-0.063 mm) with EtAc:CHCl$_3$ (1:1), Rf=0.43. Yield: 0.13 g, 39%.

$^1H$ NMR (300 MHz, CDCl$_3$): 2.2 (1H, br s, OH), 2.88 (2H, t, J=6 Hz, S<u>CH$_2$</u>CH$_2$), 3.1 (1H, br s, OH), 3.35-3.45 (2H, m, SCH$_2$<u>CH$_2$</u>), 4.97 (1H, br t, J=6 Hz, CH), 5.05 (1H, d, J=5 Hz, CH), 5.97 (2H, br s, SO$_2$NH$_2$), 7-7.3 (10H, m, ArH).

$^{13}C$ NMR (75 MHz, CDCl$_3$): 37.1 (S<u>CH$_2$</u>CH$_2$, br t, $J(^{19}F-^{13}C)=2$ Hz), 60.9 (SCH$_2$<u>CH$_2$</u>), 66.1 (NHCH, d, $J(^{19}F-^{13}C)=12$ Hz), 77 (CHOH, signal overlaps with CDCl$_3$ signal), 118.4 (C1, dd, $^1J(^{19}F-^{13}C)=11$ Hz, $^2J(^{19}F-^{13}C)=5$ Hz, signal overlaps with C4 signal), 118.3 (C4, t, $J(^{19}F-^{13}C)=20$ Hz, signal overlaps with C1 signal), 126.8 (Ar), 128 (Ar), 128.2 (Ar), 128.3 (Ar), 128.4 (Ar), 128.5 (Ar), 131.7 (C2, d, $J(^{19}F-^{13}C)=15$ Hz), 138.1 (Ar), 140.4 (Ar), 142.7 (C5 or C6, ddd, $^1J(^{19}F-^{13}C)=241$ Hz, $^2J(^{19}F-^{13}C)=15$ Hz, $^3J(^{19}F-^{13}C)=4$ Hz), 144.9 (C5 or C6, ddd, $^1J(^{19}F-^{13}C)=251$ Hz, $^2J(^{19}F-^{13}C)=12$ Hz, $^3J(^{19}F-^{13}C)=4$ Hz), 148.8 (C3, d, $J(^{19}F-^{13}C)=243$ Hz).

$^{19}F$ NMR (282 MHz, CDCl$_3$): −122.2 (C3-F, d, J=11 Hz), −142.9 (C5-F, dd, $^1J=26$ Hz, $^2J=12$ Hz), −147.3 (C6-F, d, J=26 Hz).

HRMS calcd. for $C_{22}H_{21}F_3N_2O_4S_2$ [(M+H)$^+$]: 499.0968. found: 499.0967.

Example 15. Preparation of 2-(cyclooctylamino)-3,5,6-trifluoro-4-(propylthio)benzenesulfonamide (Compound 5)

The mixture of 2,3,5,6-tetrafluoro-4-(propylthio)benzenesulfonamide (20 (0.2 g, 0.66 mmol), Et$_3$N (0.095 mL, 0.68 mmol), DMSO (1 mL) and cyclooctylamine (0.1 mL, 0.72 mmol) was stirred at 60° C. for 12 h. The mixture was then diluted with H$_2$O (20 mL) and extracted with EtAc (3×10 mL). The combined organic phase was dried over MgSO$_4$ and evaporated in vacuum.

The compound 5. The product was purified by chromatography on a column of silica gel (0.04-0.063 mm) with EtAc (5%):CHCl$_3$, Rf=0.64. Yield: 0.16 g, 59%.

$^1H$ NMR (300 MHz, CDCl$_3$): 1.03 (3H, t, J=7.2 Hz, CH$_3$), 1.4-1.75 (14H, m, <u>CH$_2$</u>CH$_3$, cyclooctane), 1.8-1.95 (2H, m, cyclooctane), 2.98 (2H, t, J=7.2 Hz, SCH$_2$), 3.7-3.85 (1H, m, CH of cyclooctane), 5.62 (3H, br s, NH, SO$_2$NH$_2$).

$^{13}C$ NMR (75 MHz, CDCl$_3$): 13.3 (CH$_3$), 23.5 (cyclooctane), 23.7 (cyclooctane), 25.8 (cyclooctane), 27.5 (cyclooctane), 33 (CH$_2$), 36.3 (SCH$_2$, t, $J(^{19}F-^{13}C)=3.6$ Hz), 56.5 (CH of cyclooctane, d, $J(^{19}F-^{13}C)=11$ Hz), 117.3 (C1, dd, $^1J(^{19}F-^{13}C)=12$ Hz, $^2J(^{19}F-^{13}C)$ 6 Hz), 120 (C4, t, $J(^{19}F-^{13}C)=21$ Hz), 132.4 (C2, d, $J(^{19}F-^{13}C)=13$ Hz), 142.2 (C5 or C6, ddd, $^1J(^{19}F-^{13}C)=239$ Hz, $^2J(^{19}F-^{13}C)=16$ Hz, $^3J(^{19}F-^{13}C)=5$ Hz), 145 (C5 or C6, ddd, $^1J(^{19}F-^{13}C)=249$ Hz, $^2J(^{19}F-^{13}C)=17$ Hz, $^3J(^{19}F-^{13}C)=4$ Hz), 148.9 (C3, d, $J(^{19}F-^{13}C)=243$ Hz).

$^{19}F$ NMR (282 MHz, CDCl$_3$): −124.8 (C3-F, d, J=11 Hz), −143.5 (C5-F, dd, $^1J=27$ Hz, $^2J=12$ Hz), −149 (C6-F, d, J=26 Hz).

HRMS calcd. for $C_{17}H_{25}F_3N_2O_2S_2$ [(M+H)$^+$]: 411.1382. found: 411.1388.

Example 16. Preparation of 2-(cyclooctylamino)-3,5,6-trifluoro-4-{[2-(4-hydroxyphenyl)ethyl]amino}benzenesulfonamide (Compound 6)

The mixture of 2,3,5,6-tetrafluoro-4{-[2-(4-hydroxyphenyl)ethyl]amino}benzenesulfonamide (2o) (0.2 g, 0.55 mmol), Et$_3$N (0.085 mL, 0.61 mmol), DMSO (1 mL) and cyclooctylamine (0.085 mL, 0.61 mmol) was stirred at 70° C. for 28 h. The mixture was then diluted with H$_2$O (20 mL) and extracted with EtAc (3×10 mL). The combined organic phase was dried over MgSO$_4$ and evaporated in vacuum.

The compound 6. The product was purified by chromatography on a column of silica gel (0.04-0.063 mm) with EtAc:CHCl$_3$ (1:3), Rf=0.6. Yield: 0.13 g, 50%.

$^1H$ NMR (300 MHz, CDCl$_3$): 1.4-2 (14H, m, cyclooctane), 2.82 (2H, t, J=7 Hz, NHCH$_2$<u>CH$_2$</u>), 3.6-3.75 (3H, m, CH of cyclooctane, NHCH$_2$CH$_2$), 5.59 (2H, s, SO$_2$NH$_2$), 6.1 (2H, br s, 2NH), 6.79 (2H, d, J=8.4 Hz, ArH), 7.04 (2H, d, J=8.4 Hz, ArH).

$^{13}$C NMR (75 MHz, CDCl$_3$): 23.8 (cyclooctane), 25.8 (cyclooctane), 27.5 (cyclooctane), 32.7 (cyclooctane), 36.6 (NHCH$_2$CH$_2$), 46.9 (NHCH$_2$CH$_2$), 56.4 (CH of cyclooctane, d, J($^{19}$F—$^{13}$C)=10 Hz), 106.3 (C1, dd, $^1$J($^{19}$F—$^{13}$C)=12 Hz, $^2$J($^{19}$F—$^{13}$C)=5 Hz), 115.8 (C4, signal overlaps with Ar signal), 115.83 (Ar), 130.2 (Ar), 130.28 (Ar), 132 (C2, d, J($^{19}$F—$^{13}$C)=13 Hz, signal overlaps with C5 or C6 signal), 133.8 (C5 or C6, ddd, $^1$J($^{19}$F—$^{13}$C)=239 Hz, $^2$J($^{19}$F—$^{13}$C)=18 Hz, $^3$J($^{19}$F—$^{13}$C)=6 Hz), 138.5 (C3, d, J($^{19}$F—$^{13}$C)=233 Hz), 146.5 (C5 or C6, ddd, $^1$J($^{19}$F—$^{13}$C)=243 Hz, $^2$J($^{19}$F—$^{13}$C)=14 Hz, $^3$J($^{19}$F—$^{13}$C)=3 Hz), 154.8 (Ar).

$^{19}$F NMR (282 MHz, CDCl$_3$): −144.8 (C5-F, dd, $^1$J=23 Hz, $^2$J=9 Hz), −154.1 (C3-F, s), −171.4 (C6-F, d, J=23 Hz).

HRMS calcd. for C$_{22}$H$_{28}$F$_3$N$_3$O$_3$S [(M+H)$^+$]: 472.1876. found: 472.1877.

Example 17. Preparation of 2-(cyclooctylamino)-3,5,6-trifluorobenzenesulfonamide (Compound 8a), 2-(cyclododecylamino)-3,5,6-trifluorobenzenesulfonamide (Compound 8b), 2-[(2,6-dimethoxybenzyl)amino]-3,5,6-trifluorobenzenesulfonamide (Compound 8c), 2-[(3,4-dimethoxybenzyl)amino]-3,5,6-trifluorobenzenesulfonamide (Compound 8d), 2-[(1S)-2,3-dihydro-1H-inden-1-ylamino]-3,5,6-trifluorobenzenesulfonamide (Compound 8e), 2-[(1S)-1,2,3,4-tetrahydronapthalen-1-ylamino)-3,5,6-trifluorobenzenesulfonamide (Compound 8f)

The mixture of 2,3,5,6-tetrafluorobenzenesulfonamide (7) (0.2 g, 0.87 mmol), Et$_3$N (0.124 mL, 0.89 mmol), DMSO (1 mL) and appropriate nucleophile (0.93 mmol) was stirred at 60° C. for 8 h, compound 8d was obtained after 16 h, compound 8f was obtained after stirring at 70° C. for 16 h. The mixture was then diluted with H$_2$O (20 mL) and extracted with EtAc (3×10 mL). The combined organic phase was dried over MgSO$_4$ and evaporated in vacuum.

The compound 8a. The product was purified by chromatography on a column of silica gel (0.04-0.063 mm) with EtAc:CHCl$_3$ (1:20), Rf=0.32. Yield: 0.15 g, 52%, mp 117-118° C.

$^1$H NMR (300 MHz, DMSO-D$_6$): 1.4-1.9 (14H, m, cyclooctane), 3.72 (1H, br s, CH of cyclooctane), 6.35 (1H, br s, NH), 7.65-7.8 (1H, m, ArH), 8.1 (2H, s, SO$_2$NH$_2$).

$^{13}$C NMR (75 MHz, DMSO-D$_6$): 23.6 (cyclooctane), 25.7 (cyclooctane), 27.6 (cyclooctane), 32.8 (cyclooctane), 55.7 (CH of cyclooctane, d, J($^{19}$F—$^{13}$C)=10 Hz), 110.2 (C4, t, J($^{19}$F—$^{13}$C)=25 Hz), 120.6 (C1, dd, $^1$J($^{19}$F—$^{13}$C)=12 Hz, $^2$J($^{19}$F—$^{13}$C)=5 Hz), 132.9 (C2, dd, $^1$J($^{19}$F—$^{13}$C)=13 Hz, $^2$J($^{19}$F—$^{13}$C)=3 Hz), 141.1 (C5 or C6, t, $^1$J($^{19}$F—$^{13}$C)=240 Hz, $^2$J($^{19}$F—$^{13}$C)=14 Hz), 145 (C5 or C6, ddd, $^1$J($^{19}$F—$^{13}$C)=248 Hz, $^2$J($^{19}$F—$^{13}$C)=14 Hz, $^3$J($^{19}$F—$^{13}$C)=5 Hz), 148.3 (C3, dd, $^1$J($^{19}$F—$^{13}$C)=236 Hz, $^2$J($^{19}$F—$^{13}$C)=6 Hz).

$^{19}$F NMR (282 MHz, DMSO-D$_6$): −120.6 (C3-F, t, J=13 Hz), −133.35: −133.56 (C5-F or C6-F, m), −145.2 (C5-F or C6-F, dd, $^1$J=25 Hz, $^2$J=11 Hz).

HRMS calcd. for C$_{14}$H$_{19}$F$_3$N$_2$O$_2$S [(M+H)$^+$]: 337.1192. found: 337.1195.

The compound 8b. The product was purified by chromatography on a column of silica gel (0.04-0.063 mm) with EtAc:CHCl$_3$ (1:20), Rf=0.49. Yield: 0.1 g, 29%, mp 113-114° C.

$^1$H NMR (300 MHz, DMSO-D$_6$): 1.2-1.7 (22H, m, cyclododecane), 3.71 (1H, br s, CH of cyclododecane), 6.22 (1H, d=7.8 Hz, NH), 7.64-7.78 (1H, m, ArH), 8.09 (2H, s, SO$_2$NH$_2$).

$^{13}$C NMR (75 MHz, DMSO-D$_6$): 21.4 (cyclododecane), 23.4 (cyclododecane), 23.6 (cyclododecane), 24.1 (cyclododecane), 24.4 (cyclododecane), 31.1 (cyclododecane), 52.8 (CH of cyclododecane, d, J($^{19}$F—$^{13}$C)=11 Hz), 110.2 (C4, t, J($^{19}$F—$^{13}$C)=25 Hz), 120.6 (C1, dd, $^1$J($^{19}$F—$^{13}$C) 12 Hz, $^2$J($^{19}$F—$^{13}$C) 5 Hz), 133.4 (C2, dd, $^1$J($^{19}$F—$^{13}$C)=12 Hz, $^2$J($^{19}$F—$^{13}$C)=2 Hz), 141.1 (C5 or C6, t, $^1$J($^{19}$F—$^{13}$C)=238 Hz, $^2$J($^{19}$F—$^{13}$C)=13 Hz), 145 (C5 or C6, ddd, $^1$J($^{19}$F—$^{13}$C)=249 Hz, $^2$J($^{19}$F—$^{13}$C)=14 Hz, $^3$J($^{19}$F—$^{13}$C)=4 Hz), 148.1 (C3, dd, $^1$J($^{19}$F—$^{13}$C)=245 Hz, $^2$J($^{19}$F—$^{13}$C)=9 Hz).

$^{19}$F NMR (282 MHz, DMSO-D$_6$): −125.4 (C3-F, t, J=13 Hz), −138: −138.3 (C5-F or C6-F, m), −150.1 (C5-F or C6-F, dd, $^1$J=25 Hz, $^2$J=11 Hz).

HRMS calcd. for C$_{18}$H$_{27}$F$_3$N$_2$O$_2$S [(M+H)$^+$]: 393.1818. found: 393.1816.

The compound 8c. The product was purified by chromatography on a column of silica gel (0.04-0.063 mm) with EtAc (5%):CHCl$_3$, Rf=0.4. Yield: 0.16 g, 48%, mp 137-138° C.

$^1$H NMR (300 MHz, D$_3$OD): 3.79 (6H, s, 2CH$_3$), 4.51 (2H, d, J=1.5 Hz, CH$_2$), 4.91 (2H, s, SO$_2$NH$_2$), 6.61 (2H, d, J=8.4 Hz, ArH), 7.22 (1H, t, J=8.1 Hz, ArH), 7.29-7.41 (1H, m, ArH).

$^1$H NMR (300 MHz, DMSO-D$_6$): 3.75 (6H, s, 2CH$_3$), 4.44 (2H, d, J=2.1 Hz, CH$_2$), 6.65 (2H, d, J=8.4 Hz, ArH), 7.25 (1H, t, J=8.4 Hz, ArH), 7.68-7.8 (1H, m, ArH), 7.92 (2H, s, SO$_2$NH$_2$).

$^1$H NMR (300 MHz, CDCl$_3$): 3.81 (6H, s, 2CH$_3$), 4.56 (2H, br s, CH$_2$), 4.92 (2H, br s, SO$_2$NH$_2$), 6.05 (1H, br s, NH), 6.57 (2H, d, J=8.4 Hz, ArH), 7.06-7.17 (1H, m, ArH), 7.24 (1H, t, J=8.4 Hz, ArH).

$^{13}$C NMR (75 MHz, D$_3$OD): 39.3 (CH$_2$, d, J($^{19}$F—$^{13}$C)=12 Hz), 55 (CH$_3$), 103.6 (Ar), 108.7 (C4, t, J($^{19}$F—$^{13}$C)=25 Hz), 115.1 (Ar), 121.4 (C1, dd, $^1$J($^{19}$F—$^{13}$C)=12 Hz, $^2$J($^{19}$F—$^{13}$C)=4 Hz), 129.2 (Ar), 134.3 (C2, dd, $^1$J($^{19}$F—$^{13}$C)=13 Hz, $^2$J($^{19}$F—$^{13}$C)=3 Hz), 142.2 (C5 or C6, d, J($^{19}$F—$^{13}$C)=241 Hz), 144.6 (C5 or C6, d, J($^{19}$F—$^{13}$C)=248 Hz), 149.9 (C3, d, J($^{19}$F—$^{13}$C)=249 Hz), 158.8 (Ar).

$^{19}$F NMR (282 MHz, DMSO-D$_6$): −124.1 (C3-F, t, J=13 Hz), −141.5: −141.7 (C5-F or C6-F, m), −150.3 (C5-F or C6-F, dd, $^1$J=25 Hz, $^2$J=10 Hz).

HRMS calcd. for C$_{15}$H$_{15}$F$_3$N$_2$O$_4$S [(M−H)$^−$]: 375.0632. found: 375.0634.

The compound 8d. The product was purified by chromatography on a column of silica gel (0.04-0.063 mm) with EtAc (10%):CHCl$_3$, Rf=0.29. Recrystallization was accomplished from EtOH:H$_2$O (2:1) after chromatography. Yield: 0.1 g, 33%, mp 115-116° C.

$^1$H NMR (300 MHz, DMSO-D$_6$): 3.73 (3H, s, CH$_3$), 3.75 (3H, s, CH$_3$), 4.4 (2H, dd, J=6 Hz, J=3.6 Hz, CH$_2$), 6.7 (1H, td, J=6 Hz, J=2 Hz, NH), 6.82-6.98 (3H, m, ArH), 7.65-7.78 (1H, m, ArH), 8.14 (2H, s, SO$_2$NH$_2$).

$^{13}$C NMR (75 MHz, DMSO-D$_6$): 50.3 (CH$_2$, d, J($^{19}$F—$^{13}$C)=12 Hz), 55.96 (CH$_3$), 56.06 (CH$_3$), 110.9 (C4, t, J($^{19}$F—$^{13}$C)=24 Hz), 111.9 (Ar), 112.2 (Ar), 120.3 (Ar), 120.4 (C1, signal overlaps with Ar signal), 132.3 (Ar), 133.5 (C2, d, J($^{19}$F—$^{13}$C)=13 Hz), 141.2 (C5 or C6, t, $^1$J($^{19}$F—$^{13}$C)=238 Hz, $^2$J($^{19}$F—$^{13}$C)=12 Hz), 144.8 (C5 or C6, d, J($^{19}$F—$^{13}$C)=252 Hz), 148.2 (C3, d J($^{19}$F—$^{13}$C)=240 Hz), 148.6 (Ar), 149.2 (Ar).

$^{19}$F NMR (282 MHz, DMSO-D$_6$): −124.9 (C3-F, t, J=13 Hz), −138.6: −138.8 (C5-F or C6-F, m), −149.6 (C5-F or C6-F, dd, $^1$J=25 Hz, $^2$J=10 Hz).

HRMS calcd. for $C_{15}H_{15}F_3N_2O_4S$ [(M−H)⁻]: 375.0632. found: 375.0631.

The compound 8e. The product was purified by chromatography on a column of silica gel (0.04-0.063 mm) with EtAc:CHCl₃ (1:10), Rf=0.38. Yield: 0.09 g, 30%, mp 103-104° C.

¹H NMR (300 MHz, DMSO-D₆): 1.79-1.95 (1H, m, indane), 2.38-2.5 (1H, m, indane), 2.82 (1H, pet, J=8 Hz, indane), 2.91-3.06 (1H, m, indane), 5.1-5.2 (1H, m, NHCH), 6.59 (1H, dd, ¹J=8.6 Hz, ²J=2 Hz, NH), 7.2-7.4 (4H, m, ArH), 7.75-7.9 (1H, m ArH), 8.13 (2H, s, SO₂NH₂).

¹³C NMR (75 MHz, DMSO-D₆): 30.2 (indane), 35.2 (indane), 61.6 (CH of indane, d, J(¹⁹F—¹³C)=11 Hz), 110.5 (C4, t, J(¹⁹F—¹³C)=25 Hz), 120.5 (C1, dd, ¹J(¹⁹F—¹³C)=12 Hz, ²J(¹⁹F-¹³C)=5 Hz), 124.7 (Ar), 125.5 (Ar), 127.3 (Ar), 128.6 (Ar), 133.2 (C2, dd, ¹J(¹⁹F—¹³C)=13 Hz, ²J(¹⁹F—¹³C)=3 Hz), 141.4 (C5 or C6, t, ¹J(¹⁹F—¹³C)=238 Hz, ²J(¹⁹F—¹³C)=14 Hz), 143.6 (Ar), 144.7 (Ar), 144.9 (C5 or C6, ddd, ¹J(¹⁹F—¹³C)=233 Hz, ²J(¹⁹F—¹³C)=14 Hz, ³J(¹⁹F—¹³C)=4 Hz), 148.2 (C3, d, J(¹⁹F—¹³C)=226 Hz).

¹⁹F NMR (282 MHz, DMSO-D₆): −120 (C3-F, t, J=13 Hz), −133.35: −133.55 (C5-F or C6-F, m), −144.7 (C5-F or C6-F, dd, ¹J=25 Hz, ²J=11 Hz).

HRMS calcd. for $C_{15}H_{13}F_3N_2O_2S$ [(M−H)⁻]: 341.0577. found: 341.0580.

The compound 8f. The product was purified by chromatography on a column of silica gel (0.04-0.063 mm) with EtAc (10%):CHCl₃, Rf=0.64. Yield: 0.1 g, 32%, mp 124-125° C.

¹H NMR (300 MHz, DMSO-D₆): 1.6-2 (4H, m, tetrahydronapthalene), 2.6-2.9 (2H, m, tetrahydronapthalene), 4.81 (1H, br s, NHCH), 6.53 (1H, d, J=8.7 Hz, NH), 7.1-7.25 (3H, m, ArH), 7.41 (1H, d, J=7.5 Hz, ArH), 7.73-7.85 (1H, m, ArH), 8.12 (2H, s, SO₂NH₂).

¹³C NMR (75 MHz, DMSO-D₆): 19.3 (tetrahydronapthalene), 29.3 (tetrahydronapthalene), 30.2 (tetrahydronapthalene), 53.8 (CH of tetrahydronapthalene, d, J(¹⁹F—¹³C)=12 Hz), 110.4 (C4, t, J(¹⁹F—¹³C)=25 Hz), 121 (C1, dd, ¹J(¹⁹F—¹³C)=12 Hz, ²J(¹⁹F-¹³C)=5 Hz), 126.6 (Ar), 127.9 (Ar), 129.6 (Ar), 129.7 (Ar), 132.7 (C2, dd, ¹J(¹⁹F—¹³C)=12 Hz, ²J(¹⁹F-¹³C)=2 Hz), 137.6 (Ar), 137.9 (Ar), 141.5 (C5 or C6, t, ¹J(¹⁹F—¹³C)=239 Hz, ²J(¹⁹F-¹³C)=13 Hz), 145 (C5 or C6, d, J(¹⁹F—¹³C)=247 Hz), 148.4 (C3, d, J(¹⁹F—¹³C)=239 Hz).

¹⁹F NMR (282 MHz, DMSO-D₆): −123.8 (C3-F, t, J=13 Hz), −137.9: −138.14 (C5-F or C6-F, m), −149.2 (C5-F or C6-F, dd, ¹J=25 Hz, ²J=10 Hz).

HRMS calcd. for $C_{16}H_{15}F_3N_2O_2S$ [(M−H)⁻]: 355.0734. found: 355.0733.

Example 18. Preparation of 3-(methylamino)-2,5,6-trifluoro-4-[(2-phenylethyl)sulfonyl]benzenesulfonamide (Compound 9a)

The mixture of 2,3,5,6-tetrafluoro-4-[(2-phenylethyl)sulfonyl]benzenesulfonamide (compound 2q) (0.2 g, 0.5 mmol), MeOH (10 mL) and methylamine (2M in methanol) (0.75 mL, 1.5 mmol) was refluxed for 7 h. MeOH was evaporated in vacuum and the resultant precipitate was filtered, washed with H₂O. Recrystallization was accomplished from EtOH:H₂O (2:1). Yield: 0.12 g, 57%, mp 152-153° C.

¹H NMR (300 MHz, DMSO-D₆): 3.01 (3H, dd, ¹J=7.5 Hz, ²J=5 Hz, CH₃), 3.08 (2H, t, J=7.5 Hz, SO₂CH₂CH₂), 3.89 (2H, t, J=7 Hz, SO₂CH₂CH₂), 6.6 (1H, br s, NH), 7.1-7.3 (5H, m, ArH), 8.31 (2H, s, SO₂NH₂).

¹³C NMR (75 MHz, DMSO-D₆): 28.6 (SO₂CH₂CH₂), 34.1 (CH₃, d, J(¹⁹F—¹³C)=13 Hz), 57.5 (SO₂CH₂CH₂), 114.4 (C4, dd, ¹J(¹⁹F—¹³C)=12 Hz, ²J(¹⁹F—¹³C)=5 Hz), 127.5 (Ar), 128 (C1, t, J(¹⁹F—¹³C)=18 Hz), 129 (Ar), 129.1 (Ar), 137.4 (C3, d, J(¹⁹F—¹³C)=12 Hz), 137.5 (Ar), 136.7 (C5 or C6, d, J(¹⁹F—¹³C)=244 Hz), 144.4 (C2, d, J(¹⁹F—¹³C)=251 Hz), 146.1 (C5 or C6, d, J(¹⁹F—¹³C)=240 Hz).

¹⁹F NMR (282 MHz, DMSO-D₆): −127.5 (C2-F, s), −135.9 (C6-F, dd, ¹J=25 Hz, ²J=12 Hz), −152.6 (C5-F, dd, ¹J=26 Hz, ²J=7 Hz).

HRMS calcd. for $C_{15}H_{15}F_3N_2O_4S_2$ [(M+H)⁺]: 409.0498. found: 409.0505.

Example 19. Preparation of 3-(benzylamino)-2,5,6-trifluoro-4-[(2-phenylethyl)sulfonyl]benzenesulfonamide (Compound 9c)

The mixture of 2,3,5,6-tetrafluoro-4-[(2-phenylethyl)sulfonyl]benzenesulfonamide (compound 2q) (0.3 g, 0.75 mmol), Et₃N (0.109 mL, 0.78 mmol), MeOH (10 mL) and benzylamine (0.085 mL, 0.78 mmol) was refluxed for 18 h. MeOH was evaporated in vacuum and the resultant precipitate was filtered, washed with H₂O. Recrystallization was accomplished from EtOH. Yield: 0.21 g, 57%, mp 59-61° C.

¹H NMR (300 MHz, DMSO-D₆): 3.0 (2H, t, J=8 Hz, SO₂CH₂CH₂), 3.82 (2H, t, J=7 Hz, SO₂CH₂CH₂), 4.54 (2H, dd, J=5.9 Hz, J=4 Hz, NHCH₂), 7.01 (1H, t, J=6 Hz, NH), 7.1-7.5 (10H, m, ArH), 8.4 (2H, br s, SO₂NH₂).

¹³C NMR (75 MHz, DMSO-D₆): 28.5 (SO₂CH₂CH₂), 50.5 (NHCH₂, d, J(¹⁹F—¹³C)=13 Hz), 57.7 (SO₂CH₂CH₂), 115.6 (C4, dd, ¹J(¹⁹F—¹³C)=13 Hz, ²J(¹⁹F—¹³C)=5 Hz), 127.5 (Ar), 128.2 (Ar), 128.4 (Ar), 129 (Ar), 129.1 (Ar), 129.3 (Ar), 136 (C3, d, J(¹⁹F—¹³C)=14 Hz), 137.5 (Ar), 139.7 (Ar), 139.4 (C5 or C6, d, J(¹⁹F—¹³C)=244 Hz), 144.9 (C2, d, J(¹⁹F—¹³C)=253 Hz), 146 (C5 or C6, d, J(¹⁹F—¹³C)=253 Hz).

¹⁹F NMR (282 MHz, DMSO-D₆): −124.7 (C2-F, s), −134.9 (C6-F, dd, ¹J=25 Hz, ²J=12 Hz), −150.4 (C5-F, dd, ¹J=26 Hz, ²J=7 Hz).

HRMS calcd. for $C_{21}H_{19}F_3N_2O_4S_2$ [(M+H)⁺]: 485.0811. found: 485.0814.

Example 20. Preparation of 3-(tert-butylamino)-2,5,6-trifluoro-4-[(2-phenylethyl)sulfonyl]benzenesulfonamide (Compound 9b), 3-morpholin-4-yl-2,5,6-trifluoro-4-[(2-phenylethyl)sulfonyl]benzenesulfonamide (Compound 9e)

The mixture of 2,3,5,6-tetrafluoro-4-[(2-phenylethyl)sulfonyl]benzenesulfonamide (compound 2q) (0.2 g, 0.5 mmol), DMSO (1 mL) and appropriate nucleophile (1.02 mmol) was stirred at ambient temperature for 4 days. The mixture was then diluted with H₂O (20 mL) and the resultant precipitate was filtered, washed with H₂O.

The compound 9b. The product was purified by chromatography on a column of silica gel (0.04-0.063 mm) with EtAc:CHCl₃ (1:4), Rf=0.62. Yield: 0.04 g, 18%, mp 127° C.

¹H NMR (300 MHz, CDCl₃): 1.38 (9H, d, J=2 Hz, 3CH₃), 3.14 (2H, t, J=8 Hz, SO₂CH₂CH₂), 3.65 (2H, t, J=8 Hz, SO₂CH₂CH₂), 5.74 (2H, s, SO₂NH₂), 6.63 (1H, s, NH), 7.1-7.4 (5H, m, ArH).

¹³C NMR (75 MHz, CDCl₃): 28.8 (SO₂CH₂Cl-12), 30.9 (CH₃, d, J=7 Hz), 55.7 (SO₂CH₂CH₂), 58.8 (NHC, d, J(¹⁹F—¹³C)=4 Hz), 118.5 (C4, dd, ¹J(¹⁹F—¹³C)=12 Hz, ²J(¹⁹F-¹³C)=6 Hz), 126.3 (C1, t, J(¹⁹F—¹³C)=16 Hz), 127.6 (Ar), 128.5 (Ar), 129.2 (Ar), 135.8 (C3, dd, ¹J(¹⁹F—¹³C) 18 Hz, ²J(¹⁹F—¹³C)=3 Hz), 136.6 (Ar), 138.3 (C5 or C6, ddd, $^1J(^{19}F—^{13}C)$=252 Hz, $^2J(^{19}F—^{13}C)$=18 Hz, $^3J(^{19}F—^{13}C)$=5 Hz), 145.8 (C2, d, $J(^{19}F—^{13}C)$=254 Hz), 146.1 (C5 or C6, ddd, $^1J(^{19}F—^{13}C)$=253 Hz, $^2J(^{19}F—^{13}C)$=16 Hz, $^3J(^{19}F—^{13}C)$=4 Hz).

$^{19}F$ NMR (282 MHz, CDCl$_3$): −122.2 (C2-F, s), −137.6 (C6-F, dd, $^1J$=25 Hz, $^2J$=12 Hz), −152.9 (C5-F, dd, $^1J$=26 Hz, $^2J$=6 Hz).

HRMS calcd. for C$_{18}$H$_{21}$F$_3$N$_2$O$_4$S$_2$ [(M+H)$^4$]: 451.0968. found: 451.0969.

The compound 9e. Recrystallization was accomplished from EtOH. Yield: 0.11 g, 46%, mp 198-199° C.

$^1$H NMR (300 MHz, DMSO-D$_6$): 2.9 (2H, d, J=11 Hz, morpholine), 3.12 (2H, t, J=8 Hz, SO$_2$CH$_2$CH$_2$), 3.21 (2H, t, J=11 Hz, morpholine), 3.57 (2H, t, J=11 Hz, morpholine), 3.79 (2H, d, J=11 Hz, morpholine), 4.06 (2H, t, J=8 Hz, SO$_2$CH$_2$CH$_2$), 7.2-7.4 (5H, m, ArH), 8.48 (2H, s, SO$_2$NH$_2$).

$^{13}$C NMR (75 MHz, DMSO-D$_6$): 33.3 (SO$_2$CH$_2$CH$_2$), 56.6 (morpholine, d, $J(^{19}F—^{13}C)$=4 Hz), 62.3 (SO$_2$CH$_2$CH$_2$), 71.8 (morpholine), 132.2 (Ar), 133.8 (Ar), 134.1 (Ar), 136.1 (C1, t, $J(^{19}F—^{13}C)$=6 Hz), 139.7 (C4, dd, $^1J(^{19}F—^{13}C)$=16 Hz, $^2J(^{19}F—^{13}C)$=5 Hz), 142.9 (Ar), 150.7 (C5, C6, dd, $^1J(^{19}F—^{13}C)$=261 Hz, $^2J(^{19}F—^{13}C)$=17 Hz), 159.3 (C2, d, $J(^{19}F—^{13}C)$=259 Hz).

$^{19}F$ NMR (282 MHz, DMSO-D$_6$): −119.1 (C2-F, d, J=14 Hz), −132.4 (C5-F, d, J=25 Hz), −136.7 (C6-F, dd, $^1J$=25 Hz, $^2J$=14 Hz).

HRMS calcd. for C$_{18}$H$_{19}$F$_3$N$_2$O$_5$S$_2$ [(M+H)$^+$]: 465.076. found: 465.0765.

Example 21. Preparation of 3-[(2-phenylethy)amino]-2,5,6-trifluoro-4-[(2-phenylethyl)sulfonyl]benzenesulfonamide (Compound 9d), 3-(cyclooctylamino)-2,5,6-trifluoro-4[(2-phenylethyl)sulfonyl]benzenesulfonamide (Compound 9l), 3-(cyclododecylamino)-2,5,6-trifluoro-4-[(2-phenylethyl)sulfonyl]benzenesulfonamide (Compound 9 g), 3-[(2,6-dimethoxybenzyl)amino]-2,5,6-trifluoro-4-[(2-phenylethyl)sulfonyl]benzenesulfonamide (Compound 9 h), 3-[(3,4-dimethoxybenzyl)amino]-2,5,6-trifluoro-4-[(2-phenylethyl)sulfonyl]benzenesulfonamide (Compound 9i), 3-(2,3-dihydro-1H-inden-2-ylamino)-2,5,6-trifluoro-4-[(2-phenylethyl)sulfonyl]benzenesulfonamide (Compound 9k), 3-[(1S)-2,3-dihydro-1H-inden-1-ylamino]-2,5,6-trifluoro-4-[(2-phenylethyl)sulfonyl]benzenesulfonamide (Compound 9l), 3-[(1S)-1,2,3,4-tetrahydronapthalen-1-ylamino)-2,5,6-trifluoro-4-[(2-phenylethyl)sulfonyl]benzenesulfonamide (Compound 9m)

The mixture of 2,3,5,6-tetrafluoro-4-[(2-phenylethyl)sulfonyl]benzenesulfonamide (compound 2q) (0.2 g, 0.5 mmol), Et$_3$N (0.071 mL, 0.51 mmol), DMSO (1 mL) and appropriate nucleophile (0.51 mmol) was stirred at ambient temperature for 24 h. The mixture was then diluted with H$_2$O (20 mL) and extracted with EtAc (3×10 mL). The combined organic phase was dried over MgSO$_4$ and evaporated in vacuum.

The compound 9d. The product was purified by chromatography on a column of silica gel (0.04-0.063 mm) with EtAc:CHCl$_3$ (1:6), Rf=0.48. Yield: 0.18 g, 72%, mp 141-142° C.

$^1$H NMR (300 MHz, DMSO-D$_6$): 2.88 (2H, t, J=7 Hz, NHCH$_2$CH$_2$), 2.98 (2H, t, J=7 Hz, SO$_2$CH$_2$CH$_2$), 3.6 (2H, br t, NHCH$_2$CH$_2$), 3.77 (2H, t, J=8 Hz, SO$_2$CH$_2$CH$_2$), 6.68 (1H, br s, NH), 7.1-7.4 (10H, m, ArH), 8.33 (2H, s, SO$_2$NH$_2$).

$^{13}$C NMR (75 MHz, DMSO-D$_6$): 28.6 (SO$_2$CH$_2$CH$_2$), 36.8 (NHCH$_2$CH$_2$), 48.3 (NHCH$_2$CH$_2$, d, $J(^{19}F—^{13}C)$=13 Hz), 57.5 (SO$_2$CH$_2$CH$_2$), 114.6 (C4, d, $J(^{19}F—^{13}C)$=12 Hz), 127.1 (Ar), 127.5 (Ar), 128.1 (C1, t, $J(^{19}F—^{13}C)$=16 Hz), 128.9 (Ar), 129 (Ar), 129.2 (Ar), 129.5 (Ar), 136.1 (C3, d, $J(^{19}F—^{13}C)$=13 Hz), 137.5 (Ar), 139.3 (Ar), 137 (C5 or C6, d, $J(^{19}F—^{13}C)$=244 Hz), 144.3 (C2, d, $J(^{19}F—^{13}C)$=250 Hz), 145.7 (C5 or C6, d, $J(^{19}F—^{13}C)$=233 Hz).

$^{19}F$ NMR (282 MHz, DMSO-D$_6$): −127 (C2-F, s), −135.3 (C6-F, dd, $^1J$=27 Hz, $^2J$=12 Hz), −152 (C5-F, dd, $^1J$=26 Hz, $^2J$=7 Hz).

HRMS calcd. for C$_{22}$H$_{21}$F$_3$N$_2$O$_4$S$_2$ [(M+H)$^+$]: 499.0968. found: 499.0971.

The compound 9f. The product was purified by chromatography on a column of silica gel (0.04-0.063 mm) with EtAc:CHCl$_3$ (1:9), Rf=0.5. Yield: 0.22 g, 88%, mp 90-92° C.

$^1$H NMR (300 MHz, CDCl$_3$): 1.4-2 (14H, m, cyclooctane), 3.14 (2H, t, J=8 Hz, SO$_2$CH$_2$CH$_2$), 3.64 (2H, t, J=8 Hz, SO$_2$CH$_2$CH$_2$), 3.85-3.95 (1H, m, cyclooctane), 5.68 (2H, s, SO$_2$NH$_2$), 6.91 (1H, d, J=8.7 Hz, NH), 7.1-7.4 (5H, m, ArH).

$^{13}$C NMR (75 MHz, CDCl$_3$): 23.5 (cyclooctane), 25.7 (cyclooctane), 27.5 (cyclooctane), 28.7 (SO$_2$CH$_2$CH$_2$), 33.2 (cyclooctane), 56.3 (CH of cyclooctane, d, $J(^{19}F—^{13}C)$=11 Hz), 58.8 (SO$_2$CH$_2$CH$_2$, d, $J(^{19}F—^{13}C)$=4 Hz), 114.7 (C4, dd, $^1J(^{19}F—^{13}C)$=12 Hz, $^2J(^{19}F—^{13}C)$=7 Hz), 126.4 (C1, t, $J(^{19}F—^{13}C)$=16 Hz), 127.6 (Ar), 128.5 (Ar), 129.1 (Ar), 136 (C3, d, $J(^{19}F—^{13}C)$=13 Hz), 136.5 (Ar), 136.7 (C5 or C6, d, $J(^{19}F—^{13}C)$=251 Hz), 145.8 (C2, d, $J(^{19}F—^{13}C)$=252 Hz), 146.2 (C5 or C6, dd, $^1J(^{19}F—^{13}C)$=252 Hz, $^2J(^{19}F—^{13}C)$=16 Hz).

$^{19}F$ NMR (282 MHz, CDCl$_3$): −131 (C2-F, s), −138.2 (C6-F, dd, $^1J$=25 Hz, $^2J$=12 Hz), −156.9 (C5-F, dd, $^1J$=26 Hz, $^2J$=7 Hz).

HRMS calcd. for C$_{22}$H$_{27}$F$_3$N$_2$O$_4$S$_2$ [(M+H)$^+$]: 505.1437. found: 505.1439.

The compound 9 g. The product was purified by chromatography on a column of silica gel (0.04-0.063 mm) with EtAc:CHCl$_3$ (1:10), Rf=0.37. Yield: 0.13 g, 46%, mp 130-131° C.

$^1$H NMR (300 MHz, DMSO-D$_6$): 1.2-1.7 (22H, m, cyclododecane), 3.07 (2H, t, J=8 Hz, SO$_2$CH$_2$CH$_2$), 3.8 (1H, br s, CH of cyclododecane), 3.88 (2H, t, J=7 Hz, SO$_2$CH$_2$CH$_2$), 6.55 (1H, d, J=8 Hz, NH), 7.1-7.3 (5H, m, ArH), 8.36 (2H, s, SO$_2$NH$_2$).

$^{13}$C NMR (75 MHz, DMSO-D$_6$): 21.2 (cyclododecane), 23.3 (cyclododecane), 23.4 (cyclododecane), 24.5 (cyclododecane), 24.7 (cyclododecane), 28.5 (SO$_2$CH$_2$CH$_2$), 30.8 (cyclododecane), 53.5 (CH of cyclododecane, d, $J(^{19}F—^{13}C)$=12 Hz), 58 (SO$_2$CH$_2$CH$_2$), 115.4 (C4, dd, $^1J(^{19}F—^{13}C)$=13 Hz, $^2J(^{19}F—^{13}C)$=4 Hz), 127.5 (Ar), 128.2 (C1, t, $J(^{19}F—^{13}C)$=16 Hz), 129 (Ar), 135.8 (C3, d, $J(^{19}F—^{13}C)$=16 Hz), 137.6 (Ar), 137.5 (C5 or C6, dd, $^1J(^{19}F—^{13}C)$=J 246 Hz, $^2J(^{19}F—^{13}C)$=17 Hz), 144.7 (C2, d, $J(^{19}F—^{13}C)$=250 Hz), 146.2 (C5 or C6, dd, $^1J(^{19}F—^{13}C)$=249 Hz, $^2J(^{19}F—^{13}C)$=17 Hz).

$^{19}F$ NMR (282 MHz, DMSO-D$_6$): −125.4 (C2-F, s), −134.5 (C6-F, dd, $^1J$=27 Hz, $^2J$=12 Hz), −151 (C5-F, dd, $^1J$=27 Hz, $^2J$=6 Hz).

HRMS calcd. for C$_{26}$H$_{35}$F$_3$N$_2$O$_4$S$_2$ [(M+H)$^+$]: 561.2063. found: 561.2071.

The compound 9 h. The product was purified by chromatography on a column of silica gel (0.04-0.063 mm) with EtAc:CHCl$_3$ (1:5), Rf=0.47. Yield: 0.13 g, 48%, mp 133-137° C.

$^1$H NMR (300 MHz, DMSO-D$_6$): 2.76 (2H, t, J=8 Hz, SO$_2$CH$_2$CH$_2$), 3.47 (2H, t, J=8 Hz, SO$_2$CH$_2$CH$_2$), 3.74 (6H, s, 2CH₃), 4.52 (2H, d, J=5.4 Hz, NHC̲H₂), 6.62 (2H, d, J=8.4 Hz, ArH) 6.69 (1H, br t, NH), 7.05-7.3 (6H, m, ArH), 8.4 (2H, s, SO₂NH₂).

$^{13}$C NMR (75 MHz, DMSO-D₆): 28.2 (SO₂CH₂C̲H₂), 39.4 (NHC̲H₂, d, J($^{19}$F—$^{13}$C)=13 Hz, signal overlaps with signal of DMSO), 56.4 (CH₃), 57.6 (SO₂C̲H₂CH₂), 104.7 (Ar), 114.7 (Ar), 116.5 (C4, dd, $^1$J($^{19}$F—$^{13}$C)=13 Hz, $^2$J($^{19}$F—$^{13}$C)=5 Hz), 127.4 (Ar), 127.9 (C1, t, J($^{19}$F—$^{13}$C)=16 Hz), 129 (Ar), 129.1 (Ar), 130.4 (Ar), 136.9 (C3, d, J($^{19}$F—$^{13}$C)=13 Hz), 137.5 (Ar), 138.1 (C5 or C6, d $^1$J($^{19}$F—$^{13}$C)=251 Hz), 145.5 (C5 or C6, d, J($^{19}$F—$^{13}$C)=253 Hz), 146.1 (C2, d, J($^{19}$F—$^{13}$C)=254 Hz), 158.7 (Ar).

$^{19}$F NMR (282 MHz, DMSO-D₆): −121.8 (C2-F, dd, $^1$J=11 Hz, $^2$J=5 Hz), −135.5 (C6-F, dd, $^1$J=27 Hz, $^2$J=12 Hz), −149.6 (C5-F, dd, $^1$J=27 Hz, $^2$J=5 Hz).

HRMS calcd. for $C_{23}H_{23}F_3N_2O_6S_2$ [(M−H)⁻]: 543.0877. found: 543.0881.

The compound 9i. Recrystallization was accomplished from EtOH. Yield: 0.18 g, 67%, mp 167-168° C.

$^1$H NMR (300 MHz, DMSO-D₆): 2.95 (2H, t, J=7.8 Hz, SO₂CH₂C̲H₂), 3.69 (3H, s, CH₃), 3.73 (3H, s, CH₃), 3.8 (2H, t, J=7.8 Hz, SO₂C̲H₂CH₂), 4.45 (2H, t, J=4.7 Hz, NHC̲H₂), 6.8-7 (4H, m, ArH, NH), 7.1-7.3 (5H, m, ArH), 8.38 (2H, s, SO₂NH₂).

$^{13}$C NMR (75 MHz, DMSO-D₆): 28.5 (SO₂CH₂C̲H₂), 50.3 (NHC̲H₂, d, J($^{19}$F—$^{13}$C)=12.5 Hz), 56.02 (CH₃), 56.08 (CH₃), 57.7 (SO₂C̲H₂CH₂), 112.31 (Ar), 112.34 (Ar), 115.8 (C4, dd, $^1$J($^{19}$F—$^{13}$C)=13 Hz, $^2$J($^{19}$F—$^{13}$C)=5 Hz), 120.8 (Ar), 127.5 (Ar), 128.1 (C1, t, J($^{19}$F—$^{13}$C)=16 Hz), 128.97 (Ar), 129.03 (Ar), 131.9 (Ar), 136 (C3, d, J($^{19}$F—$^{13}$C)=14 Hz), 137.5 (Ar), 137.7 (C5 or C6, dd, $^1$J($^{19}$F—$^{13}$C)=249 Hz, $^2$J($^{19}$F—$^{13}$C)=18 Hz), 145.1 (C2, d, J($^{19}$F—$^{13}$C)=256 Hz), 146 (C5 or C6, d, J($^{19}$F—$^{13}$C)=250 Hz), 148.9 (Ar), 149.4 (Ar).

$^{19}$F NMR (282 MHz, DMSO-D₆): −123.7 (C2-F, s), −134.8 (C6-F, dd, $^1$J=27 Hz, $^2$J=12 Hz), −150.4 (C5-F, dd, $^1$J=27 Hz, $^2$J=6 Hz).

HRMS calcd. for $C_{23}H_{23}F_3N_2O_6S_2$ [(M−H)⁻]: 543.0877. found: 543.0875.

The compound 9k. The product was purified by chromatography on a column of silica gel (0.04-0.063 mm) with EtAc:CHCl₃ (1:4), Rf=0.6. Recrystallization was accomplished from EtOH after chromatography. Yield: 0.12 g, 45%, mp 155° C.

$^1$H NMR (300 MHz, DMSO-D₆): 2.8-3 (4H, m, SO₂CH₂C̲H₂ and CH₂ of indane), 3.26 (1H, d, J=6.3 Hz, indane), 3.31 (1H, d, J=6.3 Hz, indane), 3.67 (2H, t, J=8 Hz, SO₂C̲H₂CH₂), 4.45-4.55 (1H, m, CH of indane), 6.87 (1H, d, J=8 Hz, NH), 7.1-7.3 (10H, m, ArH), 8.38 (2H, s, SO₂NH₂).

$^{13}$C NMR (75 MHz, DMSO-D₆): 28.4 (SO₂CH₂C̲H₂), 41.1 (CH₂ of indane, signal overlaps with signal of DMSO-D₆), 57.58 (SO₂C̲H₂CH₂), 57.7 (CH of indane, d, J($^{19}$F—$^{13}$C)=11 Hz), 115.3 (C4, dd, $^1$J($^{19}$F—$^{13}$C)=13 Hz, $^2$J($^{19}$F—$^{13}$C)=5 Hz), 125.4 (Ar), 127.38 (Ar), 127.45 (Ar), 128.2 (C1, t, J($^{19}$F—$^{13}$C)=16 Hz), 129 (Ar), 129.1 (Ar), 135.4 (C3, d, J($^{19}$F—$^{13}$C)=14 Hz), 137.5 (Ar), 137.6 (C5 or C6, dd, $^1$J($^{19}$F—$^{13}$C)=247 Hz, $^2$J($^{19}$F—$^{13}$C)=17 Hz), 141.1 (Ar), 144.4 (C2, d, J($^{19}$F—$^{13}$C)=252 Hz), 146.2 (C5 or C6, dd, $^1$J($^{19}$F—$^{13}$C)=250 Hz, $^2$J($^{19}$F—$^{13}$C)=16 Hz).

$^{19}$F NMR (282 MHz, DMSO-D₆): −126.1 (C2-F, s), −134.7 (C6-F, dd, $^1$J=27 Hz, $^2$J=12 Hz), −150.8 (C5-F, dd, $^1$J=27 Hz, $^2$J=7 Hz).

HRMS calcd. for $C_{23}H_{21}F_3N_2O_4S_2$ [(M+H)⁺]: 511.0968. found: 511.0972.

The compound 9l. The product was purified by chromatography on a column of silica gel (0.04-0.063 mm) with EtAc (5%):CHCl₃, Rf=0.38. Yield: 0.17 g, 66%, mp 90° C.

$^1$H NMR (300 MHz, DMSO-D₆): 2.0 (1H, sex, J=6 Hz, indane), 2.5 (1H, sex, indane, signal overlaps with signal of DMSO-D₆), 2.8-3.2 (4H, m, CH₂ of indane, SO₂CH₂C̲H₂), 3.7-3.9 (2H, m, SO₂C̲H₂CH₂), 5.18 (1H, br s, indane), 6.89 (1H, d, J=8 Hz, NH), 7.1-7.4 (9H, m, ArH), 8.43 (2H, s, SO₂NH₂).

$^{13}$C NMR (75 MHz, DMSO-D₆): 28.3 (SO₂CH₂C̲H₂), 30.2 (indane), 35.3 (indane), 57.8 (SO₂C̲H₂CH₂), 61.7 (CH of indane, d, J($^{19}$F—$^{13}$C)=11.4 Hz), 115.6 (C4, dd, $^1$J($^{19}$F-$^{13}$C)=14 Hz, $^2$J($^{19}$F—$^{13}$C)=5 Hz), 124.6 (Ar), 125.7 (Ar), 127.4 (Ar), 127.5 (Ar), 128.2 (C1, t, J($^{19}$F-$^{13}$C)=16 Hz), 128.9 (Ar), 129 (Ar), 129.1 (Ar), 135.7 (C3, d, J($^{19}$F—$^{13}$C)=15 Hz), 137.5 (Ar), 137.8 (C5 or C6, d, J($^{19}$F—$^{13}$C)=246 Hz), 143.7 (Ar), 144.2 (Ar), 144.8 (C2, d, J($^{19}$F—$^{13}$C)=252 Hz), 146.1 (C5 or C6, d, J($^{19}$F—$^{13}$C)=251 Hz).

$^{19}$F NMR (282 MHz, DMSO-D₆): −124.2 (C2-F, s), −134.5 (C6-F, dd, $^1$J=27 Hz, $^2$J=12 Hz), −150.2 (C5-F, dd, $^1$J=27 Hz, $^2$J=6 Hz).

HRMS calcd. for $C_{23}H_{21}F_3N_2O_4S_2$ [(M+H)⁺]: 511.0968. found: 511.0964.

The compound 9m. The product was purified by chromatography on a column of silica gel (0.04-0.063 mm) with EtAc:CHCl₃ (1:10), Rf=0.37. Yield: 0.13 g, 50%, mp 116-119° C.

$^1$H NMR (300 MHz, DMSO-D₆): 1.7-2.1 (4H, m, tetrahydronapthalene), 2.6-2.9 (2H, m, tetrahydronapthalene), 2.94 (2H, t, J=7.8 Hz, SO₂CH₂C̲H₂), 3.74 (2H, t, J=7.7 Hz, SO₂C̲H₂CH₂), 4.8-4.9 (1H, m, CH of tetrahydronapthalene), 6.82 (1H, d, J=9 Hz, NH), 7.1-7.4 (9H, m, ArH), 8.41 (2H, s, SO₂NH₂).

$^{13}$C NMR (75 MHz, DMSO-D₆): 19.1 (tetrahydronapthalene), 28.3 (SO₂CH₂C̲H₂), 29.1 (tetrahydronapthalene), 30.5 (tetrahydronapthalene), 54.1 (CH of tetrahydronapthalene, d, J($^{19}$F—$^{13}$C)=12 Hz), 58 (SO₂C̲H₂CH₂), 116.1 (C4, dd, $^1$J($^{19}$F—$^{13}$C) 13 Hz, $^2$J($^{19}$F—$^{13}$C)=5 Hz), 126.8 (Ar), 127.5 (Ar), 128.2 (Ar), 128.2 (C1, t, J($^{19}$F—$^{13}$C)=18 Hz, signal overlaps with signal of Ar), 129.03 (Ar), 129.08 (Ar), 129.5 (Ar), 129.9 (Ar), 135.3 (C3, d, J($^{19}$F—$^{13}$C)=11 Hz), 137.41 (Ar), 137.48 (Ar), 137.57 (Ar), 138 (C5 or C6, d, J($^{19}$F—$^{13}$C)=238 Hz), 145.1 (C2, d, J($^{19}$F-$^{13}$C)=254 Hz), 146.1 (C5 or C6, d, J($^{19}$F—$^{13}$C)=254 Hz).

$^{19}$F NMR (282 MHz, DMSO-D₆): −123.5 (C2-F, s), −134.3 (C6-F, dd, $^1$J=27 Hz, $^2$J=12 Hz), −149.9 (C5-F, dd, $^1$J=27 Hz, $^2$J=5 Hz).

HRMS calcd. for $C_{24}H_{23}F_3N_2O_4S_2$ [(M−H)⁻]: 523.0979. found: 523.0983.

Example 22. Preparation of 3-(1-adamantylamino)-2,5,6-trifluoro-4-[(2-phenylethyl)sulfonyl]benzenesulfonamide (Compound 9j), 3-{[(1S,2R)-2-hydroxy-1,2-diphenylethyl]amino}-2,5,6-trifluoro-4-[(2-phenylethyl)sulfonyl]benzenesulfonamide (Compound 9n), 3-{[(1R,2S)-2-hydroxy-1,2-diphenylethyl]amino}-2,5,6-trifluoro-4-[(2-phenylethyl)sulfonyl]benzenesulfonamide (Compound 9o)

The mixture of 2,3,5,6-tetrafluoro-4-[(2-phenylethyl)sulfonyl]benzenesulfonamide (compound 2q) (0.2 g, 0.5 mmol), Et₃N (0.071 mL, 0.51 mmol), DMSO (1 mL) and appropriate nucleophile (0.52 mmol) was stirred at ambient temperature for 3 days, compound 9j was obtained after stirring for 5 days. The mixture was then diluted with H₂O (20 mL).

The compound 9j. The resultant precipitate was filtered, washed with H₂O. The product was purified by chromatography on a column of silica gel (0.04-0.063 mm) with EtAc:CHCl$_3$ (1:4), Rf=0.75. Yield: 0.02 g, 8%, mp 155-156° C.

$^1$H NMR (300 MHz, CDCl$_3$): 1.69 (6H, br s, adamantane), 1.91 (6H, br s, adamantane), 2.15 (3H, br s, adamantane), 3.16 (2H, t, J=6 Hz, SO$_2$CH$_2$CH$_2$), 3.67 (2H, t, J=7 Hz, SO$_2$CH$_2$CH$_2$), 5.53 (2H, s, SO$_2$NH$_2$), 6.41 (1H, s, NH), 7.1-7.4 (5H, m, ArH).

$^{13}$C NMR (75 MHz, CDCl$_3$): 28.7 (SO$_2$CH$_2$CH$_2$), 30.2 (adamantane), 36.2 (adamantane), 43.4 (adamantane), 43.5 (adamantane), 56.6 (SO$_2$CH$_2$CH$_2$), 58.9 (adamantane, d, J($^{19}$F—$^{13}$C)=4 Hz), 119.6 (C4, dd, $^1$J($^{19}$F—$^{13}$C)=12 Hz, $^2$J($^{19}$F—$^{13}$C)=6 Hz), 126 (C1, t, J($^{19}$F—$^{13}$C)=16 Hz), 127.6 (Ar), 128.5 (Ar), 129.2 (Ar), 135.3 (C3, dd, $^1$J($^{19}$F—$^{13}$C) 18 Hz, $^2$J($^{19}$F—$^{13}$C)=3 Hz), 137 (Ar), 139 (C5 or C6, d, J($^{19}$F—$^{13}$C)=252 Hz), 146 (C5 or C6, d, J($^{19}$F—$^{13}$C)=254 Hz), 146.4 (C2, d, J($^{19}$F—$^{13}$C)=253 Hz).

$^{19}$F NMR (282 MHz, CDCl$_3$): −120.3 (C2-F, s), −137.6 (C6-F, dd, $^1$J=25 Hz, $^2$J=12 Hz), −152 (C5-F, dd, $^1$J=26 Hz, $^2$J=6 Hz).

HRMS calcd. for C$_{24}$H$_{27}$F$_3$N$_2$O$_4$S$_2$ [(M+H)$^+$]: 529.1437. found: 529.1440.

The compound 9n. The mixture was then extracted with EtAc (3×10 mL). The combined organic phase was dried over MgSO$_4$ and evaporated in vacuum. Recrystallization was accomplished from EtOH:H$_2$O=2:1. Yield: 0.12 g, 40%, mp 175-176° C.

$^1$H NMR (300 MHz, DMSO-D$_6$): 3.06 (2H, t, J=7.2 Hz, SO$_2$CH$_2$CH$_2$), 3.75-3.95 (2H, m, SO$_2$CH$_2$CH$_2$), 4.9-5 (1H, m, CH), 5.1 (1H, d, J=4.5 Hz, CH), 6 (1H, br s, OH), 7.1-7.3 (15H, m, ArH), 7.87 (1H, d, J=9 Hz, NH), 8.3 (2H, s, SO$_2$NH$_2$).

$^{13}$C NMR (75 MHz, DMSO-D$_6$): 28.5 (SO$_2$CH$_2$CH$_2$), 58 (SO$_2$CH$_2$CH$_2$), 65.4 (CH, d, J($^{19}$F—$^{13}$C)=12.8 Hz), 75.6 (CH), 115.3 (C4, dd, $^1$J($^{19}$F—$^{13}$C)=13 Hz, $^2$J($^{19}$F—$^{13}$C)=6 Hz), 127.2 (Ar), 127.4 (Ar), 127.8 (Ar), 127.9 (Ar), 128.2 (Ar), 128.3 (Ar), 128.93 (Ar), 128.99 (Ar), 129.04 (Ar), 135.2 (C3, d, J($^{19}$F—$^{13}$C)=12 Hz), 137.2 (C5 or C6, d, J($^{19}$F—$^{13}$C)=250 Hz), 137.5 (Ar), 139.7 (Ar), 142.9 (Ar), 144.5 (C2, d, J($^{19}$F—$^{13}$C)=254 Hz), 146 (C5 or C6, d, J($^{19}$F-$^{13}$C)=249 Hz).

$^{19}$F NMR (282 MHz, DMSO-D$_6$): −123.3 (C2-F, s), −134.7 (C6-F, dd, $^1$J=25 Hz, $^2$J=12 Hz), −150.8 (C5-F, dd, $^1$J=26 Hz, $^2$J=7 Hz).

HRMS calcd. for C$_{28}$H$_{25}$F$_3$N$_2$O$_5$S$_2$ [(M+H)$^+$]: 591.123. found: 591.1220.

The compound 9o. The resultant precipitate was filtered, washed with H$_2$O. Recrystallization was accomplished from EtOH:H$_2$O=2:1. Yield: 0.12 g, 40%, mp 176-177° C.

$^1$H NMR (300 MHz, DMSO-D$_6$): 3.06 (2H, t, J=7.2 Hz, SO$_2$CH$_2$CH$_2$), 3.75-3.95 (2H, m, SO$_2$CH$_2$CH$_2$), 4.9-5 (1H, m, CH), 5.1 (1H, t, J=4.2 Hz, CH), 6 (1H, d, J=4.2 Hz, OH), 7.1-7.3 (15H, m, ArH), 7.87 (1H, d, J=8 Hz, NH), 8.25 (2H, s, SO$_2$NH$_2$).

$^{13}$C NMR (75 MHz, DMSO-D$_6$): 28.5 (SO$_2$CH$_2$CH$_2$), 58 (SO$_2$CH$_2$CH$_2$), 65.4 (CH, d, J($^{19}$F—$^{13}$C)=12.8 Hz), 75.6 (CH), 115.3 (C4, dd, $^1$J($^{19}$F—$^{13}$C)=13 Hz, $^2$J($^{19}$F—$^{13}$C)=6 Hz), 127.2 (Ar), 127.4 (Ar), 127.8 (Ar), 127.9 (Ar), 128.2 (Ar), 128.3 (Ar), 128.93 (Ar), 128.99 (Ar), 129.04 (Ar), 135.2 (C3, d, J($^{19}$F—$^{13}$C)=12 Hz), 137.2 (C5 or C6, d, J($^{19}$F—$^{13}$C)=250 Hz), 137.5 (Ar), 139.7 (Ar), 142.9 (Ar), 144.5 (C2, d, J($^{19}$F—$^{13}$C)=254 Hz), 146 (C5 or C6, d, J($^{19}$F-$^{13}$C)=249 Hz).

$^{19}$F NMR (282 MHz, DMSO-D$_6$): −123.3 (C2-F, s), −134.7 (C6-F, dd, $^1$J=25 Hz, $^2$J=12 Hz), −150.8 (C5-F, dd, $^1$J=26 Hz, $^2$J=7 Hz).

HRMS calcd. for C$_{28}$H$_{25}$F$_3$N$_2$O$_5$S$_2$ [(M+H)$^+$]: 591.123. found: 591.1221.

Example 23. Preparation of 3-(benzylamino)-2,5,6-trifluoro-4-[(2-hydroxyethyl)sulfonyl]benzenesulfonamide (Compound 10a)

The mixture of 2,3,5,6-tetrafluoro-4-[(2-hydroxyethyl)sulfonyl]benzenesulfonamide (compound 2d) (0.25 g, 0.74 mmol), MeOH (10 mL) and benzylamine (0.17 mL, 1.56 mmol) was stirred at ambient temperature for 24 h. MeOH was evaporated in vacuum and the resultant precipitate was filtered, washed with H$_2$O. The product was purified by chromatography on a column of silica gel (0.04-0.063 mm) with EtAc:CHCl$_3$ (1:2), Rf=0.19. Yield: 0.11 g, 35%, mp 127° C.

$^1$H NMR (300 MHz, DMSO-D$_6$): 3.65 (2H, t, J=5.4 Hz, SO$_2$CH$_2$CH$_2$), 2.83 (2H, k, J=5.4 Hz, SO$_2$CH$_2$CH$_2$), 4.45-4.55 (2H, m, NHCH$_2$), 5.03 (1H, t, J=5.1 Hz, OH), 6.96 (1H, br t, NH), 7.3-7.5 (5H, m, ArH), 8.36 (2H, s, SO$_2$NH$_2$).

$^{13}$C NMR (75 MHz, DMSO-D$_6$): 50.7 (NHCH$_2$, d, J($^{19}$F—$^{13}$C)=13 Hz), 55.8 (SO$_2$CH$_2$CH$_2$), 60.1 (SO$_2$CH$_2$CH$_2$), 117.6 (C4, dd, $^1$J($^{19}$F—$^{13}$C)=13 Hz, $^2$J($^{19}$F—$^{13}$C)=5 Hz), 127.9 (C1 signal overlaps with signal of Ar), 128.1 (Ar), 128.3 (Ar), 129.3 (Ar), 136.1 (C3, d, J($^{19}$F—$^{13}$C)=13 Hz), 137.8 (C5 or C6, d, J($^{19}$F—$^{13}$C)=246 Hz), 139.6 (Ar), 144.9 (C2, d, J($^{19}$F—$^{13}$C)=252 Hz), 146.2 (C5 or C6, d, J($^{19}$F—$^{13}$C)=252 Hz).

$^{19}$F NMR (282 MHz, DMSO-D$_6$): −125.1 (C2-F, s), −135.3 (C6-F, dd, $^1$J=25 Hz, $^2$J=13 Hz), −150.7 (C5-F, dd, $^1$J=26 Hz, $^2$J=7 Hz).

HRMS calcd. for C$_{15}$H$_{15}$F$_3$N$_2$O$_5$S$_2$ [(M+H)$^+$]: 425.0447. found: 425.0439.

Example 24. Preparation of 3-(cyclooctylamino)-2,5,6-trifluoro-4-[(2-hydroxyethyl)sulfonyl]benzenesulfonamide (Compound 10b)

The mixture of 2,3,5,6-tetrafluoro-4-[(2-hydroxyethyl)sulfonyl]benzenesulfonamide (compound 2d) (0.38 g, 1.1 mmol), MeOH (10 mL) and cyclooctylamine (0.332 mL, 2.4 mmol) was refluxed for 6 h. MeOH was evaporated in vacuum and the resultant oil was washed with H$_2$O. The product was purified by chromatography on a column of silica gel (0.04-0.063 mm) with EtAc:CHCl$_3$ (1:1), Rf=0.38. Yield: 0.2 g, 40%.

$^1$H NMR (300 MHz, CDCl$_3$): 1.4-2 (14H, m, cyclooctane), 3.59 (2H, t, J=6 Hz, SO$_2$CH$_2$CH$_2$), 3.8-3.9 (1H, m, CH of cyclooctane), 4.11 (2H, t, J=6 Hz, SO$_2$CH$_2$CH$_2$), 6.08 (2H, s, SO$_2$NH$_2$), 6.74 (1H, br s, NH).

$^{13}$C NMR (75 MHz, CDCl$_3$): 23.5 (cyclooctane), 25.7 (cyclooctane), 27.4 (cyclooctane), 33.1 (cyclooctane), 56.3 (cyclooctane), 56.5 (SO$_2$CH$_2$CH$_2$), 59.8 (cyclooctane), 60.8 (SO$_2$CH$_2$CH$_2$), 115.8 (C4, dd, $^1$J($^{19}$F—$^{13}$C)=13 Hz, $^2$J($^{19}$F—$^{13}$C)=6 Hz), 126.5 (C1, t, J($^{19}$F—$^{13}$C)=16 Hz), 135.7 (C3, d, J($^{19}$F—$^{13}$C)=13 Hz), 137 (C5 or C6, dd, $^1$J($^{19}$F—$^{13}$C)=246 Hz, $^2$J($^{19}$F-$^{13}$C)=14 Hz), 144.7 (C2, d, J($^{19}$F—$^{13}$C)=253 Hz), 146.4 (C5 or C6, dd, $^1$J($^{19}$F—$^{13}$C)=253 Hz, $^2$J($^{19}$F—$^{13}$C)=16 Hz).

$^{19}$F NMR (282 MHz, CDCl$_3$): −125.9 (C2-F, s), −134 (C6-F, dd, $^1$J=25 Hz, $^2$J=12 Hz), −152.1 (C5-F, dd, $^1$J=24 Hz, $^2$J=4 Hz).

HRMS calcd. for C$_{16}$H$_{23}$F$_3$N$_2$O$_5$S$_2$ [(M+H)$^+$]: 445.1073. found: 445.1077.

Example 25. Preparation of 3-(cyclododecylamino)-2,5,6-trifluoro-4-[(2-hydroxyethyl)sulfonyl]benzenesulfonamide (Compound 10c), 3-[(2,6-dimethoxybenzyl)amino]-2,5,6-trifluoro-4-[(2-hydroxyethyl)sulfonyl]benzenesulfonamide (Compound 10d), 3-[(3,4-dimethoxybenzyl)amino]-2,5,6-trifluoro-4-[(2-hydroxyethyl)sulfonyl]benzenesulfonamide (Compound 10e), 3-[(1S)-2,3-dihydro-1H-inden-1-ylamino]-2,5,6-trifluoro-4-[(2-hydroxyethyl)sulfonyl]benzenesulfonamide (Compound 10f), 3-[(1S)-1,2,3,4-tetrahydronapthalen-1-ylamino)-2,5,6-trifluoro-4-[(2-hydroxyethyl)sulfonyl]benzenesulfonamide (Compound 10 g), 3-{[(1S,2R)-2-hydroxy-1,2-diphenylethyl]amino}-2,5,6-trifluoro-4-[(2-hydroxyethyl)sulfonyl]benzenesulfonamide (Compound 10 h)

The mixture of 2,3,5,6-tetrafluoro-4-[(2-hydroxyethyl)sulfonyl]benzenesulfonamide (compound 2d) (0.2 g, 0.59 mmol), DMSO (1 mL) and appropriate nucleophile (1.2 mmol) was stirred at ambient temperature for 24 h. The mixture was then diluted with $H_2O$ (20 mL) and extracted with EtAc (3×10 mL). The combined organic phase was dried over $MgSO_4$ and evaporated in vacuum.

The compound 10c. The product was purified by chromatography on a column of silica gel (0.04-0.063 mm) with EtAc:$CHCl_3$ (1:1), Rf=0.5. Yield: 0.26 g, 88%, mp 143-144° C.

$^1$H NMR (300 MHz, DMSO-$D_6$): 1.2-1.7 (22H, m, cyclododecane), 3.68 (2H, t, J=5 Hz, $SO_2CH_2CH_2$), 3.8 (1H, br s, CH of cyclododecane, signal overlaps with signal of $SO_2CH_2CH_2$), 3.83 (2H, t, J=5 Hz, $SO_2CH_2CH_2$), 5.01 (1H, t, J=5 Hz, OH), 6.55 (1H, d, J=9 Hz, NH), 8.36 (2H, s, $SO_2NH_2$).

$^{13}$C NMR (75 MHz, DMSO-$D_6$): 21.3 (cyclododecane), 23.4 (cyclododecane), 23.5 (cyclododecane), 24.4 (cyclododecane), 24.6 (cyclododecane), 30.8 (cyclododecane), 53.4 (CH of cyclododecane, d, J($^{19}$F—$^{13}$C)=12 Hz), 55.8 ($SO_2CH_2CH_2$), 60.3 ($SO_2CH_2CH_2$), 117.4 (C4, dd, $^1$J($^{19}$F—$^{13}$C)=13 Hz, $^2$J($^{19}$F—$^{13}$C)=6 Hz), 127.9 (C1, t, J($^{19}$F—$^{13}$C)=16 Hz), 135.7 (C3, d, J($^{19}$F—$^{13}$C)=13 Hz), 137.4 (C5 or C6, d, $^1$J($^{19}$F—$^{13}$C)=246 Hz, $^2$J($^{19}$F—$^{13}$C)=19 Hz), 144.7 (C2, d, J($^{19}$F—$^{13}$C)=253 Hz), 146.3 (C5 or C6, d, J($^{19}$F—$^{13}$C)=247 Hz).

$^{19}$F NMR (282 MHz, DMSO-$D_6$): −125.4 (C2-F, s), −134.8 (C6-F, dd, $^1$J=27 Hz, $^2$J=12 Hz), −151.4 (C5-F, dd, $^1$J=27 Hz, $^2$J=6 Hz).

HRMS calcd. for $C_{20}H_{31}F_3N_2O_5S_2$ [(M+H)$^+$]: 501.1699. found: 501.1701.

The compound 10d. The product was purified by chromatography on a column of silica gel (0.04-0.063 mm) with EtAc (60%):$CHCl_3$, Rf=0.45. Yield: 0.15 g, 52%, mp 164-165° C.

$^1$H NMR (300 MHz, DMSO-$D_6$): 3.35 (2H, t, J=6 Hz, $SO_2CH_2CH_2$), 3.63 (2H, br t, $SO_2CH_2CH_2$), 3.75 (6H, s, 2$CH_3$), 4.48 (2H, d, J=5.4 Hz, NH$CH_2$), 4.93 (1H, br s, OH), 6.58 (1H, br t, NH), 6.66 (2H, d, J=8.4 Hz, ArH), 7.26 (1H, t, J=8.4 Hz, ArH), 8.42 (2H, s, $SO_2NH_2$).

$^{13}$C NMR (75 MHz, DMSO-$D_6$): 39.5 (NH$CH_2$), 55.4 ($SO_2CH_2CH_2$), 56.3 (2$CH_3$), 59.9 ($SO_2CH_2CH_2$), 104.7 (Ar), 114.6 (Ar), 118.2 (C4, dd, $^1$J($^{19}$F—$^{13}$C)=12 Hz, $^2$J($^{19}$F—$^{13}$C)=5 Hz), 127.7 (C1, t, J($^{19}$F—$^{13}$C)=16 Hz), 130.3 (Ar), 136.8 (C3, d, J($^{19}$F—$^{13}$C)=11 Hz), 137.9 (C5 or C6, d, $^1$J($^{19}$F—$^{13}$C)=228 Hz), 146 (C2, d, J($^{19}$F—$^{13}$C)=253 Hz), 144.8 (C5 or C6, d, J($^{19}$F—$^{13}$C)=242 Hz), 158.7 (Ar).

$^{19}$F NMR (282 MHz, DMSO-$D_6$): −122.1 (C2-F, s), −135.9 (C6-F, dd, $^1$J=26 Hz, $^2$J=13 Hz), −150.1 (C5-F, dd, $^1$J=27 Hz, $^2$J=6 Hz).

HRMS calcd. for $C_{17}H_{19}F_3N_2O_7S_2$ [(M−H)$^-$]: 483.0513. found: 483.0517.

The compound 10e. The product was purified by chromatography on a column of silica gel (0.04-0.063 mm) with EtAc:$CHCl_3$ (2:1), Rf=0.38. Recrystallization was accomplished from EtOH after chromatography. Yield: 0.1 g, 29%, mp 164-165° C.

$^1$H NMR (300 MHz, DMSO-$D_6$): 3.65 (2H, t, J=6 Hz, $SO_2CH_2CH_2$), 3.746 (3H, s, $CH_3$), 3.755 (3H, s, $CH_3$), 3.82 (2H, br t, $SO_2CH_2CH_2$), 4.43 (2H, br s, NH$CH_2$), 6.8-7 (3H, m, ArH), 6.99 (1H, s, NH), 8.38 (2H, s, $SO_2NH_2$).

$^{13}$C NMR (75 MHz, DMSO-$D_6$): 50.6 (NH$CH_2$, d, J($^{19}$F—$^{13}$C)=12 Hz), 55.8 ($CH_3$), 56 ($CH_3$), 56.1 ($SO_2CH_2CH_2$), 60.1 ($SO_2CH_2CH_2$), 112.2 (Ar), 112.3 (Ar), 117.7 (C4, dd, $^1$J($^{19}$F—$^{13}$C)=13 Hz, $^2$J($^{19}$F—$^{13}$C)=5 Hz), 120.7 (Ar), 127.8 (C1, t, J($^{19}$F—$^{13}$C)=16 Hz), 131.8 (Ar), 136 (C3, d, J($^{19}$F—$^{13}$C)=16 Hz), 137.8 (C5 or C6, d, J($^{19}$F—$^{13}$C)=252 Hz), 145.1 (C2, d, J($^{19}$F—$^{13}$C)=253 Hz), 146.1 (C5 or C6, dd, $^1$J($^{19}$F—$^{13}$C)=253 Hz, $^2$J($^{19}$F—$^{13}$C)=16 Hz), 148.9 (Ar), 149.5 (Ar).

$^{19}$F NMR (282 MHz, DMSO-$D_6$): −124.4 (C2-F, s), −135.2 (C6-F, dd, $^1$J=27 Hz, $^2$J=12 Hz), −150.7 (C5-F, dd, $^1$J=27 Hz, $^2$J=6 Hz).

HRMS calcd. for $C_{17}H_{19}F_3N_2O_7S_2$ [(M−H)$^-$]: 483.0513. found: 483.0515.

The compound 10f. The product was purified by chromatography on a column of silica gel (0.04-0.063 mm) with EtAc:$CHCl_3$ (1:1), Rf=0.38. Yield: 0.16 g, 60%, mp 131-132° C.

$^1$H NMR (300 MHz, DMSO-$D_6$): 1.95 (1H, sex, J=7 Hz, indane), 2.51 (1H, sex, indane, signal overlaps with signal of DMSO-$D_6$), 2.8-3.1 (2H, m, indane), 3.55-3.7 (2H, m, $SO_2CH_2CH_2$), 3.7-3.85 (2H, m, $SO_2CH_2CH_2$), 5.02 (1H, t, J=5 Hz, OH), 5.1-5.25 (1H, m, CH of indane), 6.88 (1H, d, J=6 Hz, NH), 7.2-7.5 (4H, m, ArH), 8.43 (2H, s, $SO_2NH_2$).

$^{13}$C NMR (75 MHz, DMSO-$D_6$): 30.2 (indane), 35.2 (indane), 55.8 ($SO_2CH_2CH_2$), 60.2 ($SO_2CH_2CH_2$), 61.9 (CH of indane, d, J($^{19}$F—$^{13}$C)=12 Hz), 117.6 (C4, dd, $^1$J($^{19}$F—$^{13}$C)=13 Hz, $^2$J($^{19}$F—$^{13}$C)=5 Hz), 124.7 (Ar), 125.6 (Ar), 127.4 (Ar), 128 (C1, t, J($^{19}$F—$^{13}$C)=16 Hz), 128.9 (Ar), 135.6 (C3, d, J($^{19}$F—$^{13}$C)=12 Hz), 137.8 (C5 or C6, d, J($^{19}$F—$^{13}$C)=253 Hz), 144.4 (Ar), 144.5 (Ar), 144.8 (C2, d, J($^{19}$F—$^{13}$C)=251 Hz), 146.3 (C5 or C6, d, J($^{19}$F—$^{13}$C)=258 Hz).

$^{19}$F NMR (282 MHz, DMSO-$D_6$): −124.6 (C2-F, s), −134.8 (C6-F, dd, $^1$J=27 Hz, $^2$J=12 Hz), −150.7 (C5-F, dd, $^1$J=27 Hz, $^2$J=6 Hz).

HRMS calcd. for $C_{17}H_{17}F_3N_2O_5S_2$ [(M−H)$^-$]: 449.0458. found: 449.0461.

The compound 10 g. The product was purified by chromatography on a column of silica gel (0.04-0.063 mm) with EtAc:$CHCl_3$ (1:1), Rf=0.41. Yield: 0.14 g, 51%, mp 103-105° C.

$^1$H NMR (300 MHz, DMSO-$D_6$): 1.7-2.1 (4H, m, tetrahydronapthalene), 2.6-2.9 (2H, m, tetrahydronapthalene), 3.61 (2H, t, J=5.4 Hz, $SO_2CH_2CH_2$), 3.76 (2H, br t, $SO_2CH_2CH_2$), 4.8-4.9 (1H, m, CH of tetrahydronapthalene), 5.01 (1H, br s, OH), 6.82 (1H, d, J=9 Hz, NH), 7.1-7.3 (3H, m, ArH), 7.4 (1H, d, J=7.7 Hz, ArH), 8.42 (2H, s, $SO_2NH_2$).

$^{13}$C NMR (75 MHz, DMSO-$D_6$): 19.3 (tetrahydronapthalene), 29.2 (tetrahydronapthalene), 30.6 (tetrahydronapthalene), 54.3 (CH of tetrahydronapthalene, d, J($^{19}$F—$^{13}$C)=12 Hz), 55.7 ($SO_2CH_2CH_2$), 60.3 ($SO_2CH_2CH_2$), 117.9 (C4, dd, $^1$J($^{19}$F—$^{13}$C)=13 Hz, $^2$J($^{19}$F—$^{13}$C)=5 Hz), 126.8 (Ar), 128 (C1, t, J($^{19}$F—$^{13}$C)=16 Hz), 128.2 (Ar), 129.5 (Ar), 129.8 (Ar), 135.1 (C3, d, J($^{19}$F—$^{13}$C)=15 Hz), 137.48 (Ar), 137.56 (Ar), 137.9 (C5 or C6, d, J($^{19}$F—$^{13}$C)=245 Hz), 145.1 (C2, d, J($^{19}$F—$^{13}$C)=255 Hz), 146.2 (C5 or C6, d, J($^{19}$F—$^{13}$C)=254 Hz).

$^{19}$F NMR (282 MHz, DMSO-D$_6$): −123.9 (C2-F, s), −134.5 (C6-F, dd, $^1$J=27 Hz, $^2$J=12 Hz), −150.5 (C5-F, dd, $^1$J=27 Hz, $^2$J=6 Hz).

HRMS calcd. for C$_{18}$H$_{19}$F$_3$N$_2$O$_5$S$_2$ [(M+H)$^+$]: 465.076. found: 465.0760.

The compound 10 h. The product was purified by chromatography on a column of silica gel (0.04-0.063 mm) with EtAc:CHCl$_3$ (2:1), Rf=0.53. Yield: 0.12 g, 39%.

$^1$H NMR (300 MHz, CD$_3$OD): 3.62 (2H, k, J=5.4 Hz, SO$_2$CH$_2$CH$_2$), 4.04 (2H, k, J=5.4 Hz, SO$_2$CH$_2$CH$_2$), 4.88 (SO$_2$NH$_2$, NH, OH signals overlap with signal of H$_2$O), 5.07 (1H, dd, $^1$J=5.1 Hz, $^2$J=2.1 Hz, CH), 5.14 (1H, d, J=4.8 Hz, CH), 7.1-7.3 (10H, m, ArH).

$^{13}$C NMR (75 MHz, CD$_3$OD): 55.5 (SO$_2$CH$_2$CH$_2$), 59.8 (SO$_2$CH$_2$CH$_2$), 65.7 (CH, d, J($^{19}$F-$^{13}$C)=12.5 Hz), 76.3 (CH), 116.8 (C4, dd, $^1$J($^{19}$F—$^{13}$C)=13 Hz, $^2$J($^{19}$F—$^{13}$C)=5.4 Hz), 126.8 (Ar), 127.33 (Ar), 127.38 (Ar), 127.7 (Ar), 128.8 (Ar), 128.5 (Ar), 135 (C3, d, J($^{19}$F—$^{13}$C)=14 Hz), 137.7 (C5 or C6, d, J($^{19}$F—$^{13}$C)=250 Hz), 139.1 (Ar), 141.7 (Ar), 144.8 (C2, d, J($^{19}$F—$^{13}$C)=257 Hz), 146.1 (C5 or C6, d, J($^{19}$F—$^{13}$C)=247 Hz).

$^{19}$F NMR (282 MHz, CD$_3$OD): −123.9 (C2-F, s), −136.4 (C6-F, dd, $^1$J=25 Hz, $^2$J=12 Hz), −152.3 (C5-F, dd, $^1$J=24 Hz, $^2$J=6 Hz).

HRMS calcd. for C$_{22}$H$_{21}$F$_3$N$_2$O$_6$S$_2$ [(M+H)$^+$]: 531.0866. found: 531.0865.

Example 26. Preparation of 3,5-bis(cyclooctylamino)-2,6-difluoro-4-[(2-phenylethyl)sulfonyl]benzenesulfonamide (Compound 11)

The mixture of 2,3,5,6-tetrafluoro-4-[(2-phenylethyl)sulfonyl]benzenesulfonamide (compound 2q) (0.2 g, 0.5 mmol), Et$_3$N (0.142 mL, 1.02 mmol), DMSO (1 mL) cyclooctylamine (0.142 mL, 1.02 mmol) was stirred at 60° C. for 32 h. The mixture was then diluted with H$_2$O (20 mL) and extracted with EtAc (3×10 mL). The combined organic phase was dried over MgSO$_4$ and evaporated in vacuum. The product was purified by chromatography on a column of silica gel (0.04-0.063 mm) with EtAc (10%):CHCl$_3$, Rf=0.72. Yield: 0.15 g, 48%.

$^1$H NMR (300 MHz, CDCl$_3$): 1.4-2 (28H, m, cyclooctane), 3.05-3.15 (2H, m, SO$_2$CH$_2$CH$_2$), 3.5-3.6 (2H, m, SO$_2$CH$_2$CH$_2$), 3.88 (2H, br s, 2×CH of cyclooctane), 5.58 (2H, s, SO$_2$NH$_2$), 6.43 (2H, br s, 2NH), 7.1-7.4 (5H, m, ArH).

$^{13}$C NMR (75 MHz, CDCl$_3$): 23.8 (cyclooctane), 25.8 (cyclooctane), 27.4 (cyclooctane), 28.5 (SO$_2$CH$_2$CH$_2$), 33.5 (cyclooctane), 55.9 (SO$_2$CH$_2$CH$_2$), 56.2 (CH of cyclooctane, t, J=6 Hz), 111.1 (C4, t, J($^{19}$F—$^{13}$C)=5 Hz), 126.3 (C1, t, J($^{19}$F—$^{13}$C)=16 Hz), 127.4 (Ar), 128.6 (Ar), 129.2 (Ar), 135.3 (C3, dd, $^1$J($^{19}$F—$^{13}$C)=10 Hz, $^2$J($^{19}$F—$^{13}$C)=6 Hz), 137.3 (Ar), 139.4 (C2, dd, $^1$J($^{19}$F—$^{13}$C)=244 Hz, $^2$J($^{19}$F—$^{13}$C)=4.5 Hz).

$^{19}$F NMR (282 MHz, CDCl$_3$): −144.1 (2F, s).

HRMS calcd. for C$_{30}$H$_{43}$F$_2$N$_3$O$_4$S$_2$ [(M+H)$^+$]: 612.2736. found: 612.2729.

Example 27. Preparation of 3,5-bis[(3,4-dimethoxybenzyl)amino]-2,6-difluoro-4-[(2-hydroxyethyl)sulfonyl]benzenesulfonamide (Compound 12)

The mixture of 2,3,5,6-tetrafluoro-4-[(2-hydroxyethyl)sulfonyl]benzenesulfonamide (compound 2d) (0.2 g, 0.59 mmol), DMSO (1 mL) and 3,4-dimethoxybenzylamine (0.359 mL, 2.38 mmol) was stirred at ambient temperature for 5 days. The mixture was then diluted with H$_2$O (20 mL), the resultant precipitate was filtered, washed with H$_2$O. Recrystallization was accomplished from EtOH. Yield: 0.2 g, 53%, mp 99-102° C.

$^1$H NMR (300 MHz, DMSO-D$_6$): 3.4 (SO$_2$CH$_2$CH$_2$, signal overlaps with signal of H$_2$O), 3.65 (2H, k, J=6 Hz, SO$_2$CH$_2$CH$_2$), 3.75 (12H, s, 4CH$_3$), 4.4 (4H, d, J=5 Hz, 2NH CH$_2$), 5.04 (1H, t, J=5.4 Hz, OH), 6.38 (2H, t, J=5.7 Hz, 2NH), 6.85-7.05 (6H, m, ArH), 8.15 (2H, s, SO$_2$NH$_2$).

$^{13}$C NMR (75 MHz, DMSO-D$_6$): 51.2 (NHCH$_2$, t, J($^{19}$F—$^{13}$C)=6 Hz), 55.5 (SO$_2$CH$_2$CH$_2$), 56.07 (CH$_3$), 56.18 (CH$_3$), 58.3 (SO$_2$CH$_2$CH$_2$), 112.4 (Ar), 115.5 (C4, t, J($^{19}$F—$^{13}$C)=3 Hz), 120.8 (Ar), 127.9 (C1, t, J($^{19}$F—$^{13}$C)=16 Hz), 132.3 (Ar), 135.7 (C3, dd, $^1$J($^{19}$F—$^{13}$C)=10 Hz, $^2$J($^{19}$F-$^{13}$C)=6 Hz), 141.7 (C2, dd, $^1$J($^{19}$F—$^{13}$C)=247 Hz, $^2$J($^{19}$F—$^{13}$C)=4 Hz), 148.8 (Ar), 149.4 (Ar).

$^{19}$F NMR (282 MHz, DMSO-D$_6$): −133.47 (2F, s).

HRMS calcd. for C$_{26}$H$_{31}$F$_2$N$_3$O$_9$S$_2$ [(M+H)$^+$]: 632.1543. found: 632.1548.

Compound Binding and Inhibition Measurements

Inhibition of carbonic anhydrases is measured by determining the reduction in the velocity of catalysis. Carbonic anhydrases catalyse the reversible reaction:

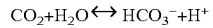

$$CO_2 + H_2O \leftrightarrow HCO_3^- + H^+$$

The inhibition of this reaction may be determined by measuring carbon dioxide consumption, bicarbonate appearance and the changes of pH (Krebs, J. F. and Fierke, C. A. (1993), *J. Biol. Chem.* 268, 948). All sulfonamides bind to the active center of carbonic anhydrases and diminish this reaction. Inhibition is equivalent to binding. (Chakravarty, S. and. Kannan, K. K. (1994), *J. Mol. Biol.* 243, 298; Lindskog, S. (1997), *Pharmacol. Ther.* 74, 1; Baird, T. T. J. et al. (1997), *Biochemistry*, 36, 2669). However, their binding and inhibitory efficiency varies greatly. Furthermore, the specificity of various sulfonamides varies greatly (Alterio, V. et al. (2012), *Chem. Rev.* 112, 4421). Sulfonamide binding to carbonic anhydrases is measured by a number of methods (Krishnamurthy, V. M. et al. (2008), *Chem. Rev.* 108, 946). Most often used methods are isothermal titration calorimetry, surface plasmon resonance, and ultracentrifugation. (Myszka, D. G. et al. (2003), *J. Biomol. Tech.* 14, 247). Specificity is determined by measuring binding constants with various isozymes and also by measuring intrinsic binding constants (Matulis, D. and Todd, M. J. (2004), *Biocalorimetry* 2).

Example 28. Determination of the Observed Binding Constants by the Fluorescent Thermal Shift Assay (TSA)

Inhibitor binding to carbonic anhydrases was measured by the fluorescent thermal shift assay, which measures the binding constant of a ligand by determining the increase in the melting temperature of the protein in the presence of a ligand. TSA experiments were performed as previously described (Čapkauskaitė, E. et al. (2012), *Eur. J. Med. Chem.* 51, 259). TSA data were fit and analyzed as previously described (Kazlauskas, E. et al. (2012), *PLoS ONE*, 7, e36899).

FIG. 1 shows representative binding data obtained by TSA (isozyme CA XIII). The dissociation constants for several selected characteristic compounds are listed in Table 1. A widely used CA inhibitors acetazolamide (AZM) and ethoxzolamide (EZA) were used as controls in these experiments. The data in the Table show that the number of fluorine atom substitutions and the nature of the substituent on the benzene ring significantly influences the binding affinity against CA I, CA II, CA VII, CA XII and CA XIII isoforms. The 4-substituted-2,3,5,6-tetrafluorobenzenesulfonamides (compounds 2a-x) bind CAI, II, VII and XIII isozymes with low nanomolar and subnanomolar affinity, exhibiting especially strong binding of CA I ($K_d$ is in the range of 0.01-14 nM). The weakest binding is with CA XII ($K_d$ is in the range of 20-769 nM). Further substitution at position 2 (compounds 3a-o, 4a-g, 5, 6) significantly lowers affinity for all CA isozymes, especially for CAI (the binding is in the micromolar range). Compounds 4a-g (Table lists 4e) demonstrate high selectivity for hCA XIII with respect to the other isoforms, CA I, II, VII and XII. Compounds 8a-f (Table lists 8a) do not have substituent at position 4 and fluorine atom at position 2 is substituted by a bulky group. They bind stronger to CAI then the same compounds having substituent at position 4 (compounds 4a-f). Compounds 9a-o having substitution at position 3 are good inhibitors of CA XIII. It seems that binding to CA XIII does not strongly depend on the size of substituent at this position because $K_d$ varies only in the narrow nanomolar range (from 1.3 nM for 9a to 8.3 nM for 9 h). Compounds 10a-h act as nanomolar inhibitors of CA II, CA VII, CA XII, and CA XIII.

TSA data of a selected representative compound binding to CA XIII (FIG. 1). Panels on the top show thermal shift assay raw data of 2c and 9c binding to CA XIII. Panel on the bottom show the dependence of the protein melting temperatures $T_m$ on ligand concentrations. The curves in this panel show the simulated curves according to literature model.

TABLE 1

Dissociation constants of selected compound binding to five human recombinant CA isoforms as determined by TSA (37° C., pH 7.0).

| Compound | Dissociation constants $K_d$ (nM) to CA isoforms | | | | |
|---|---|---|---|---|---|
| 1 | CA I 2 | CA II 3 | CA VII 4 | CA XII 5 | CA XIII 6 |
| 2a | 8.3 | 91.0 | 465 | 769 | 140 |
| 2c | 0.11 | 6.7 | 45.5 | 222 | 8.3 |
| 2d | 0.20 | 17.0 | 7.1 | 250 | 29.0 |
| 2g | 0.20 | 11.0 | 5.0 | 50.0 | 6.7 |
| 2h | 0.40 | 20.0 | 10.0 | 91.0 | 20.0 |
| 2i | 0.10 | 67.0 | 147 | 200 | 14.3 |
| 2j | 0.13 | 4.0 | 11.8 | 20.0 | 1.5 |
| 2l | 0.10 | 2.5 | 1.0 | 50.0 | 1.0 |
| 2m | 0.25 | 1.25 | 1.25 | 6.67 | 0.40 |
| 2t | 2.5 | 10.0 | 10.0 | 290 | 2.5 |
| 2u | 1.1 | 1.1 | 0.22 | 200 | 0.25 |
| 2w | 0.40 | 6.7 | 13.0 | 110 | 2.5 |
| 2x | 14.0 | 6.7 | 1.7 | 670 | 2.0 |
| 3a | 3 300 | 500 | 130 | 2 900 | 67.0 |
| 3d | 1 700 | 3 300 | 4 000 | 5 000 | 40.0 |
| 3f | 25 000 | 250 | 170 | 500 | 500 |
| 3l | 5 000 | 3 300 | 4 000 | 1 700 | 100 |
| 4e | 8 300 | 2 780 | 1 100 | 1 250 | 33.3 |
| 8a | 167 | 200 | 167 | 833 | 100 |
| 9a | 67.0 | 5.9 | 8.3 | 290 | 1.3 |
| 9c | 56.0 | 6.7 | 5.0 | 40.0 | 2.5 |
| 9d | 500 | 17.0 | 4.0 | 33.0 | 6.7 |
| 9h | 58.8 | 22.2 | 667 | 167 | 8.3 |
| 9i | 213 | 22.2 | 6.7 | 250 | 3.3 |
| 9j | 500 | 50.0 | 5.0 | 17.0 | 5.6 |
| 9n | 1 700 | 33.0 | 10.0 | 250 | 5.6 |
| 9o | 770 | 91.0 | 40.0 | 400 | 6.7 |

TABLE 1-continued

Dissociation constants of selected compound binding to five human recombinant CA isoforms as determined by TSA (37° C., pH 7.0).

| Compound | Dissociation constants $K_d$ (nM) to CA isoforms | | | | |
|---|---|---|---|---|---|
| 1 | CA I 2 | CA II 3 | CA VII 4 | CA XII 5 | CA XIII 6 |
| 10a | 200 | 83.0 | 130 | 25.0 | 14.0 |
| 10d | 200 | 16.7 | 40.0 | 66.7 | 25.0 |
| 10e | 83.3 | 25.0 | 14.3 | 66.7 | 4.3 |
| EZA | 14 | 0.71 | 0.71 | 36 | 13.0 |
| AZM | 1400 | 17.0 | 17.0 | 133 | 50.0 |

Example 29. Determination of the Binding Constants by Isothermal Titration Calorimetry (ITC)

The heat evolved upon inhibitor binding to carbonic anhydrase isozymes was measured by isothermal titration calorimetry. ITC measurements were performed as previously described (Čapkauskaitė, E. et al. (2012), *Eur. J. Med. Chem.* 51, 259).

Figure 2:
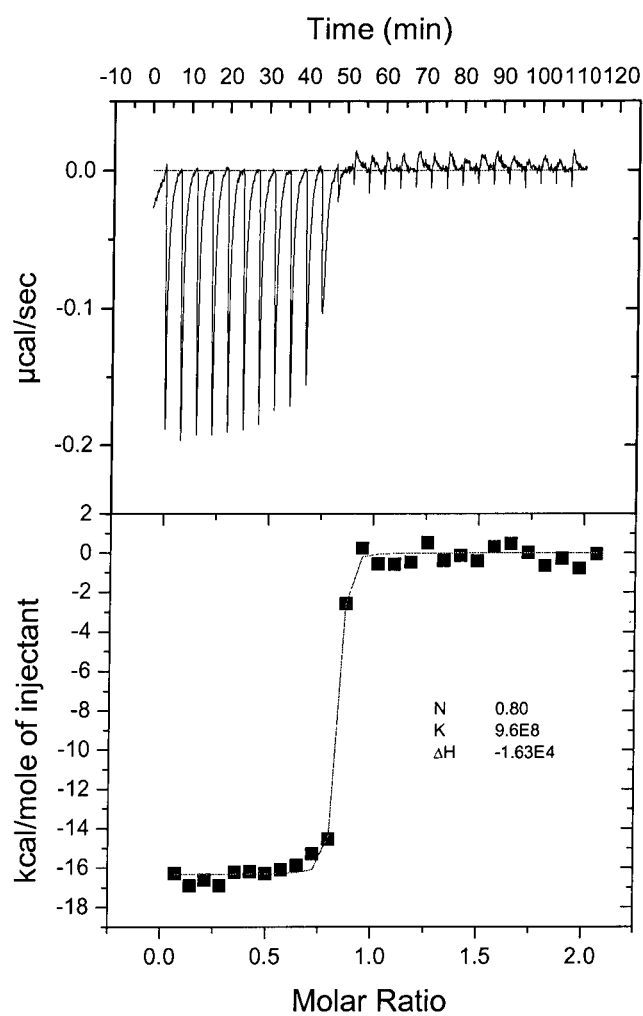
Figure 3:
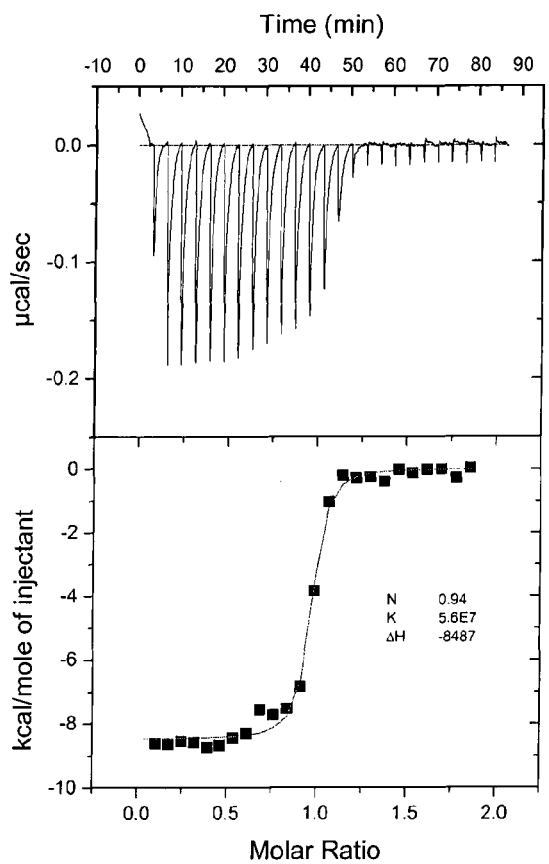

FIGS. 2, 3 show representative binding data obtained by ITC (isozymes CA I and CA XIII). The binding of 2d to CA I is the case of very tight binding where ITC curve is too steep to be fitted precisely. Therefore TSA data is more reliable to determine tight binding than ITC. The observed dissociation constants for compounds 2t and 10a listed in Table 2 shows the negligible differences between observed $K_d$'s measured by two methods (see TSA data in Table 1). Due to laborious nature of ITC measurements, only two compounds were tested by ITC and demonstrated that there is good agreement between TSA and ITC data.

FIG. 2 shows ITC data of 2d binding to CA I. FIG. 3 shows ITC data of 2c binding to CA XIII.

TABLE 2

Dissociation constants of selected compound binding to five human recombinant CA isoforms as determined by ITC (37° C., pH 7.0).

| Compound | Dissociation constants $K_d$ (nM) to CA isoforms | | | | |
|---|---|---|---|---|---|
|  | CA I | CA II | CA VII | CA XII | CA XIII |
| 2t | 5.2 | 9.4 | 88.5 | 149 | 4.7 |
| 10a | 130 | 139 | 405 | 12.2 | 45.2 |
| EZA | 25.0 | 0.38 | 8.8 | 23.0 | 12.0 |
| AZM | 780 | 17.7 | 83.3 | 79.2 | 64.4 |

Example 30. Determination of the Compound Inhibition Constants $K_i$ by $CO_2$ Hydration Assay In addition to the binding measurements by TSA and ITC, inhibition constants were also determined by conventional hydration inhibition assay for several selected characteristic compounds and confirmed that there is good general agreement between TSA, ITC, and inhibition data.

Figure 4:
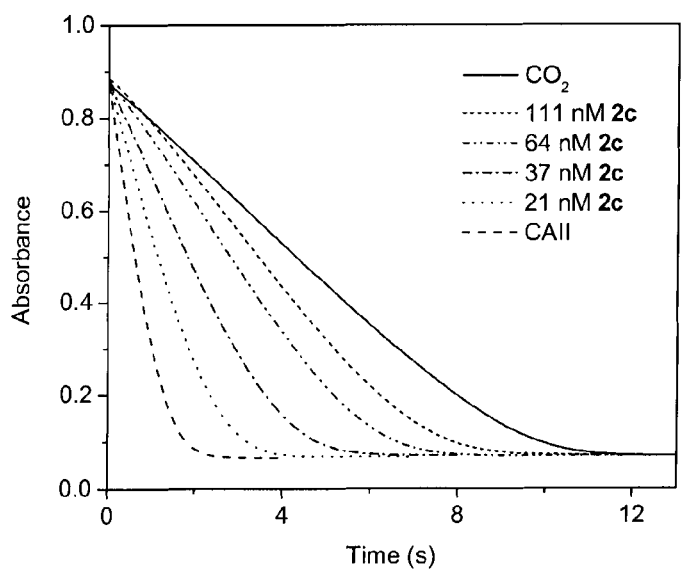
Figure 5:
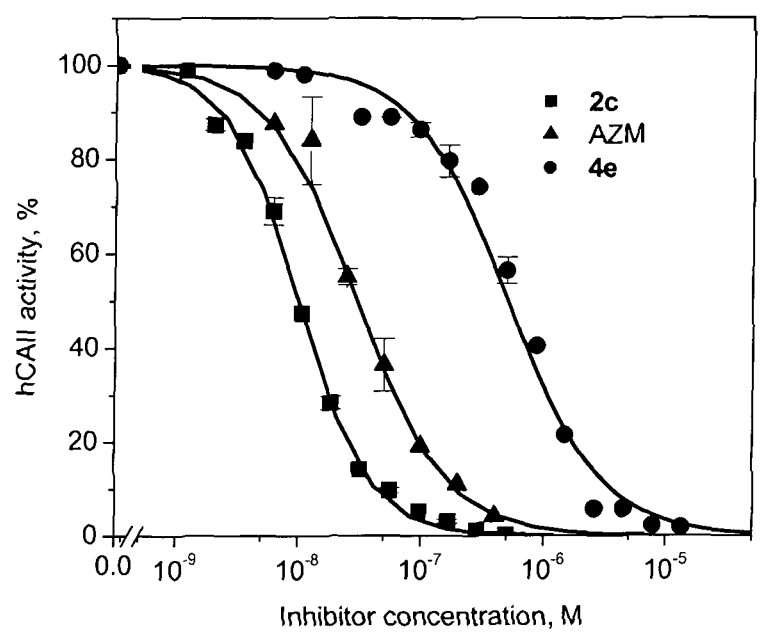

The carbon dioxide hydration activity of recombinant human CAII was measured using Applied Photophysics SX.18MV-R stopped-flow spectrometer. Reaction velocities were measured by recording absorbance of bromothymol blue (40 μM). The reaction buffer contained 10 mM NaCl, 10 mM Hepes, pH 7.4. Saturated $CO_2$ solutions were made by bubbling gas in milli-Q water at 25° C. CAII was incubated with inhibitors for 15 min at a room temperature to form enzyme-inhibitor complex. CAII concentration was 20 nM and final DMSO concentration was less than 0.04%. IC50 value was determined by fitting the sigmoidal curve on the data points and then $K_i$ was calculated using Cheng-Prusoff equation. The determined $K_i$ values for 2c, 4e, and AZM were 3.5, 500, and 10.6 nM, respectively (FIGS. 4 and 5). These values are systematically lower than the ones determined by TSA, but essentially within the standard deviation and the random error of both methods.

FIG. 4 shows $CO_2$ hydration catalyzed by CA II and inhibition by 2c. FIG. 5 shows inhibition curves of CA II with 2c, AZM and 4e.

Newly synthesized sulfonamides of general formula (I)

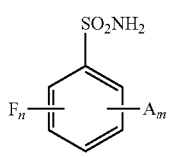

(I)

exhibit significant affinity and selectivity, often better than the existing compounds, promising to help in solving the issue of non-specific binding of clinically used inhibitors.

The invention claimed is:
1. Fluorinated benzenesulfonamides of general formula (I)

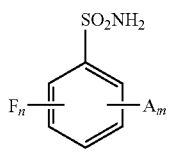

(I)

where
n is 2 or 3, the fluorine atoms are in any position,
m is 2 or 3, the A groups are identical or different from each other,
n+m must be equal to 5,
A is selected from the group consisting of $R^1$, OH, $OR^1$, SH, $SR^1$, $S(O)R^1$, $SO_2R^1$, $C(O)R^1$, $C(O)OR^1$, $OC(O)R^1$, $NHR^1$, $N(R^1)_2$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1O(O)NHR^1$, $NR^1C(O)N(R^1)_2$, $SO_2NHR^1$, $SO_2N(R^1)_2$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, Cl, Br, I, CN, $NO_2$, $N_3$, C(O)H, CHNOH, $CH(NOCH_3)$, $CF_3$, $CF_2CF_3$, $OCF_3$, $OCF_2CF_3$, and $C(O)NH_2$,
$R^1$ is $R^2$, $R^3$, $R^4$, $R^5$, $R^6$, $R^7$,
$R^2$ is phenyl, which is unfused or fused with benzene, heteroarene, cycloalkane or heterocycloalkane,
$R^3$ is heteroaryl, which is unfused or fused with benzene, heteroarene, cycloalkane or heterocycloalkane,
$R^4$ is cycloalkyl, cycloalkenyl, cycloalkynyl, heterocycloalkyl, heterocycloakenyl or heterocycloakynyl, each of which is unfused or fused with benzene, heteroarene,
$R^5$ is alkyl, alkenyl or alkynyl each of which is unsubstituted or substituted by one or more identical or different groups selected from the group consisting of $R^8$, OH, $OR^8$, SH, $SR^8$, $S(O)R^8$, $SO_2R^8$, $C(O)R^8$, $C(O)OR^8$, $OC(O)R^8$, $NHR^8$, $N(R^8)_2$, $C(O)NHR^8$, $C(O)N(R^8)_2$, $NHC(O)R^8$, $NR^8C(O)R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $SO_2NHR^8$, $SO_2N(R^8)_2$, $NR^8SO_2R^8$, $NHSO_2NHR^8$, $NHSO_2N(R^8)_2$, $NR^8SO_2NHR^8$, $NR^8SO_2N(R^8)_2$, C(O)NHNOH, $C(O)NHNOR^8$, $C(O)NHSO_2R^8$, $C(NH)NH_2$, $C(NH)NHR^8$, $C(NH)N(R^8)_2$, $NHSO_2NHR^8$, $NHSO_2N(CH_3)R^8$, $N(CH_3)SO_2N(CH_3)R^8$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, and $C(O)NH_2$,
$R^8$ is $R^9$, $R^{10}$, $R^{11}$, $R^{12}$, $R^{13}$, $R^{14}$,
$R^9$ is phenyl, which is unfused or fused with benzene, heteroarene, cycloalkane or heterocycloalkane,
$R^{10}$ is heteroaryl, which is unfused or fused with benzene, heteroarene, cycloalkane or heterocycloalkane,
$R^{11}$ is cycloalkyl, cycloalkenyl, cycloalkynyl, heterocycloalkyl, heterocycloakenyl or heterocycloakynyl, each of which is unfused or fused with benzene, heteroarene,
$R^{12}$ is alkyl, alkenyl or alkynyl each of which is unsubstituted or substituted by one or more identical or different groups selected from the group consisting of
$NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I,
$R^{13}$ is phenyl which is unsubstituted or substituted by one or more identical or different groups selected from the group consisting of
$NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I,
$R^{14}$ is heteroaryl, which is unsubstituted or substituted by one or more identical or different groups selected from the group consisting of
$NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, C(O)H, C(O)OH, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I,
$R^6$ is phenyl which is unsubstituted or substituted by one or more identical or different groups selected from the group consisting of $R^{15}$, OH, $OR^{15}$, SH, $SR^{15}$, $S(O)R^{15}$, $SO_2R^{15}$, $C(O)R^{15}$, $C(O)OR^{15}$, $OC(O)R^{15}$, $NHR^{15}$, $N(R^{15})_2$, $C(O)NHR^{15}$, $C(O)N(R^{15})_2$, $NHC(O)R^{15}$, $NR^{15}C(O)R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $SO_2NHR^{15}$, $SO_2N(R^{15})_2$, $NR^{15}SO_2R^{15}$, $NHSO_2NHR^{15}$, $NHSO_2N(R^{15})_2$, $NR^{15}SO_2NHR^{15}$, $NR^{15}SO_2N(R^{15})_2$, C(O)NHNOH, $C(O)NHNOR^{15}$, $C(O)NHSO_2R^{15}$, $C(NH)NH_2$, $C(NH)NHR^{15}$, $C(NH)N(R^{15})_2$, $NHSO_2NHR^{15}$, $NHSO_2N(CH_3)R^{15}$, $N(CH_3)SO_2N(CH_3)R^{15}$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, and $C(O)NH_2$,
$R^{15}$ is $R^{16}$, $R^{17}$, $R^{18}$, $R^{19}$, $R^{20}$, $R^{21}$,
$R^{16}$ is phenyl, which is unfused or fused with benzene, heteroarene, cycloalkane or heterocycloalkane, $R^{17}$ is heteroaryl, which is unfused or fused with benzene, heteroarene, cycloalkane or heterocycloalkane, $R^{18}$ is cycloalkyl, cycloalkenyl, cycloalkynyl, heterocycloalkyl, heterocycloakenyl or heterocycloakynyl, each of which is unfused or fused with benzene, heteroarene, $R^{19}$ is alkyl, alkenyl or alkynyl each of which is unsubstituted or substituted by one or more identical or different groups selected from the group consisting of $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I, $R^{20}$ is phenyl which is unsubstituted or substituted by one or more identical or different groups selected from the group consisting of $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I, $R^{21}$ is heteroaryl, which is unsubstituted or substituted by one or more identical or different groups selected from the group consisting of $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I, $R^7$ is heteroaryl, which is unsubstituted or substituted by one or more identical or different groups selected from $R^{22}$, OH, $OR^{22}$, SH, $SR^{22}$, $S(O)R^{22}$, $SO_2R^{22}$, $C(O)R^{22}$, $C(O)OR^{22}$, $OC(O)R^{22}$, $NHR^{22}$, $N(R^{22})_2$, $C(O)NHR^{22}$, $C(O)N(R^{22})_2$, $NHC(O)R^{22}$, $NR^{22}C(O)R^{22}$, $NHC(O)OR^{22}$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $SO_2NHR^{22}$, $SO_2N(R^{22})_2$, $NR^{22}SO_2R^{22}$, $NHSO_2NHR^{22}$, $NHSO_2N(R^{22})_2$, $NR^{22}SO_2NHR^{22}$, $NR^{22}SO_2N(R^{22})_2$, $C(O)NHNOH$, $C(O)NHNOR^{22}$, $C(O)NHSO_2R^{22}$, $C(NH)NH_2$, $C(NH)NHR^{22}$, $C(NH)N(R^{22})_2$, $NHSO_2NHR^{22}$, $NHSO_2N(CH_3)R^{22}$, $N(CH_3)SO_2N(CH_3)R^{22}$, F, Cl, Br, I, CN, $NO_2$, $N_3$, $C(O)H$, CHNOH, $CH(NOCH_3)$, $CF_3$, $CF_2CF_3$, $OCF_3$, $OCF_2CF_3$, $C(O)OH$, $C(O)NH_2$, $R^{22}$ is $R^{23}$, $R^{24}$, $R^{25}$, $R^{26}$, $R^{27}$, $R^{28}$, $R^{23}$ is phenyl, which is unfused or fused with benzene, heteroarene, cycloalkane or heterocycloalkane, $R^{24}$ is heteroaryl, which is unfused or fused with benzene, heteroarene, cycloalkane or heterocycloalkane, $R^{25}$ is cycloalkyl, cycloalkenyl, cycloalkynyl, heterocycloalkyl, heterocycloakenyl or heterocycloakynyl, each of which is unfused or fused with benzene, heteroarene, $R^{26}$ is alkyl, alkenyl or alkynyl each of which is unsubstituted or substituted by one or more identical or different groups selected from the group consisting of $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I, $R^{27}$ is phenyl which is unsubstituted or substituted by one or more identical or different groups selected from the group consisting of $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I, $R^{28}$ is heteroaryl, which is unsubstituted or substituted by one or more identical or different groups selected from the group consisting of $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, and I, and/or pharmaceutically acceptable salts of the sulfonamides of general formula (I) thereof.

2. The fluorinated benzenesulfonamides according to claim 1, selected from the group consisting of:

2-(isopropylamino)-3,5,6-trifluoro-4-[(2-phenylethyl)thio]benzenesulfonamide;

2-(benzylamino)-3,5,6-trifluoro-4-[(2-phenylethyl)thio]benzenesulfonamide;

2-[(2-phenylethyl)amino]-3,5,6-trifluoro-4-[(2-phenylethyl)thio]benzenesulfonamide;

2-[(1-phenylethyl)amino]-3,5,6-trifluoro-4-[(2-phenylethyl)thio]benzenesulfonamide;

2-morpholin-4-yl-3,5,6-trifluoro-4-[(2-phenylethyl)thio]benzenesulfonamide;

2-(cyclohexylamino)-3,5,6-trifluoro-4-[(2-phenylethyl)thio]benzenesulfonamide;

2-(cycloheptylamino)-3,5,6-trifluoro-4-[(2-phenylethyl)thio]benzenesulfonamide;

2-(cyclooctylamino)-3,5,6-trifluoro-4-[(2-phenylethyl)thio]benzenesulfonamide;

2-(cyclododecylamino)-3,5,6-trifluoro-4-[(2-phenylethyl)thio]benzenesulfonamide;

2-[(2,6-dimethoxybenzyl)amino]-3,5,6-trifluoro-4-[(2-phenylethyl)thio]benzenesulfonamide;

2-[(3,4-dimethoxybenzyl)amino]-3,5,6-trifluoro-4-[(2-phenylethyl)thio]benzenesulfonamide;

2-(2,3-dihydro-1H-inden-2-ylamino)-3,5,6-trifluoro-4-[(2-phenylethyl)thio]benzenesulfonamide;

2-[(1S)-2,3-dihydro-1H-inden-1-ylamino]-3,5,6-trifluoro-4-[(2-phenylethyl)thio]benzenesulfonamide;

2-[(1S)-1,2,3,4-tetrahydronapthalen-1-ylamino]-3,5,6-trifluoro-4-[(2-phenylethyl)thio]benzenesulfonamide;

2-{[(1S,2R)-2-hydroxy-1,2-diphenylethyl]amino}-3,5,6-trifluoro-4-[(2-phenylethyl)thio]benzenesulfonamide;

2-(cyclooctylamino)-3,5,6-trifluoro-4-[(2-hydroxyethyl)thio]benzenesulfonamide;

2-(cyclododecylamino)-3,5,6-trifluoro-4-[(2-hydroxyethyl)thio]benzenesulfonamide;

2-[(2,6-dimethoxybenzyl)amino]-3,5,6-trifluoro-4-[(2-hydroxyethyl)thio]benzenesulfonamide;

2-[(3,4-dimethoxybenzyl)amino]-3,5,6-trifluoro-4-[(2-hydroxyethyl)thio]benzenesulfonamide;

2-[(1S)-2,3-dihydro-1H-inden-1-ylamino]-3,5,6-trifluoro-4-[(2-hydroxyethyl)thio]benzenesulfonamide;

2-[(1S)-1,2,3,4-tetrahydronapthalen-1-ylamino]-3,5,6-trifluoro-4-[(2-hydroxyethyl)thio]benzenesulfonamide;

2-{[(1S,2R)-2-hydroxy-1,2-diphenylethyl]amino}-3,5,6-trifluoro-4-[(2-hydroxyethyl)thio]benzenesulfonamide;

2-(cyclooctylamino)-3,5,6-trifluorobenzenesulfonamide;

2-(cyclododecylamino)-3,5,6-trifluorobenzenesulfonamide;

3-(methylamino)-2,5,6-trifluoro-4-[(2-phenylethyl)sulfonyl]benzenesulfonamide;

3-(tert-butylamino)-2,5,6-trifluoro-4-[(2-phenylethyl)sulfonyl]benzenesulfonamide;

3-(benzylamino)-2,5,6-trifluoro-4-[(2-phenylethyl)sulfonyl]benzenesulfonamide;

3-[(2-phenylethyl)amino]-2,5,6-trifluoro-4-[(2-phenylethyl)sulfonyl]benzenesulfonamide;
3-morpholin-4-yl-2,5,6-trifluoro-4-[(2-phenylethyl)sulfonyl]benzenesulfonamide;
3-(cyclooctylamino)-2,5,6-trifluoro-4-[(2-phenylethyl)sulfonyl]benzenesulfonamide;
3-(cyclododecylamino)-2,5,6-trifluoro-4-[(2-phenylethyl)sulfonyl]benzenesulfonamide;
3-[(2,6-dimethoxybenzyl)amino]-2,5,6-trifluoro-4-[(2-phenylethyl)sulfonyl]benzenesulfonamide;
3-[(3,4-dimethoxybenzyl)amino]-2,5,6-trifluoro-4-[(2-phenylethyl)sulfonyl]benzenesulfonamide;
3-(1-adamantylamino)-2,5,6-trifluoro-4-[(2-phenylethyl)sulfonyl]benzenesulfonamide;
3-(2,3-dihydro-1H-inden-2-ylamino)-2,5,6-trifluoro-4-[(2-phenylethyl)sulfonyl]benzenesulfonamide;
3-[(1S)-2,3-dihydro-1H-inden-1-ylamino]-2,5,6-trifluoro-4-[(2-phenylethyl)sulfonyl]benzenesulfonamide;
3-[(1S)-1,2,3,4-tetrahydronapthalen-1-ylamino)-2,5,6-trifluoro-4-[(2-phenylethyl)sulfonyl]benzenesulfonamide;
3-{[(1S,2R)-2-hydroxy-1,2-diphenylethyl]amino}-2,5,6-trifluoro-4-[(2-phenylethyl)sulfonyl]benzenesulfonamide;
3-{[(1R,2S)-2-hydroxy-1,2-diphenylethyl]amino}-2,5,6-trifluoro-4-[(2-phenylethyl)sulfonyl]benzenesulfonamide;
3-(benzylamino)-2,5,6-trifluoro-4-[(2-hydroxyethyl)sulfonyl]benzenesulfonamide;
3-(cyclooctylamino)-2,5,6-trifluoro-4-[(2-hydroxyethyl)sulfonyl]benzenesulfonamide;
3-(cyclododecylamino)-2,5,6-trifluoro-4-[(2-hydroxyethyl)sulfonyl]benzenesulfonamide;
3-[(2,6-dimethoxybenzyl)amino]-2,5,6-trifluoro-4-[(2-hydroxyethyl)sulfonyl]benzenesulfonamide;
3-[(3,4-dimethoxybenzyl)amino]-2,5,6-trifluoro-4-[(2-hydroxyethyl)sulfonyl]benzenesulfonamide;
3-[(1S)-2,3-dihydro-1H-inden-1-ylamino]-2,5,6-trifluoro-4-[(2-hydroxyethyl)sulfonyl]benzenesulfonamide;
3-[(1S)-1,2,3,4-tetrahydronapthalen-1-ylamino)-2,5,6-trifluoro-4-[(2-hydroxyethyl)sulfonyl]benzenesulfonamide;
3-{[(1S,2R)-2-hydroxy-1,2-diphenylethyl]amino}-2,5,6-trifluoro-4-[(2-hydroxyethyl)sulfonyl]benzenesulfonamide;
3,5-bis(cyclooctylamino)-2,6-difluoro-4-[(2-phenylethyl)sulfonyl]benzenesulfonamide; and
3,5-bis[(3,4-dimethoxybenzyl)amino]-2,6-difluoro-4-[(2-hydroxyethyl)sulfonyl]benzenesulfonamide.

3. A composition for use in control of conditions where inhibition of carbonic anhydrase is necessary, said composition comprising an effective amount of a fluorinated benzenesulfonamide according to claim 1 as part of a pharmaceutical formulation, and wherein the conditions are selected from the group consisting of intraocular hypertension, glaucoma, altitude sickness, headaches, migraine, neurological disorders, obesity and cancer, and signs and/or symptoms thereof.

4. A composition for use in control of conditions where inhibition of carbonic anhydrase is necessary, said composition comprising an effective amount of a fluorinated benzenesulfonamide according to claim 2 as part of a pharmaceutical formulation, and wherein the conditions are selected from the group consisting of intraocular hypertension, glaucoma, altitude sickness, headaches, migraine, neurological disorders, obesity and cancer, and signs and/or symptoms thereof.

5. Fluorinated benzenesulfonamides selected from the group consisting of:
2,3,5,6-tetrafluoro-4-hydrazinobenzenesulfonamide;
4-(2-benzylidenehydrazino)-2,3,5,6-tetrafluorobenzenesulfonamide;
2,3,5,6-tetrafluoro-4[(2-hydroxyethyl)thio]benzenesulfonamide;
2,3,5,6-tetrafluoro-4[(2-hydroxyethyl)sulfonyl]benzenesulfonamide;
2-{[4-(aminosulfonyl)-2,3,5,6-tetrafluorophenyl]sulfonyl}ethyl acetate;
2,3,5,6-tetrafluoro-4-(propylthio)benzenesulfonamide;
{[4-(aminosulfonyl)-2,3,5,6-tetrafluorophenyl]thio}acetic acid;
3-{[4-(aminosulfonyl)-2,3,5,6-tetrafluorophenyl]thio}propanoic acid;
6-{[4-(aminosulfonyl)-2,3,5,6-tetrafluorophenyl]amino}hexanoic acid;
2,3,5,6-tetrafluoro-4-(phenylthio)benzenesulfonamide;
2,3,5,6-tetrafluoro-4-(phenylsulfonyl)benzenesulfonamide;
2,3,5,6-tetrafluoro-4-phenoxybenzenesulfonamide;
4-(benzylthio)-2,3,5,6-tetrafluorobenzenesulfonamide;
4-(benzylamino)-2,3,5,6-tetrafluorobenzenesulfonamide;
2,3,5,6-tetrafluoro-4-{[2-(4-hydroxyphenyl)ethyl]amino}benzenesulfonamide;
2,3,5,6-tetrafluoro-4-[(2-phenylethyl)thio]benzenesulfonamide;
2,3,5,6-tetrafluoro-4-[(2-phenylethyl)sulfonyl]benzenesulfonamide;
2,3,5,6-tetrafluoro-4-morpholin-4-ylbenzenesulfonamide;
2,3,5,6-tetrafluoro-4-[(mesitylmethyl)thio]benzenesulfonamide;
4-[(4,6-dimethylpyrimidin-2-yl)thio]-2,3,5,6-tetrafluorobenzenesulfonamide;
4-(1,3-benzothiazol-2-ylthio)-2,3,5,6-tetrafluorobenzenesulfonamide;
4-(1-adamantylamino)-2,3,5,6-tetrafluorobenzenesulfonamide;
3-{[4-(aminosulfonyl)-2,3,5,6-tetrafluorophenyl]thio}-[1,2,3]thiadiazolo[3,4-a]benzimidazole; and
4-[(4,5-diphenyl-1H-imidazol-2-yl)thio]-2,3,5,6-tetrafluorobenzenesulfonamide; and
pharmaceutically acceptable salts thereof.

* * * * *